United States Patent
Krigsman et al.

(10) Patent No.: US 11,248,268 B2
(45) Date of Patent: Feb. 15, 2022

(54) IDENTIFICATION OF UNIQUE BLOOD-BASED GENE EXPRESSION PROFILES IN CHILDREN WITH REGRESSIVE AUTISM SPECTRUM DISORDER (ASD) AND ILEOCOLITIS

(71) Applicants: WAKE FOREST UNIVERSITY HEALTH SCIENCES, Winston-Salem, NC (US); Arthur Krigsman, Far Rockaway, NY (US)

(72) Inventors: Arthur Krigsman, Far Rockaway, NY (US); Stephen Walker, Winston-Salem, NC (US)

(73) Assignees: Arthur Krigsman, Far Rockaway, NY (US); Wake Forest University Health Sciences, Winston-Salem, NC (US)

( * ) Notice: Subject to any disclaimer, the term of this patent is extended or adjusted under 35 U.S.C. 154(b) by 99 days.

(21) Appl. No.: 16/088,359

(22) PCT Filed: Mar. 24, 2017

(86) PCT No.: PCT/US2017/024037
§ 371 (c)(1),
(2) Date: Sep. 25, 2018

(87) PCT Pub. No.: WO2017/172521
PCT Pub. Date: Oct. 5, 2017

(65) Prior Publication Data
US 2019/0112660 A1    Apr. 18, 2019

Related U.S. Application Data

(60) Provisional application No. 62/315,391, filed on Mar. 30, 2016.

(51) Int. Cl.
| | | |
|---|---|---|
| *C12Q 1/68* | (2018.01) | |
| *C12P 19/34* | (2006.01) | |
| *C12Q 1/6883* | (2018.01) | |
| *G01N 33/48* | (2006.01) | |
| *G01N 33/68* | (2006.01) | |

(52) U.S. Cl.
CPC ............ *C12Q 1/6883* (2013.01); *C12Q 1/68* (2013.01); *G01N 33/48* (2013.01); *G01N 33/689* (2013.01); *G01N 33/6893* (2013.01); *G01N 33/6896* (2013.01); *C12Q 2600/158* (2013.01); *G01N 2800/06* (2013.01)

(58) Field of Classification Search
CPC ............ C12Q 1/6883; C12Q 2600/158; C12Q 2600/106; C12Q 2600/156; C12Q 1/68
See application file for complete search history.

(56) References Cited

U.S. PATENT DOCUMENTS

| | | |
|---|---|---|
| 2010/0267575 A1 | 10/2010 | Xu et al. |
| 2014/0148348 A1 | 5/2014 | Kuslich et al. |
| 2015/0361499 A1 | 12/2015 | Walker et al. |

FOREIGN PATENT DOCUMENTS

| | | |
|---|---|---|
| WO | 2014201104 A2 | 12/2014 |

OTHER PUBLICATIONS

Powell JE, Renders AK, McRae AF, Caracella A, Smith S, et al. (2012) The Brisbane Systems Genetics Study: Genetical Genomics Meets Complex Trait Genetics. PLoS One 7(4): e35430 (Year: 2012).*
Gregg, J.P. et al. Gene expression changes in children with autism. Genomics 91 (2008) 22-29. (Year: 2008).*
J. Perren Cobb, et al. "Sepsis gene expression profiling: Murine splenic compared with hepatic responses determined by using complementary DNA microarrays" Crit Care Med 2002 vol. 30, No. 12 (Year: 2002).*
W. Enard et al., "Intra- and Interspecific Variation in Primate Gene Expression Patterns" Science (Apr. 12, 2002) vol. 296, pp. 340-343. (Year: 2002).*
V.G. Cheung et al. "Natural variation in human gene expression assessed in lymphoblastoid cells" Nature Genetics (vol. 33) March, pp. 422-425. (Year: 2002).*
International Search Report and Written Opinion for PCT International Application No. PCT/US2017/024037 dated Jun. 20, 2017.

* cited by examiner

*Primary Examiner* — Stephen T Kapushoc
(74) *Attorney, Agent, or Firm* — Saul Ewing Arnstein & Lehr LLP; Kathryn Doyle; Justin Crotty

(57) ABSTRACT

The invention provides compositions and methods for identifying autism and autism spectrum disorders in humans. The invention also includes compositions and methods for identifying unique blood-based gene expression profiles in children with regressive autism spectrum disorder (ASD) and ileocolitis.

6 Claims, 14 Drawing Sheets
Specification includes a Sequence Listing.

ROC Curve for gene MTHFD2

SEQUENCE LISTING

```
<160> NUMBER OF SEQ ID NOS: 18

<210> SEQ ID NO 1
<211> LENGTH: 2701
<212> TYPE: PRT
<213> ORGANISM: Homo sapiens

<400> SEQUENCE: 1

Met Ala Glu Glu Gly Ala Val Ala Val Cys Val Arg Val Arg Pro Leu
1               5                   10                  15

Asn Ser Arg Glu Glu Ser Leu Gly Glu Thr Ala Gln Val Tyr Trp Lys
            20                  25                  30

Thr Asp Asn Asn Val Ile Tyr Gln Val Asp Gly Ser Lys Ser Phe Asn
        35                  40                  45

Phe Asp Arg Val Phe His Gly Asn Glu Thr Thr Lys Asn Val Tyr Glu
    50                  55                  60

Glu Ile Ala Ala Pro Ile Ile Asp Ser Ala Ile Gln Gly Tyr Asn Gly
65                  70                  75                  80

Thr Ile Phe Ala Tyr Gly Gln Thr Ala Ser Gly Lys Thr Tyr Thr Met
                85                  90                  95

Met Gly Ser Glu Asp His Leu Gly Val Ile Pro Arg Ala Ile His Asp
            100                 105                 110

Ile Phe Gln Lys Ile Lys Lys Phe Pro Asp Arg Glu Phe Leu Leu Arg
        115                 120                 125

Val Ser Tyr Met Glu Ile Tyr Asn Glu Thr Ile Thr Asp Leu Leu Cys
    130                 135                 140

Gly Thr Gln Lys Met Lys Pro Leu Ile Ile Arg Glu Asp Val Asn Arg
145                 150                 155                 160

Asn Val Tyr Val Ala Asp Leu Thr Glu Glu Val Val Tyr Thr Ser Glu
                165                 170                 175

Met Ala Leu Lys Trp Ile Thr Lys Gly Glu Lys Ser Arg His Tyr Gly
            180                 185                 190

Glu Thr Lys Met Asn Gln Arg Ser Ser Arg Ser His Thr Ile Phe Arg
        195                 200                 205

Met Ile Leu Glu Ser Arg Glu Lys Gly Glu Pro Ser Asn Cys Glu Gly
    210                 215                 220

Ser Val Lys Val Ser His Leu Asn Leu Val Asp Leu Ala Gly Ser Glu
225                 230                 235                 240

Arg Ala Ala Gln Thr Gly Ala Ala Gly Val Arg Leu Lys Glu Gly Cys
                245                 250                 255

Asn Ile Asn Arg Ser Leu Phe Ile Leu Gly Gln Val Ile Lys Lys Leu
            260                 265                 270

Ser Asp Gly Gln Val Gly Gly Phe Ile Asn Tyr Arg Asp Ser Lys Leu
        275                 280                 285
```

```
Thr Arg Ile Leu Gln Asn Ser Leu Gly Gly Asn Ala Lys Thr Arg Ile
    290                 295                 300

Ile Cys Thr Ile Thr Pro Val Ser Phe Asp Glu Thr Leu Thr Ala Leu
305                 310                 315                 320

Gln Phe Ala Ser Thr Ala Lys Tyr Met Lys Asn Thr Pro Tyr Val Asn
                325                 330                 335

Glu Val Ser Thr Asp Glu Ala Leu Leu Lys Arg Tyr Arg Lys Glu Ile
                340                 345                 350

Met Asp Leu Lys Lys Gln Leu Glu Glu Val Ser Leu Glu Thr Arg Ala
            355                 360                 365

Gln Ala Met Glu Lys Asp Gln Leu Ala Gln Leu Glu Glu Lys Asp
        370                 375                 380

Leu Leu Gln Lys Val Gln Asn Glu Lys Ile Glu Asn Leu Thr Arg Met
385                 390                 395                 400

Leu Val Thr Ser Ser Leu Thr Leu Gln Gln Glu Leu Lys Ala Lys
                405                 410                 415

Arg Lys Arg Arg Val Thr Trp Cys Leu Gly Lys Ile Asn Lys Met Lys
                420                 425                 430

Asn Ser Asn Tyr Ala Asp Gln Phe Asn Ile Pro Thr Asn Ile Thr Thr
            435                 440                 445

Lys Thr His Lys Leu Ser Ile Asn Leu Leu Arg Glu Ile Asp Glu Ser
        450                 455                 460

Val Cys Ser Glu Ser Asp Val Phe Ser Asn Thr Leu Asp Thr Leu Ser
465                 470                 475                 480

Glu Ile Glu Trp Asn Pro Ala Thr Lys Leu Leu Asn Gln Glu Asn Ile
                485                 490                 495

Glu Ser Glu Leu Asn Ser Leu Arg Ala Asp Tyr Asp Asn Leu Val Leu
            500                 505                 510

Asp Tyr Glu Gln Leu Arg Thr Glu Lys Glu Glu Met Glu Leu Lys Leu
        515                 520                 525

Lys Glu Lys Asn Asp Leu Asp Glu Phe Glu Ala Leu Glu Arg Lys Thr
    530                 535                 540

Lys Lys Asp Gln Glu Met Gln Leu Ile His Glu Ile Ser Asn Leu Lys
545                 550                 555                 560

Asn Leu Val Lys His Ala Glu Val Tyr Asn Gln Asp Leu Glu Asn Glu
                565                 570                 575

Leu Ser Ser Lys Val Glu Leu Leu Arg Glu Lys Glu Asp Gln Ile Lys
            580                 585                 590

Lys Leu Gln Glu Tyr Ile Asp Ser Gln Lys Leu Glu Asn Ile Lys Met
        595                 600                 605

Asp Leu Ser Tyr Ser Leu Glu Ser Ile Glu Asp Pro Lys Gln Met Lys
    610                 615                 620

Gln Thr Leu Phe Asp Ala Glu Thr Val Ala Leu Asp Ala Lys Arg Glu
625                 630                 635                 640

Ser Ala Phe Leu Arg Ser Glu Asn Leu Leu Lys Glu Lys Met Lys
                645                 650                 655

Glu Leu Ala Thr Thr Tyr Lys Gln Met Glu Asn Asp Ile Gln Leu Tyr
                660                 665                 670

Gln Ser Gln Leu Glu Ala Lys Lys Lys Met Gln Val Asp Leu Glu Lys
            675                 680                 685

Glu Leu Gln Ser Ala Phe Asn Glu Ile Thr Lys Leu Thr Ser Leu Ile
        690                 695                 700
```

```
Asp Gly Lys Val Pro Lys Asp Leu Leu Cys Asn Leu Glu Leu Glu Gly
705                 710                 715                 720

Lys Ile Thr Asp Leu Gln Lys Glu Leu Asn Lys Glu Val Glu Asn
            725                 730                 735

Glu Ala Leu Arg Glu Val Ile Leu Leu Ser Glu Leu Lys Ser Leu
            740                 745                 750

Pro Ser Glu Val Glu Arg Leu Arg Lys Glu Ile Gln Asp Lys Ser Glu
            755                 760                 765

Glu Leu His Ile Ile Thr Ser Glu Lys Asp Lys Leu Phe Ser Glu Val
    770                 775                 780

Val His Lys Glu Ser Arg Val Gln Gly Leu Leu Glu Glu Ile Gly Lys
785                 790                 795                 800

Thr Lys Asp Asp Leu Ala Thr Thr Gln Ser Asn Tyr Lys Ser Thr Asp
                805                 810                 815

Gln Glu Phe Gln Asn Phe Lys Thr Leu His Met Asp Phe Glu Gln Lys
                820                 825                 830

Tyr Lys Met Val Leu Glu Glu Asn Glu Arg Met Asn Gln Glu Ile Val
            835                 840                 845

Asn Leu Ser Lys Glu Ala Gln Lys Phe Asp Ser Ser Leu Gly Ala Leu
850                 855                 860

Lys Thr Glu Leu Ser Tyr Lys Thr Gln Glu Leu Gln Glu Lys Thr Arg
865                 870                 875                 880

Glu Val Gln Glu Arg Leu Asn Glu Met Glu Gln Leu Lys Glu Gln Leu
                885                 890                 895

Glu Asn Arg Asp Ser Thr Leu Gln Thr Val Glu Arg Glu Lys Thr Leu
            900                 905                 910

Ile Thr Glu Lys Leu Gln Gln Thr Leu Glu Glu Val Lys Thr Leu Thr
            915                 920                 925

Gln Glu Lys Asp Asp Leu Lys Gln Leu Gln Glu Ser Leu Gln Ile Glu
    930                 935                 940

Arg Asp Gln Leu Lys Ser Asp Ile His Asp Thr Val Asn Met Asn Ile
945                 950                 955                 960

Asp Thr Gln Glu Gln Leu Arg Asn Ala Leu Glu Ser Leu Lys Gln His
                965                 970                 975

Gln Glu Thr Ile Asn Thr Leu Lys Ser Lys Ile Ser Glu Glu Val Ser
            980                 985                 990

Arg Asn Leu His Met Glu Glu Asn  Thr Gly Glu Thr Lys  Asp Glu Phe
            995                 1000                1005

Gln Gln  Lys Met Val Gly Ile  Asp Lys Lys Gln Asp  Leu Glu Ala
    1010                1015                1020

Lys Asn  Thr Gln Thr Leu  Ala Asp Val Lys Asp  Asn Glu Ile
    1025                1030                1035

Ile Glu  Gln Gln Arg Lys Ile  Phe Ser Leu Ile Gln  Glu Lys Asn
    1040                1045                1050

Glu Leu  Gln Gln Met Leu Glu  Ser Val Ile Ala Glu  Lys Glu Gln
    1055                1060                1065

Leu Lys  Thr Asp Leu Lys Glu  Asn Ile Glu Met Thr  Ile Glu Asn
    1070                1075                1080

Gln Glu  Glu Leu Arg Leu Leu  Gly Asp Glu Leu Lys  Lys Gln Gln
    1085                1090                1095

Glu Ile  Val Ala Gln Glu Lys  Asn His Ala Ile Lys  Lys Glu Gly
    1100                1105                1110

Glu Leu  Ser Arg Thr Cys Asp  Arg Leu Ala Glu Val  Glu Glu Lys
```

```
                  1115                1120                1125
Leu Lys Glu Lys Ser Gln Gln Leu Gln Glu Lys Gln Gln Gln Leu
            1130                1135                1140
Leu Asn Val Gln Glu Glu Met Ser Glu Met Gln Lys Lys Ile Asn
            1145                1150                1155
Glu Ile Glu Asn Leu Lys Asn Glu Leu Lys Asn Lys Glu Leu Thr
            1160                1165                1170
Leu Glu His Met Glu Thr Glu Arg Leu Glu Leu Ala Gln Lys Leu
            1175                1180                1185
Asn Glu Asn Tyr Glu Glu Val Lys Ser Ile Thr Lys Glu Arg Lys
            1190                1195                1200
Val Leu Lys Glu Leu Gln Lys Ser Phe Glu Thr Glu Arg Asp His
            1205                1210                1215
Leu Arg Gly Tyr Ile Arg Glu Ile Glu Ala Thr Gly Leu Gln Thr
            1220                1225                1230
Lys Glu Glu Leu Lys Ile Ala His Ile His Leu Lys Glu His Gln
            1235                1240                1245
Glu Thr Ile Asp Glu Leu Arg Arg Ser Val Ser Glu Lys Thr Ala
            1250                1255                1260
Gln Ile Ile Asn Thr Gln Asp Leu Glu Lys Ser His Thr Lys Leu
            1265                1270                1275
Gln Glu Glu Ile Pro Val Leu His Glu Glu Gln Glu Leu Leu Pro
            1280                1285                1290
Asn Val Lys Glu Val Ser Glu Thr Gln Glu Thr Met Asn Glu Leu
            1295                1300                1305
Glu Leu Leu Thr Glu Gln Ser Thr Thr Lys Asp Ser Thr Thr Leu
            1310                1315                1320
Ala Arg Ile Glu Met Glu Arg Leu Arg Leu Asn Glu Lys Phe Gln
            1325                1330                1335
Glu Ser Gln Glu Glu Ile Lys Ser Leu Thr Lys Glu Arg Asp Asn
            1340                1345                1350
Leu Lys Thr Ile Lys Glu Ala Leu Glu Val Lys His Asp Gln Leu
            1355                1360                1365
Lys Glu His Ile Arg Glu Thr Leu Ala Lys Ile Gln Glu Ser Gln
            1370                1375                1380
Ser Lys Gln Glu Gln Ser Leu Asn Met Lys Glu Lys Asp Asn Glu
            1385                1390                1395
Thr Thr Lys Ile Val Ser Glu Met Glu Gln Phe Lys Pro Lys Asp
            1400                1405                1410
Ser Ala Leu Leu Arg Ile Glu Ile Glu Met Leu Gly Leu Ser Lys
            1415                1420                1425
Arg Leu Gln Glu Ser His Asp Glu Met Lys Ser Val Ala Lys Glu
            1430                1435                1440
Lys Asp Asp Leu Gln Arg Leu Gln Glu Val Leu Gln Ser Glu Ser
            1445                1450                1455
Asp Gln Leu Lys Glu Asn Ile Lys Glu Ile Val Ala Lys His Leu
            1460                1465                1470
Glu Thr Glu Glu Glu Leu Lys Val Ala His Cys Cys Leu Lys Glu
            1475                1480                1485
Gln Glu Glu Thr Ile Asn Glu Leu Arg Val Asn Leu Ser Glu Lys
            1490                1495                1500
Glu Thr Glu Ile Ser Thr Ile Gln Lys Gln Leu Glu Ala Ile Asn
            1505                1510                1515
```

Asp Lys Leu Gln Asn Lys Ile Gln Glu Ile Tyr Glu Lys Glu Glu
1520                    1525                1530

Gln Phe Asn Ile Lys Gln Ile Ser Glu Val Gln Glu Lys Val Asn
1535                    1540                1545

Glu Leu Lys Gln Phe Lys Glu His Arg Lys Ala Lys Asp Ser Ala
1550                    1555                1560

Leu Gln Ser Ile Glu Ser Lys Met Leu Glu Leu Thr Asn Arg Leu
1565                    1570                1575

Gln Glu Ser Gln Glu Glu Ile Gln Ile Met Ile Lys Glu Lys Glu
1580                    1585                1590

Glu Met Lys Arg Val Gln Glu Ala Leu Gln Ile Glu Arg Asp Gln
1595                    1600                1605

Leu Lys Glu Asn Thr Lys Glu Ile Val Ala Lys Met Lys Glu Ser
1610                    1615                1620

Gln Glu Lys Glu Tyr Gln Phe Leu Lys Met Thr Ala Val Asn Glu
1625                    1630                1635

Thr Gln Glu Lys Met Cys Glu Ile Glu His Leu Lys Glu Gln Phe
1640                    1645                1650

Glu Thr Gln Lys Leu Asn Leu Glu Asn Ile Glu Thr Glu Asn Ile
1655                    1660                1665

Arg Leu Thr Gln Ile Leu His Glu Asn Leu Glu Glu Met Arg Ser
1670                    1675                1680

Val Thr Lys Glu Arg Asp Asp Leu Arg Ser Val Glu Glu Thr Leu
1685                    1690                1695

Lys Val Glu Arg Asp Gln Leu Lys Glu Asn Leu Arg Glu Thr Ile
1700                    1705                1710

Thr Arg Asp Leu Glu Lys Gln Glu Glu Leu Lys Ile Val His Met
1715                    1720                1725

His Leu Lys Glu His Gln Glu Thr Ile Asp Lys Leu Arg Gly Ile
1730                    1735                1740

Val Ser Glu Lys Thr Asn Glu Ile Ser Asn Met Gln Lys Asp Leu
1745                    1750                1755

Glu His Ser Asn Asp Ala Leu Lys Ala Gln Asp Leu Lys Ile Gln
1760                    1765                1770

Glu Glu Leu Arg Ile Ala His Met His Leu Lys Glu Gln Gln Glu
1775                    1780                1785

Thr Ile Asp Lys Leu Arg Gly Ile Val Ser Glu Lys Thr Asp Lys
1790                    1795                1800

Leu Ser Asn Met Gln Lys Asp Leu Glu Asn Ser Asn Ala Lys Leu
1805                    1810                1815

Gln Glu Lys Ile Gln Glu Leu Lys Ala Asn Glu His Gln Leu Ile
1820                    1825                1830

Thr Leu Lys Lys Asp Val Asn Glu Thr Gln Lys Lys Val Ser Glu
1835                    1840                1845

Met Glu Gln Leu Lys Lys Gln Ile Lys Asp Gln Ser Leu Thr Leu
1850                    1855                1860

Ser Lys Leu Glu Ile Glu Asn Leu Asn Leu Ala Gln Lys Leu His
1865                    1870                1875

Glu Asn Leu Glu Glu Met Lys Ser Val Met Lys Glu Arg Asp Asn
1880                    1885                1890

Leu Arg Arg Val Glu Glu Thr Leu Lys Leu Glu Arg Asp Gln Leu
1895                    1900                1905

```
Lys Glu Ser Leu Gln Glu Thr Lys Ala Arg Asp Leu Glu Ile Gln
    1910                1915                1920

Gln Glu Leu Lys Thr Ala Arg Met Leu Ser Lys Glu His Lys Glu
    1925                1930                1935

Thr Val Asp Lys Leu Arg Glu Lys Ile Ser Glu Lys Thr Ile Gln
    1940                1945                1950

Ile Ser Asp Ile Gln Lys Asp Leu Asp Lys Ser Lys Asp Glu Leu
    1955                1960                1965

Gln Lys Lys Ile Gln Glu Leu Gln Lys Lys Glu Leu Gln Leu Leu
    1970                1975                1980

Arg Val Lys Glu Asp Val Asn Met Ser His Lys Lys Ile Asn Glu
    1985                1990                1995

Met Glu Gln Leu Lys Lys Gln Phe Glu Ala Gln Asn Leu Ser Met
    2000                2005                2010

Gln Ser Val Arg Met Asp Asn Phe Gln Leu Thr Lys Lys Leu His
    2015                2020                2025

Glu Ser Leu Glu Glu Ile Arg Ile Val Ala Lys Glu Arg Asp Glu
    2030                2035                2040

Leu Arg Arg Ile Lys Glu Ser Leu Lys Met Glu Arg Asp Gln Phe
    2045                2050                2055

Ile Ala Thr Leu Arg Glu Met Ile Ala Arg Asp Arg Gln Asn His
    2060                2065                2070

Gln Val Lys Pro Glu Lys Arg Leu Leu Ser Asp Gly Gln Gln His
    2075                2080                2085

Leu Thr Glu Ser Leu Arg Glu Lys Cys Ser Arg Ile Lys Glu Leu
    2090                2095                2100

Leu Lys Arg Tyr Ser Glu Met Asp Asp His Tyr Glu Cys Leu Asn
    2105                2110                2115

Arg Leu Ser Leu Asp Leu Glu Lys Glu Ile Glu Phe Gln Lys Glu
    2120                2125                2130

Leu Ser Met Arg Val Lys Ala Asn Leu Ser Leu Pro Tyr Leu Gln
    2135                2140                2145

Thr Lys His Ile Glu Lys Leu Phe Thr Ala Asn Gln Arg Cys Ser
    2150                2155                2160

Met Glu Phe His Arg Ile Met Lys Lys Leu Lys Tyr Val Leu Ser
    2165                2170                2175

Tyr Val Thr Lys Ile Lys Glu Glu Gln His Glu Ser Ile Asn Lys
    2180                2185                2190

Phe Glu Met Asp Phe Ile Asp Glu Val Glu Lys Gln Lys Glu Leu
    2195                2200                2205

Leu Ile Lys Ile Gln His Leu Gln Gln Asp Cys Asp Val Pro Ser
    2210                2215                2220

Arg Glu Leu Arg Asp Leu Lys Leu Asn Gln Asn Met Asp Leu His
    2225                2230                2235

Ile Glu Glu Ile Leu Lys Asp Phe Ser Glu Ser Glu Phe Pro Ser
    2240                2245                2250

Ile Lys Thr Glu Phe Gln Gln Val Leu Ser Asn Arg Lys Glu Met
    2255                2260                2265

Thr Gln Phe Leu Glu Glu Trp Leu Asn Thr Arg Phe Asp Ile Glu
    2270                2275                2280

Lys Leu Lys Asn Gly Ile Gln Lys Glu Asn Asp Arg Ile Cys Gln
    2285                2290                2295

Val Asn Asn Phe Phe Asn Asn Arg Ile Ile Ala Ile Met Asn Glu
```

```
            2300                2305                2310
Ser  Thr  Glu  Phe  Glu  Glu  Arg  Ser  Ala  Thr  Ile  Ser  Lys  Glu  Trp
       2315                2320                2325

Glu  Gln  Asp  Leu  Lys  Ser  Leu  Lys  Glu  Lys  Asn  Glu  Lys  Leu  Phe
       2330                2335                2340

Lys  Asn  Tyr  Gln  Thr  Leu  Lys  Thr  Ser  Leu  Ala  Ser  Gly  Ala  Gln
       2345                2350                2355

Val  Asn  Pro  Thr  Thr  Gln  Asp  Asn  Lys  Asn  Pro  His  Val  Thr  Ser
       2360                2365                2370

Arg  Ala  Thr  Gln  Leu  Thr  Thr  Glu  Lys  Ile  Arg  Glu  Leu  Glu  Asn
       2375                2380                2385

Ser  Leu  His  Glu  Ala  Lys  Glu  Ser  Ala  Met  His  Lys  Glu  Ser  Lys
       2390                2395                2400

Ile  Ile  Lys  Met  Gln  Lys  Glu  Leu  Glu  Val  Thr  Asn  Asp  Ile  Ile
       2405                2410                2415

Ala  Lys  Leu  Gln  Ala  Lys  Val  His  Glu  Ser  Asn  Lys  Cys  Leu  Glu
       2420                2425                2430

Lys  Thr  Lys  Glu  Thr  Ile  Gln  Val  Leu  Gln  Asp  Lys  Val  Ala  Leu
       2435                2440                2445

Gly  Ala  Lys  Pro  Tyr  Lys  Glu  Glu  Ile  Glu  Asp  Leu  Lys  Met  Lys
       2450                2455                2460

Leu  Val  Lys  Ile  Asp  Leu  Glu  Lys  Met  Lys  Asn  Ala  Lys  Glu  Phe
       2465                2470                2475

Glu  Lys  Glu  Ile  Ser  Ala  Thr  Lys  Ala  Thr  Val  Glu  Tyr  Gln  Lys
       2480                2485                2490

Glu  Val  Ile  Arg  Leu  Leu  Arg  Glu  Asn  Leu  Arg  Arg  Ser  Gln  Gln
       2495                2500                2505

Ala  Gln  Asp  Thr  Ser  Val  Ile  Ser  Glu  His  Thr  Asp  Pro  Gln  Pro
       2510                2515                2520

Ser  Asn  Lys  Pro  Leu  Thr  Cys  Gly  Gly  Gly  Ser  Gly  Ile  Val  Gln
       2525                2530                2535

Asn  Thr  Lys  Ala  Leu  Ile  Leu  Lys  Ser  Glu  His  Ile  Arg  Leu  Glu
       2540                2545                2550

Lys  Glu  Ile  Ser  Lys  Leu  Lys  Gln  Gln  Asn  Glu  Gln  Leu  Ile  Lys
       2555                2560                2565

Gln  Lys  Asn  Glu  Leu  Leu  Ser  Asn  Asn  Gln  His  Leu  Ser  Asn  Glu
       2570                2575                2580

Val  Lys  Thr  Trp  Lys  Glu  Arg  Thr  Leu  Lys  Arg  Glu  Ala  His  Lys
       2585                2590                2595

Gln  Val  Thr  Cys  Glu  Asn  Ser  Pro  Lys  Ser  Pro  Lys  Val  Thr  Gly
       2600                2605                2610

Thr  Ala  Ser  Lys  Lys  Lys  Gln  Ile  Thr  Pro  Ser  Gln  Cys  Lys  Glu
       2615                2620                2625

Arg  Asn  Leu  Gln  Asp  Pro  Val  Pro  Lys  Glu  Ser  Pro  Lys  Ser  Cys
       2630                2635                2640

Phe  Phe  Asp  Ser  Arg  Ser  Lys  Ser  Leu  Pro  Ser  Pro  His  Pro  Val
       2645                2650                2655

Arg  Tyr  Phe  Asp  Asn  Ser  Ser  Leu  Gly  Leu  Cys  Pro  Glu  Val  Gln
       2660                2665                2670

Asn  Ala  Gly  Ala  Glu  Ser  Val  Asp  Ser  Gln  Pro  Gly  Pro  Trp  His
       2675                2680                2685

Ala  Ser  Ser  Gly  Lys  Asp  Val  Pro  Glu  Cys  Lys  Thr  Gln
       2690                2695                2700
```

<210> SEQ ID NO 2
<211> LENGTH: 8630
<212> TYPE: DNA
<213> ORGANISM: Homo sapiens

<400> SEQUENCE: 2

| | | | | | |
|---|---|---|---|---|---|
| taaatttaaa | ggcggggcgg | cctgtgagcc | ctgaagtgcc | ggccgcggag | ggtcctggcc | 60 |
| attttcctgg | gaccagttca | gcctgatagg | atggcggagg | aaggagccgt | ggccgtctgc | 120 |
| gtgcgagtgc | ggccgctgaa | cagcagagaa | gaatcacttg | gagaaactgc | ccaagtttac | 180 |
| tggaaaactg | acaataatgt | catttatcaa | gttgatggaa | gtaaatcctt | caattttgat | 240 |
| cgtgtctttc | atggtaatga | aactaccaaa | aatgtgtatg | aagaaatagc | agcaccaatc | 300 |
| atcgattctg | ccatacaagg | ctacaatggt | actatatttg | cctatggaca | gactgcttca | 360 |
| ggaaaaacat | ataccatgat | gggttcagaa | gatcatttgg | gagttatacc | agggcaatt | 420 |
| catgacattt | tccaaaaaat | taagaagttt | cctgataggg | aatttctctt | acgtgtatct | 480 |
| tacatggaaa | tatacaatga | aaccattaca | gatttactct | gtggcactca | aaaaatgaaa | 540 |
| cctttaatta | ttcgagaaga | tgtcaatagg | aatgtgtatg | ttgctgatct | cacagaagaa | 600 |
| gttgtatata | catcagaaat | ggctttgaaa | tggattacaa | agggagaaaa | gagcaggcat | 660 |
| tatggagaaa | caaaaatgaa | tcaaagaagc | agtcgttctc | ataccatctt | taggatgatt | 720 |
| ttggaaagca | gagagaaggg | tgaaccttct | aattgtgaag | gatctgttaa | ggtatcccat | 780 |
| ttgaatttgg | ttgatcttgc | aggcagtgaa | agagctgctc | aaacaggcgc | tgcaggtgtg | 840 |
| cggctcaagg | aaggctgtaa | tataaatcga | agcttattta | ttttgggaca | agtgatcaag | 900 |
| aaacttagtg | atggacaagt | tggtggtttc | ataaattatc | gagatagcaa | gttaacacga | 960 |
| attctccaga | attccttggg | aggaaatgca | agacacgta | ttatctgcac | aattactcca | 1020 |
| gtatcttttg | atgaaacact | tactgctctc | cagtttgcca | gtactgctaa | atatatgaag | 1080 |
| aatactcctt | atgttaatga | ggtatcaact | gatgaagctc | tcctgaaaag | gtatagaaaa | 1140 |
| gaaataatgg | atcttaaaaa | acaattagag | gaggtttctt | tagagacgcg | ggctcaggca | 1200 |
| atggaaaaag | accaattggc | ccaacttttg | gaagaaaaag | atttgcttca | gaaagtacag | 1260 |
| aatgagaaaa | ttgaaaactt | aacacggatg | ctggtgacct | cttcttccct | cacgttgcaa | 1320 |
| caggaattaa | aggctaaaag | aaaacgaaga | gttacttggt | gccttggcaa | aattaacaaa | 1380 |
| atgaagaact | caaactatgc | agatcaattt | aatataccaa | caaatataac | aacaaaaaca | 1440 |
| cataagcttt | ctataaattt | attacgagaa | attgatgaat | ctgtctgttc | agagtctgat | 1500 |
| gttttcagta | acactcttga | tacattaagt | gagatagaat | ggaatccagc | aacaaagcta | 1560 |
| ctaaatcagg | agaatataga | aagtgagttg | aactcacttc | gtgctgacta | tgataatctg | 1620 |
| gtattagact | atgaacaact | acgaacagaa | aaagaagaaa | tggaattgaa | attaaaagaa | 1680 |
| aagaatgatt | tggatgaatt | tgaggctcta | gaaagaaaaa | ctaaaaaaga | tcaagagatg | 1740 |
| caactaattc | atgaaatttc | gaacttaaag | aatttagtta | agcatgcaga | agtatataat | 1800 |
| caagatcttg | agaatgaact | cagttcaaaa | gtagagctgc | ttagagaaaa | ggaagaccag | 1860 |
| attaagaagc | tacaggaata | catagactct | caaaagctag | aaaatataaa | aatggacttg | 1920 |
| tcatactcat | tggaaagcat | tgaagaccca | aaacaaatga | agcagactct | gtttgatgct | 1980 |
| gaaactgtag | cccttgatgc | caagagagaa | tcagcctttc | ttagaagtga | aaatctggag | 2040 |
| ctgaaggaga | aaatgaaaga | acttgcaact | acatacaagc | aaatggaaaa | tgatattcag | 2100 |

```
ttatatcaaa gccagttgga ggcaaaaaag aaaatgcaag ttgatctgga gaaagaatta    2160
caatctgctt ttaatgagat aacaaaactc acctccctta tagatggcaa agttccaaaa    2220
gatttgctct gtaatttgga attggaagga aagattactg atcttcagaa agaactaaat    2280
aaagaagttg aagaaaatga agctttgcgg gaagaagtca ttttgctttc agaattgaaa    2340
tctttacctt ctgaagtaga aaggctgagg aaagagatac aagacaaatc tgaagagctc    2400
catataataa catcagaaaa agataaattg ttttctgaag tagttcataa ggagagtaga    2460
gttcaaggtt tacttgaaga aattgggaaa acaaagatg acctagcaac tacacagtcg    2520
aattataaaa gcactgatca agaattccaa aatttcaaaa cccttcatat ggactttgag    2580
caaaagtata agatggtcct tgaggagaat gagagaatga atcaggaaat agttaatctc    2640
tctaaagaag cccaaaaatt tgattcgagt ttgggtgctt tgaagaccga gctttcttac    2700
aagacccaag aacttcagga gaaaacacgt gaggttcaag aaagactaaa tgagatggaa    2760
cagctgaagg aacaattaga aaatagagat tctacgctgc aaactgtaga aagggagaaa    2820
acactgatta ctgagaaact gcagcaaact ttagaagaag taaaaacttt aactcaagaa    2880
aaagatgatc taaaacaact ccaagaaagc ttgcaaattg agagggacca actcaaaagt    2940
gatattcacg atactgttaa catgaatata gatactcaag aacaattacg aaatgctctt    3000
gagtctctga acaacatca agaaacaatt aatacactaa aatcgaaaat ttctgaggaa    3060
gtttccagga atttgcatat ggaggaaaat acaggagaaa ctaaagatga atttcagcaa    3120
aagatggttg gcatagataa aaaacaggat ttggaagcta aaaataccca aacactaact    3180
gcagatgtta aggataatga gataattgag caacaaagga agatattttc tttaatacag    3240
gagaaaaatg aactccaaca aatgttagag agtgttatag cagaaaagga acaattgaag    3300
actgacctaa aggaaaatat tgaaatgacc attgaaaacc aggaagaatt aagacttctt    3360
ggggatgaac ttaaaaagca acaagagata gttgcacaag aaaagaacca tgccataaag    3420
aaagaaggag agctttctag gacctgtgac agactggcag aagttgaaga aaaactaaag    3480
gaaaagagcc agcaactcca agaaaaacag caacaacttc ttaatgtaca agaagagatg    3540
agtgagatgc agaaaaagat taatgaaata gagaatttaa agaatgaatt aaagaacaaa    3600
gaattgacat tggaacatat ggaaacagag aggcttgagt tggctcagaa acttaatgaa    3660
aattatgagg aagtgaaatc tataaccaaa gaaagaaaag ttctaaagga attacagaag    3720
tcatttgaaa cagagagaga ccaccttaga ggatatataa gagaaattga agctacaggc    3780
ctacaaacca aagaagaact aaaaattgct catattcacc taaaagaaca ccaagaaact    3840
attgatgaac taagaagaag cgtatctgag aagacagctc aaataataaa tactcaggac    3900
ttagaaaaat cccataccaa attacaagaa gagatcccag tgcttcatga ggaacaagag    3960
ttactgccta atgtgaaaga agtcagtgag actcaggaaa caatgaatga actggagtta    4020
ttaacagaac agtccacaac caaggactca acaacactgg caagaatага aatggaaagg    4080 ctcaggttga atgaaaaatt tcaagaaagt caggaagaga taaaatctct aaccaaggaa    4140
agagacaacc ttaaaacgat aaaagaagcc cttgaagtta acatgacca gctgaaagaa    4200 catattagag aaactttggc taaaatccag gagtctcaaa gcaaacaaga acagtcctta    4260
aatatgaaag aaaaagacaa tgaaactacc aaaatcgtga gtgagatgga gcaattcaaa    4320
cccaaagatt cagcactact aaggatagaa atagaaatgc tcggattgtc caaaagactt    4380
caagaaagtc atgatgaaat gaatctgta gctaaggaga aagatgacct acagaggctg    4440
caagaagttc ttcaatctga aagtgaccag ctcaaagaaa acataaaaga aattgtagct    4500
```

```
aaacacctgg aaactgaaga ggaacttaaa gttgctcatt gttgcctgaa agaacaagag    4560
gaaactatta atgagttaag agtgaatctt tcagagaagg aaactgaaat atcaaccatt    4620
caaaagcagt tagaagcaat caatgataaa ttacagaaca agatccaaga gatttatgag    4680
aaagaggaac aatttaatat aaaacaaatt agtgaggttc aggaaaaagt gaatgaactg    4740
aaacaattca aggagcatcg caaagccaag gattcagcac tacaaagtat agaaagtaag    4800
atgctcgagt tgaccaacag acttcaagaa agtcaagaag aaatacaaat tatgattaag    4860 gaaaagagg aaatgaaaag agtacaggag gcccttcaga tagagagaga ccaactgaaa    4920
gaaaacacta agaaaattgt agctaaaatg aaagaatctc aagaaaaaga atatcagttt    4980
cttaagatga cagctgtcaa tgagactcag gagaaaatgt gtgaaataga acacttgaag    5040
gagcaatttg agacccagaa gttaaacctg gaaaacatag aaacggagaa tataaggttg    5100
actcagatac tacatgaaaa ccttgaagaa atgagatctg taacaaaaga aagagatgac    5160
cttaggagtg tggaggagac tctcaaagta gagagagacc agctcaagga aaaccttaga    5220 gaactataa ctagagacct agaaaaacaa gaggagctaa aaattgttca catgcatctg    5280
aaggagcacc aagaaactat tgataaacta agagggattg tttcagagaa aacaaatgaa    5340
atatcaaata tgcaaaagga cttagaacac tcaaatgatg ccttaaaagc acaggatctg    5400
aaaatacaag aggaactaag aattgctcac atgcatctga agagcagca ggaaactatt    5460 gacaaactca gaggaattgt ttctgagaag acagataaac tatcaaatat gcaaaaagat    5520
ttagaaaatt caaatgctaa attacaagaa aagattcaag aacttaaggc aaatgaacat    5580
caacttatta cgttaaaaaa agatgtcaat gagacacaga aaaagtgtc tgaaatggag    5640 caactaaaga aacaaataaa agaccaaagc ttaactctga gtaaattaga aatagagaat    5700
ttaaatttgg ctcagaaact tcatgaaaac cttgaagaaa tgaaatctgt aatgaaagaa    5760
agagataatc taagaagagt agaggagaca ctcaaactgg agagagacca actcaaggaa    5820
agcctgcaag aaaccaaagc tagagatctg gaaatacaac aggaactaaa aactgctcgt    5880
atgctatcaa agaacacaa agaaactgtt gataaactta gagaaaaaat ttcagaaaag    5940
acaattcaaa tttcagacat tcaaaaggat ttagataaat caaagatga attacagaaa    6000 aagatccaag aacttcagaa aaaagaactt caactgctta gagtgaaaga agatgtcaat    6060
atgagtcata aaaaaattaa tgaaatggaa cagttgaaga agcaatttga ggcccaaaac    6120
ttatctatgc aaagtgtgag aatggataac ttccagttga ctaagaaact tcatgaaagc    6180
cttgaagaaa taagaattgt agctaaagaa agagatgagc taaggaggat aaaagaatct    6240
ctcaaaatgg aaagggacca attcatagca accttaaggg aaatgatagc tagagaccga    6300
cagaaccacc aagtaaaacc tgaaaaaagg ttactaagtg atggacaaca gcaccttacg    6360
gaaagcctga gagaaaagtg ctctagaata aaagagcttt tgaagagata ctcagagatg    6420
gatgatcatt atgagtgctt gaatagattg tctcttgact tggagaagga aattgaattc    6480 caaaagagc tttcaatgag agttaaagca aacctctcac ttccctattt acaaaccaaa    6540
cacattgaaa aacttttac tgcaaaccag agatgctcca tggaattcca cagaatcatg    6600
aagaaactga agtatgtgtt aagctatgtt acaaaaataa agaagaaca acatgaatcc    6660 atcaataaat ttgaaatgga ttttattgat gaagtggaaa agcaaaagga attgctaatt    6720
aaaatacagc accttcaaca agattgtgat gtaccatcca gagaattaag ggatctcaaa    6780
ttgaaccaga atatggatct acatattgag gaaattctca aagatttctc agaaagtgag    6840
```

```
ttccctagca taaagactga atttcaacaa gtactaagta ataggaaaga aatgacacag    6900
tttttggaag agtggttaaa tactcgtttt gatatagaaa agcttaaaaa tggcatccag    6960
aaagaaaatg ataggatttg tcaagtgaat aacttcttta ataacagaat aattgccata    7020
atgaatgaat caacagagtt tgaggaaaga agtgctacca tatccaaaga gtgggaacag    7080
gacctgaaat cactgaaaga gaaaatgaaa aactattta aaaactacca aacattgaag     7140
acttccttgg catctggtgc ccaggttaat cctaccacac aagacaataa gaatcctcat    7200
gttacatcaa gagctacaca gttaaccaca gagaaaattc gagagctgga aaattcactg    7260
catgaagcta agaaagtgc tatgcataag gaaagcaaga ttataaagat gcagaaagaa    7320
cttgaggtga ctaatgacat aatagcaaaa cttcaagcca aagttcatga atcaaataaa    7380
tgccttgaaa aaacaaaaga gacaattcaa gtacttcagg acaaagttgc tttaggagct    7440
aagccatata agaagaaat tgaagatctc aaaatgaagc ttgtgaaaat agacctagag    7500
aaaatgaaaa atgccaaaga atttgaaaag gaaatcagtg ctacaaaagc cactgtagaa    7560
tatcaaaagg aagttataag gctattgaga gaaaatctca aagaagtca acaggcccaa    7620
gatacctcag tgatatcaga acatactgat cctcagcctt caaataaacc cttaacttgt    7680
ggaggtggca gcggcattgt acaaaacaca aaagctctta ttttgaaaag tgaacatata    7740
aggctagaaa aagaaatttc taagttaaag cagcaaaatg aacagctaat aaaacaaaag    7800
aatgaattgt taagcaataa tcagcatctt tccaatgagg tcaaaacttg gaaggaaaga    7860
accettaaaa gagaggctca caaacaagta acttgtgaga attctccaaa gtctcctaaa    7920
gtgactggaa cagcttctaa aaagaaacaa attacaccct ctcaatgcaa ggaacggaat    7980
ttacaagatc ctgtgccaaa ggaatcacca aaatcttgtt tttttgatag ccgatcaaag    8040
tctttaccat cacctcatcc agttcgctat tttgataact caagtttagg cctttgtcca    8100
gaggtgcaaa atgcaggagc agagagtgtg gattctcagc caggtccttg gcacgcctcc    8160
tcaggcaagg atgtgcctga gtgcaaaact cagtagactc ctctttgtca cttctctgga    8220
gatccagcat tccttatttg gaaatgactt tgtttatgtg tctatccctg gtaatgatgt    8280
tgtagtgcag cttaatttca attcagtctt tactttgcca ctagagttga aagataaggg    8340
aacaggaaat gaatgcattg tggtaattta gaatggtgat agcaatacct tcttcttgca    8400
tatggtaata cttttaaaag ttgaattgtt ttatttattt gtatattttg taagaataa    8460
agttattgaa agaaatgtaa agttatctac atgacttagc atattccaaa gcataataca    8520
tacattaata taaaacatca ttttattaac aaaattgtaa atgttttaa taccttacac     8580
attcaataaa tgtttagtag ttctgaatca ccaaaaaaaa aaaaaaaaa                 8630
```

<210> SEQ ID NO 3
<211> LENGTH: 504
<212> TYPE: PRT
<213> ORGANISM: Homo sapiens

<400> SEQUENCE: 3

Met Glu Ala Thr Gly Thr Trp Ala Leu Leu Ala Leu Ala Leu Leu
1               5                   10                  15

Leu Leu Leu Thr Leu Ala Leu Ser Gly Thr Arg Ala Arg Gly His Leu
            20                  25                  30

Pro Pro Gly Pro Thr Pro Leu Pro Leu Gly Asn Leu Leu Gln Leu
        35                  40                  45

Arg Pro Gly Ala Leu Tyr Ser Gly Leu Met Arg Leu Ser Lys Lys Tyr
    50                  55                  60

```
Gly Pro Val Phe Thr Ile Tyr Leu Gly Pro Trp Arg Pro Val Val
 65                  70                  75                  80

Leu Val Gly Gln Glu Ala Val Arg Glu Ala Leu Gly Gly Gln Ala Glu
                 85                  90                  95

Glu Phe Ser Gly Arg Gly Thr Val Ala Met Leu Glu Gly Thr Phe Asp
            100                 105                 110

Gly His Gly Val Phe Phe Ser Asn Gly Glu Arg Trp Arg Gln Leu Arg
            115                 120                 125

Lys Phe Thr Met Leu Ala Leu Arg Asp Leu Gly Met Gly Lys Arg Glu
        130                 135                 140

Gly Glu Glu Leu Ile Gln Ala Glu Ala Arg Cys Leu Val Glu Thr Phe
145                 150                 155                 160

Gln Gly Thr Glu Gly Arg Pro Phe Asp Pro Ser Leu Leu Ala Gln
            165                 170                 175

Ala Thr Ser Asn Val Val Cys Ser Leu Leu Phe Gly Leu Arg Phe Ser
            180                 185                 190

Tyr Glu Asp Lys Glu Phe Gln Ala Val Val Arg Ala Ala Gly Gly Thr
        195                 200                 205

Leu Leu Gly Val Ser Ser Gln Gly Gly Gln Thr Tyr Glu Met Phe Ser
210                 215                 220

Trp Phe Leu Arg Pro Leu Pro Gly Pro His Lys Gln Leu Leu His His
225                 230                 235                 240

Val Ser Thr Leu Ala Ala Phe Thr Val Arg Gln Val Gln Gln His Gln
            245                 250                 255

Gly Asn Leu Asp Ala Ser Gly Pro Ala Arg Asp Leu Val Asp Ala Phe
            260                 265                 270

Leu Leu Lys Met Ala Gln Glu Glu Gln Asn Pro Gly Thr Glu Phe Thr
        275                 280                 285

Asn Lys Asn Met Leu Met Thr Val Ile Tyr Leu Leu Phe Ala Gly Thr
290                 295                 300

Met Thr Val Ser Thr Thr Val Gly Tyr Thr Leu Leu Leu Leu Met Lys
305                 310                 315                 320

Tyr Pro His Val Gln Lys Trp Val Arg Glu Leu Asn Arg Glu Leu
            325                 330                 335

Gly Ala Gly Gln Ala Pro Ser Leu Gly Asp Arg Thr Arg Leu Pro Tyr
            340                 345                 350

Thr Asp Ala Val Leu His Glu Ala Gln Arg Leu Leu Ala Leu Val Pro
        355                 360                 365

Met Gly Ile Pro Arg Thr Leu Met Arg Thr Thr Arg Phe Arg Gly Tyr
        370                 375                 380

Thr Leu Pro Gln Gly Thr Glu Val Phe Pro Leu Leu Gly Ser Ile Leu
385                 390                 395                 400

His Asp Pro Asn Ile Phe Lys His Pro Glu Glu Phe Asn Pro Asp Arg
            405                 410                 415

Phe Leu Asp Ala Asp Gly Arg Phe Arg Lys His Glu Ala Phe Leu Pro
            420                 425                 430

Phe Ser Leu Gly Lys Arg Val Cys Leu Gly Glu Gly Leu Ala Lys Ala
        435                 440                 445

Glu Leu Phe Leu Phe Phe Thr Thr Ile Leu Gln Ala Phe Ser Leu Glu
        450                 455                 460

Ser Pro Cys Pro Pro Asp Thr Leu Ser Leu Lys Pro Thr Val Ser Gly
465                 470                 475                 480
```

```
Leu Phe Asn Ile Pro Pro Ala Phe Gln Leu Gln Val Arg Pro Thr Asp
            485                 490                 495

Leu His Ser Thr Thr Gln Thr Arg
            500

<210> SEQ ID NO 4
<211> LENGTH: 2660
<212> TYPE: DNA
<213> ORGANISM: Homo sapiens

<400> SEQUENCE: 4
cctaactagc ccagccgcgc ggagcgcctg ggagaggaga aggagccgac ctgccgagat      60
ggaggcgacc ggcacctggg cgctgctgct ggcgctggcg ctgctcctgc tgctgacgct     120
ggcgctgtcc gggaccaggg cccgaggcca cctgccccc gggcccacgc cgctaccact     180
gctgggaaac ctcctgcagc tacggcccgg ggcgctgtat tcagggctca tgcggctgag     240
taagaagtac ggaccggtgt tcaccatcta cctgggaccc tggcggcctg tggtggtcct     300
ggttgggcag gaggctgtgc gggaggccct gggaggtcag gctgaggagt tcagcggccg     360
gggaaccgta gcgatgctgg aagggacttt tgatggccat ggggttttct tctccaacgg     420
ggagcggtgg aggcagctga ggaagtttac catgcttgct ctgcgggacc tgggcatggg     480
gaagcgagaa ggcgaggagc tgatccaggc ggaggcccgg tgtctggtgg agacattcca     540
ggggacagaa ggacgcccat tcgatccctc cctgctgctg gcccaggcca cctcaacgt     600 agtctgctcc ctcctctttg gcctccgctt ctcctatgag gataaggagt tccaggccgt     660
ggtccgggca gctggtggta ccctgctggg agtcagctcc caggggggtc agacctacga     720
gatgttctcc tggttcctgc ggcccctgcc aggcccccac aagcagctcc tccaccacgt     780
cagcaccttg gctgccttca cagtccggca ggtgcagcag caccagggga acctggatgc     840
ttcgggcccc gcacgtgacc ttgtcgatgc cttcctgctg aagatggcac aggaggaaca     900
aaacccaggc acagaattca ccaacaagaa catgctgatg acagtcattt atttgctgtt     960
tgctgggacg atgacggtca gcaccacggt cggctatacc ctcctgctcc tgatgaaata    1020
ccctcatgtc caaaagtggg tacgtgagga gctgaatcgg gagctggggg ctggccaggc    1080
accaagccta ggggaccgta cccgcctccc ttacaccgac gcggttctgc atgaggcgca    1140
gcggctgctg gcgctggtgc ccatgggaat accccgcacc ctcatgcgga ccaccccgctt   1200 ccgagggtac accctgcccc agggcacgga ggtcttcccc ctccttggct ccatcctgca    1260
tgaccccaac atcttcaagc cccagaaga gttcaaccca gaccgtttcc tggatgcaga    1320
tggacggttc aggaagcatg aggcgttcct gccctctcc ttagggaagc gtgtctgcct    1380
tggagagggc ctggcaaaag cggagctctt cctcttcttc accaccatcc tacaagcctt    1440
ctccctggag agcccgtgcc cgccggacac cctgagcctc aagcccaccg tcagtggcct    1500
tttcaacatt cccccagcct tccagctgca agtccgtccc actgaccttc actccaccac    1560
gcagaccaga tgaaggaagg caacttggaa gtggtgggtg cccaggacgg tgcctccagc    1620
ctcaacagtg ggcatggaca gggttaatgt ctccagagtg tacactgcag gcagccacat    1680
ttacacgcct gcagttgttt tccggagtct gtccccgggc cacacgctc acttgactca    1740 tgctgctaag atgcacaacc gcacacccat acacaactac aagggccaca aagcaactgc    1800
tgggttagct ttccacagac ataaatatag tccatctgca atcacaagca catagccagg    1860
taacccacca actcccctgg atctgcagcc cacacgtggg agtctggctg tcaccttcac    1920
aagccacaga aacggccaca catgttcaca gctcacacgc cctctccatt catcgaactt    1980
```

```
ctcagtgtcc ctgtccctgg tgcctggcac agggaacagc atgccccctc cggggtcatg    2040
ccacccagag actgtcgctg tctatggccc caactcatgc tccctctctt ggctacacca    2100
ctctcccagc ctgtgaccac cgatgtccac acacccccaa ccacttgtcc acacagctac    2160
ccacgtacga catcgtcctg ctccccaga gtatcttccc actgagacac gccgccccca    2220
cagaggcaca gtccccagcc acctctgcaa ctgcagccct cagtcacccc tttttaagca    2280
ccctgattct accaaatgca aacacatctg ggtctgcgat tatgcacaga gactttggac    2340
atacgaggac cctcagaccg gaggaacacc tgcccaaccc caacacgtgc ttatgtaacc    2400
acgtggaaag cggcccctgc tgcccctcca cacacacata cactcact gatctacagc      2460 ccctgttcgg cgtcagagtc cccactagac ccagtggaag gggttagaga ccaagtaggg    2520 gccagttttcc aattcaccct gtcagggagt gagccggatc tgacgttcct tgtgacttaa   2580
gggtccggct tgggaattaa agtttgtttc tggcctttag cctaaaaaaa aaaaaaaaaa    2640
aaaaaaaaaa aaaaaaaaaa                                                2660

<210> SEQ ID NO 5
<211> LENGTH: 257
<212> TYPE: PRT
<213> ORGANISM: Homo sapiens

<400> SEQUENCE: 5

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Phe Phe Ile
        195                 200                 205

Pro Leu Leu Val Val Ile Leu Phe Ala Val Asp Thr Gly Leu Phe Ile
    210                 215                 220

Ser Thr Gln Gln Gln Val Thr Phe Leu Leu Lys Ile Lys Arg Thr Arg
225                 230                 235                 240

Lys Gly Phe Arg Leu Leu Asn Pro His Pro Lys Pro Asn Pro Lys Asn
```

Asn

<210> SEQ ID NO 6
<211> LENGTH: 1198
<212> TYPE: DNA
<213> ORGANISM: Homo sapiens

<400> SEQUENCE: 6

```
tactaagagt ctccagcatc ctccacctgt ctaccaccga gcatgggcct atatttgaag      60
ccttagatct ctccagcaca gtaagcacca ggagtccatg aagaagatgg ctcctgccat     120
ggaatcccct actctactgt gtgtagcctt actgttcttc gctccagatg gcgtgttagc     180
agtccctcag aaacctaagg tctccttgaa ccctccatgg aatagaatat ttaaaggaga     240
gaatgtgact cttacatgta atgggaacaa tttctttgaa gtcagttcca ccaaatggtt     300
ccacaatggc agcctttcag aagagacaaa ttcaagtttg aatattgtga atgccaaatt     360
tgaagacagt ggagaataca atgtcagca ccaacaagtt aatgagagtg aacctgtgta     420
cctggaagtc ttcagtgact ggctgctcct tcaggcctct gctgaggtgg tgatggaggg     480
ccagcccctc ttcctcaggt gccatggttg gaggaactgg gatgtgtaca aggtgatcta     540
ttataaggat ggtgaagctc tcaagtactg gtatgagaac cacaacatct ccattacaaa     600
tgccacagtt gaagacagtg gaacctacta ctgtacgggc aaagtgtggc agctggacta     660
tgagtctgag cccctcaaca ttactgtaat aaaagctccg cgtgagaagt actggctaca     720
attttttatc ccattgttgg tggtgattct gtttgctgtg acacaggat tatttatctc     780
aactcagcag caggtcacat ttctcttgaa gattaagaga accaggaaag gcttcagact     840
tctgaaccca catcctaagc caaaccccaa aacaactga taataattact caagaaatat     900
ttgcaacatt agtttttttc cagcatcagc aattgctact caattgtcaa acacagcttg     960
caatatacat agaaacgtct gtgctcaagg atttatagaa atgcttcatt aaactgagtg    1020
aaactggtta agtggcatgt aatagtaagt gctcaattaa cattggttga ataaatgaga    1080
gaatgaatag attcatttat tagcatttgt aaaagagatg ttcaatttca ataaataaa    1140
tataaaacca tgtaacagaa tgcttctgag taaaaaaaaa aaaaaaaaa aaaaaaaa     1198
```

<210> SEQ ID NO 7
<211> LENGTH: 177
<212> TYPE: PRT
<213> ORGANISM: Homo sapiens

<400> SEQUENCE: 7

```
Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
```

|   |   |   | 100 |   |   | 105 |   |   |   | 110 |   |   |
|---|---|---|---|---|---|---|---|---|---|---|---|---|

Leu Ser Glu Asn Arg Lys Gln Asp Lys Arg Phe Ala Phe Ile Arg Ser
        115               120             125

Asp Ser Gly Pro Thr Thr Ser Phe Glu Ser Ala Ala Cys Pro Gly Trp
  130               135              140

Phe Leu Cys Thr Ala Met Glu Ala Asp Gln Pro Val Ser Leu Thr Asn
145             150              155             160

Met Pro Asp Glu Gly Val Met Val Thr Lys Phe Tyr Phe Gln Glu Asp
         165              170            175

Glu

<210> SEQ ID NO 8
<211> LENGTH: 1794
<212> TYPE: DNA
<213> ORGANISM: Homo sapiens

<400> SEQUENCE: 8

```
atttctttat aaaccacaac tctgggcccg caatggcagt ccactgcctt gctgcagtca    60
cagaatggaa atctgcagag gcctccgcag tcacctaatc actctcctcc tcttcctgtt   120
ccattcagag acgatctgcc gaccctctgg gagaaaatcc agcaagatgc aagccttcag   180
aatctgggat gttaaccaga agaccttcta tctgaggaac aaccaactag ttgctggata   240
cttgcaagga ccaaatgtca atttagaaga aagatagat gtggtaccca ttgagcctca   300
tgctctgttc ttgggaatcc atggagggaa gatgtgcctg tcctgtgtca agtctggtga   360
tgagaccaga ctccagctgg aggcagttaa catcactgac ctgagcgaga acagaaagca   420
ggacaagcgc ttcgccttca tccgctcaga cagtggcccc accaccagtt ttgagtctgc   480
cgcctgcccc ggttggttcc tctgcacagc gatggaagct gaccagcccg tcagcctcac   540
caatatgcct gacgaaggcg tcatggtcac caaattctac ttccaggagg acgagtagta   600
ctgcccaggc ctgcctgttc ccattcttgc atggcaagga ctgcagggac tgccagtccc   660
cctgccccag ggctcccggc tatggggca ctgaggacca gccattgagg ggtggaccct   720
cagaaggcgt cacaacaacc tggtcacagg actctgcctc ctcttcaact gaccagcctc   780
catgctgcct ccagaatggt cttttctaatg tgtgaatcag agcacagcag ccctgcaca   840
aagcccttcc atgtcgcctc tgcattcagg atcaaacccc gaccacctgc caacctgct   900
ctcctcttgc cactgcctct cctccctca ttccaccttc ccatgccctg gatccatcag   960
gccacttgat gaccccaac caagtggctc ccacaccctg ttttacaaaa aagaaaagac  1020
cagtccatga gggaggtttt taagggtttg tggaaaatga aaattaggat ttcatgattt  1080
ttttttttca gtccccgtga aggagagccc ttcatttgga gattatgttc tttcggggag  1140
aggctgagga cttaaaatat tcctgcattt gtgaaatgat ggtgaaagta agtggtagct  1200
tttcccttct ttttcttctt ttttgtgat gtcccaactt gtaaaaatta aaagttatgg  1260
tactatgtta gccccataat ttttttttc cttttaaaac acttccataa tctgactcc  1320
tctgtccagg cactgctgcc cagcctccaa gctccatctc cactccagat tttttacagc  1380
tgcctgcagt actttaccctc ctatcagaag tttctcagct cccaaggctc tgagcaaatg  1440
tggctcctgg gggttctttc ttcctctgct gaaggaataa attgctcctt gacattgtag  1500
agcttctggc acttggagac ttgtatgaaa gatggctgtg cctctgcctg tctccccac  1560
cgggctggga gctctgcaga gcaggaaaca tgactcgtat atgtctcagg tccctgcagg  1620
gccaagcacc tagcctcgct cttggcaggt actcagcgaa tgaatgctgt atatgttggg  1680
```

```
                                                           -continued tgcaaagttc cctacttcct gtgacttcag ctctgtttta caataaaatc ttgaaaatgc   1740
ctaaaaaaaa aaaaaaaaaa aaaaaaaaaa aaaaaaaaaa aaaaaaaaaa aaaa         1794
```

<210> SEQ ID NO 9
<211> LENGTH: 350
<212> TYPE: PRT
<213> ORGANISM: Homo sapiens

<400> SEQUENCE: 9

```
Met Ala Ala Thr Ser Leu Met Ser Ala Leu Ala Ala Arg Leu Leu Gln
1               5                   10                  15

Pro Ala His Ser Cys Ser Leu Arg Leu Arg Pro Phe His Leu Ala Ala
            20                  25                  30

Val Arg Asn Glu Ala Val Val Ile Ser Gly Arg Lys Leu Ala Gln Gln
        35                  40                  45

Ile Lys Gln Glu Val Arg Gln Glu Val Glu Glu Trp Val Ala Ser Gly
50                  55                  60

Asn Lys Arg Pro His Leu Ser Val Ile Leu Val Gly Glu Asn Pro Ala
65                  70                  75                  80

Ser His Ser Tyr Val Leu Asn Lys Thr Arg Ala Ala Val Val Gly
                85                  90                  95

Ile Asn Ser Glu Thr Ile Met Lys Pro Ala Ser Ile Ser Glu Glu Glu
            100                 105                 110

Leu Leu Asn Leu Ile Asn Lys Leu Asn Asn Asp Asp Asn Val Asp Gly
        115                 120                 125

Leu Leu Val Gln Leu Pro Leu Pro Glu His Ile Asp Glu Arg Arg Ile
130                 135                 140

Cys Asn Ala Val Ser Pro Asp Lys Asp Val Asp Gly Phe His Val Ile
145                 150                 155                 160

Asn Val Gly Arg Met Cys Leu Asp Gln Tyr Ser Met Leu Pro Ala Thr
                165                 170                 175

Pro Trp Gly Val Trp Glu Ile Ile Lys Arg Thr Gly Ile Pro Thr Leu
            180                 185                 190

Gly Lys Asn Val Val Ala Gly Arg Ser Lys Asn Val Gly Met Pro
        195                 200                 205

Ile Ala Met Leu Leu His Thr Asp Gly Ala His Glu Arg Pro Gly Gly
210                 215                 220

Asp Ala Thr Val Thr Ile Ser His Arg Tyr Thr Pro Lys Glu Gln Leu
225                 230                 235                 240

Lys Lys His Thr Ile Leu Ala Asp Ile Val Ile Ser Ala Ala Gly Ile
                245                 250                 255

Pro Asn Leu Ile Thr Ala Asp Met Ile Lys Glu Gly Ala Ala Val Ile
            260                 265                 270

Asp Val Gly Ile Asn Arg Val His Asp Pro Val Thr Ala Lys Pro Lys
        275                 280                 285

Leu Val Gly Asp Val Asp Phe Glu Gly Val Arg Gln Lys Ala Gly Tyr
290                 295                 300

Ile Thr Pro Val Pro Gly Gly Val Gly Pro Met Thr Val Ala Met Leu
305                 310                 315                 320

Met Lys Asn Thr Ile Ile Ala Ala Lys Lys Val Leu Arg Leu Glu Glu
                325                 330                 335

Arg Glu Val Leu Lys Ser Lys Glu Leu Gly Val Ala Thr Asn
            340                 345                 350
```

<210> SEQ ID NO 10
<211> LENGTH: 2208
<212> TYPE: DNA
<213> ORGANISM: Homo sapiens

<400> SEQUENCE: 10

```
ggggcctgcc acgaggccgc agtataaccg cgtggcccgc gcgcgcgctt ccctcccggc      60
gcagtcaccg gcgcggtcta tggctgcgac ttctctaatg tctgctttgg ctgcccggct     120
gctgcagccc gcgcacagct gctcccttcg ccttcgccct ttccacctcg cggcagttcg     180
aaatgaagct gttgtcattt ctggaaggaa actggcccag cagatcaagc aggaagtgcg     240
gcaggaggta gaagagtggg tggcctcagg caacaaacgg ccacacctga gtgtgatcct     300
ggttggcgag aatcctgcaa gtcactccta tgtcctcaac aaaaccaggg cagctgcagt     360
tgtgggaatc aacagtgaga caattatgaa accagcttca atttcagagg aagaattgtt     420
gaatttaatc aataaactga ataatgatga taatgtagat ggcctccttg ttcagttgcc     480
tcttccagag catattgatg agagaaggat ctgcaatgct gtttctccag acaaggatgt     540
tgatggcttt catgtaatta atgtaggacg aatgtgtttg gatcagtatt ccatgttacc     600
ggctactcca tggggtgtgt gggaataat caagcgaact ggcattccaa ccctagggaa     660
gaatgtggtt gtggctggaa ggtcaaaaaa cgttggaatg cccattgcaa tgttactgca     720
cacagatggg gcgcatgaac gtcccggagg tgatgccact gttacaatat ctcatcgata     780
tactcccaaa gagcagttga agaaacatac aattcttgca gatattgtaa tatctgctgc     840
aggtattcca aatctgatca cagcagatat gatcaaggaa ggagcagcag tcattgatgt     900
gggaataaat agagttcacg atcctgtaac tgccaaaccc aagttggttg agatgtggga     960
ttttgaagga gtcagacaaa aagctgggta tcactccca gttcctggag tgttggccc    1020
catgacagtg gcaatgctaa tgaagaatac cattattgct gcaaaaaagg tgctgaggct    1080
tgaagagcga gaagtgctga gtctaaaga gcttggggta gccactaatt aactactgtg    1140
tcttctgtgt cacaaacagc actccaggcc agctcaagaa gcaaagcagg ccaatagaaa    1200
tgcaatattt ttaatttatt ctactgaaat ggtttaaaat gatgccttgt atttattgaa    1260
agcttaaatg ggtgggtgtt tctgcacata cctctgcagt acctcaccag ggagcattcc    1320
agtatcatgc agggtcctgt gatctagcca ggagcagcca ttaacctagt gattaatatg    1380
ggagacatta ccatatggag gatggatgct tcactttgtc aagcacctca gttacacatt    1440
cgccttttct aggattgcat ttcccaagtg ctattgcaat aacagttgat actcattta    1500
ggtaccaaac cttttgagtt caactgatca aaccaaagga aaagtgttgc tagagaaaat    1560
tagggaaaag gtgaaaaaga aaaatggta gtaattgagc agaaaaaaat taatttatat    1620
atgtattgat tggcaaccag atttatctaa gtagaactga attggctagg aaaaaagaaa    1680
aactgcatgt taatcatttt cctaagctgt cctttgagg cttagtcagt ttattgggaa    1740
aatgtttagg attattcctt gctattagta ctcattttat gtatgttacc cttcagtaag    1800
ttctccccat tttagttttc taggactgaa aggattcttt tctacattat acatgtgtgt    1860
tgtcatattt ggcttttgct atatacttta acttcattgt taaattttg tattgtatag    1920
tttctttggt gtatcttaaa acctattttt gaaaaacaaa cttggcttga taatcatttg    1980
ggcagcttgg gtaagtacgc aacttacttt tccaccaaag aactgtcagc agctgcctgc    2040
ttttctgtga tgtatgtatc ctgttgactt ttccagaaat ttttttaagag tttgagttac    2100
tattgaattt aatcagactt tctgattaaa gggttttctt tctttttttaa taaaacacat    2160
```

```
ctgtctggta tggtatgaat ttctgaaaaa aaaaaaaaaa aaaaaaaa                    2208
```

<210> SEQ ID NO 11
<211> LENGTH: 287
<212> TYPE: PRT
<213> ORGANISM: Homo sapiens

<400> SEQUENCE: 11

```
Glu Arg Cys Cys Arg Cys Cys Arg Cys Pro Cys Cys Gly Gln Gly
1               5                   10                  15

Pro Arg Ser Gly Cys Lys Ile Pro Ala Gly Asp Ala Arg Val Arg Asp
            20                  25                  30

Gly Ala Gly Gly Ser Val His Leu Cys Ala Leu Phe Gly Leu Leu Pro
        35                  40                  45

Arg Val Trp Leu Glu Arg Phe Tyr Pro Cys Leu Trp Pro Leu Val Pro
    50                  55                  60

Gly Lys Gly Gln Cys Arg Pro Gly Asp Ser Met Ala Thr Asn Asn Ser
65                  70                  75                  80

Thr Gln Lys Val Gln Lys Glu Thr Gln Gly Arg Phe His Leu Leu Gly
                85                  90                  95

Asp Pro Ser Arg Asn Asn Cys Ser Leu Ser Ile Arg Asp Ala Arg Arg
            100                 105                 110

Arg Asp Asn Gly Ser Tyr Phe Phe Trp Val Ala Arg Arg Thr Lys
        115                 120                 125

Phe Ser Tyr Lys Tyr Ser Pro Leu Ser Val Tyr Val Thr Ala Leu Thr
    130                 135                 140

His Arg Pro Asp Ile Leu Ile Pro Glu Phe Leu Lys Ser Gly His Pro
145                 150                 155                 160

Ser Asn Leu Thr Cys Ser Val Pro Trp Val Cys Glu Gln Gly Thr Pro
                165                 170                 175

Pro Ile Phe Ser Trp Met Ser Ala Ala Pro Thr Ser Leu Gly Pro Arg
            180                 185                 190

Thr Leu His Ser Ser Glu Leu Thr Ile Ile Pro Arg Pro Gln Asp His
        195                 200                 205

Gly Thr Asn Leu Ile Cys Gln Val Thr Phe Pro Gly Ala Gly Val Thr
    210                 215                 220

Thr Glu Arg Thr Ile Gln Leu Ser Val Ser Trp Lys Ser Gly Thr Val
225                 230                 235                 240

Glu Glu Val Val Val Leu Ala Val Gly Val Ala Val Lys Ile Leu
                245                 250                 255

Leu Leu Cys Leu Cys Leu Ile Ile Leu Ser Phe His Lys Lys Lys Ala
            260                 265                 270

Val Arg Ala Val Glu Val Glu Glu Asn Val Tyr Ala Val Met Gly
        275                 280                 285
```

<210> SEQ ID NO 12
<211> LENGTH: 2251
<212> TYPE: DNA
<213> ORGANISM: Homo sapiens

<400> SEQUENCE: 12

```
ccaagatctc atgctcctcc ccacagccct cttctctgct cacacaggaa gcccaggaag    60
cctctgcctc agagatgctg ccgctgctgc tgccgctgcc cctgtgtggg cagggcccct   120
cgctcaggat gcaagattcc ggctggagat gccagagtcc gtgacggtgc aggagggtct   180
```

| | |
|---|---|
| gtgcatcttt gtgcactgtt cggtcttcta cctcgagtat ggctggaaag attctacccc | 240 |
| tgcttatggc cactggttcc gggaaggggt cagtgtagac caggagactc cagtggccac | 300 |
| aaacaactca actcaaaaag tgcagaagga gacccagggc cgattccacc tcctcggtga | 360 |
| tccctcaagg aacaactgct ccctgagcat cagagacgcc aggaggaggg acaacggttc | 420 |
| atacttcttt tgggtggcga gaggaagaac aaaatttagt tacaaatatt ccccgctctc | 480 |
| tgtgtatgtg acagccctga cccacaggcc cgacatcctc atcccggagt tcctaaagtc | 540 |
| tggccatccc agcaacctga cctgctctgt gccctgggtc tgtgagcagg aacaccccc | 600 |
| catcttctcc tggatgtcag ctgccccccac ctccctgggc cccaggaccc tccactcctc | 660 |
| agtgctcacg atcatcccac ggcctcagga ccacggcacc aacctcatct gtcaggtgac | 720 |
| gttccccgga gctggtgtga ccacggagag aaccatccag ctcagtgtct cctggaaatc | 780 |
| aggaaccgtg gaagaggtgg ttgttttggc cgtgggggta gtggctgtga agatcctgct | 840 |
| tctctgcctt tgcctcatca tcctcaggta agcactgcct gaagaccaag gacaggcatg | 900 |
| gggagggcag aggacatgat gctgaatccc agaatctcaa tcctgggggt atgcagacag | 960 |
| tttacgtggt cctggggcca ggctggaggc tgaattggtg gtgagaatta cacatgggcc | 1020 |
| atttgtggtc agtttgtgtc tgtcccaact gagggccaaa tgccaggatg gggagcttcc | 1080 |
| tgttgtcatc aaggaagtct agacctgctc ttcctccctg tgatccctcc agcctctagc | 1140 |
| agggcacagaa agttgagtt ggctgccctt tgctcccttc atgtggccac acttacaggt | 1200 |
| ccttgtctct tcactcaatg tcagtttcca caagaagaag gcggtgaggg cagtggaggt | 1260 |
| tgaggagaat gtatatgctg tcatgggtta atctctcagg tgagtgatgt gggcctctca | 1320 |
| ctcttcaaca tcctgctgga taactcctcc acaatggcct ccaggattgc tctgcccatc | 1380 |
| atggccaaag ttaagccaac tgtcttcctc ctcaaaccta cttttcctgg gatgtgggtt | 1440 |
| cttcatcctg cagatgacaa agaggcctca tctctaaagt cagaacctgg gtgtgggtct | 1500 |
| ccatcttgac ccccctccct tctctagatc ccataaatta ctagctcttg tccctccttc | 1560 |
| tcctaagcag ggctcatctt gatgccctt tctccatcct gaccctggtc attcttgcgg | 1620 |
| cctcacctct tccctgatca ctgaacccct ttcacctcct gcctccatct ctccccaaca | 1680 |
| caggcctcca gactgtactt ccagatgtct cctcatccag ttcctccaca gtctgaatgg | 1740 |
| ccatgttttcc tcttcattgc tggagaatga agtgcaaatg ccactgcctg gactgaaggc | 1800 |
| ctttcacgat ctgtcttctg ctggactctg ctcctgatcc cccttctcct tgcatcaccc | 1860 |
| gaagtctccc tacacccacc aggccaagcc ctctgtgatt ctgagacttt gcatgtgtag | 1920 |
| ttacttctcc tgaaatggcc ttcctcccca ttcctgccaa tccaggtcct tatcatcctt | 1980 |
| caggttgtct taaatgtcat ccaggtgtgt gtattttat gtaatccttg tatgatatta | 2040 |
| agcggagatg tggcatttgt tcattaattt gtagacatat tcagtaacca tactgaatac | 2100 |
| atataatgac tatgtgccag catttccgta tgtgcagaag ttcatcaata gatatagact | 2160 |
| caaagagctc tgtcatcaag ctgttgttct gaagagcaga aggatacaaa taaaaagaaa | 2220 |
| taagtaaaat aaaaaaaaaa aaaaaaaaaa a | 2251 |

<210> SEQ ID NO 13
<211> LENGTH: 790
<212> TYPE: PRT
<213> ORGANISM: Homo sapiens

<400> SEQUENCE: 13

Met Ala Glu Gln Val Leu Pro Gln Ala Leu Tyr Leu Ser Asn Met Arg

```
1               5                   10                  15
Lys Ala Val Lys Ile Arg Glu Arg Thr Pro Glu Asp Ile Phe Lys Pro
                20                  25                  30
Thr Asn Gly Ile Ile His His Phe Lys Thr Met His Arg Tyr Thr Leu
            35                  40                  45
Glu Met Phe Arg Thr Cys Gln Phe Cys Pro Gln Phe Arg Glu Ile Ile
        50                  55                  60
His Lys Ala Leu Ile Asp Arg Asn Ile Gln Ala Thr Leu Glu Ser Gln
65                  70                  75                  80
Lys Lys Leu Asn Trp Cys Arg Glu Val Arg Lys Leu Val Ala Leu Lys
                85                  90                  95
Thr Asn Gly Asp Gly Asn Cys Leu Met His Ala Thr Ser Gln Tyr Met
            100                 105                 110
Trp Gly Val Gln Asp Thr Asp Leu Val Leu Arg Lys Ala Leu Phe Ser
        115                 120                 125
Thr Leu Lys Glu Thr Asp Thr Arg Asn Phe Lys Phe Arg Trp Gln Leu
    130                 135                 140
Glu Ser Leu Lys Ser Gln Glu Phe Val Glu Thr Gly Leu Cys Tyr Asp
145                 150                 155                 160
Thr Arg Asn Trp Asn Asp Glu Trp Asp Asn Leu Ile Lys Met Ala Ser
                165                 170                 175
Thr Asp Thr Pro Met Ala Arg Ser Gly Leu Gln Tyr Asn Ser Leu Glu
            180                 185                 190
Glu Ile His Ile Phe Val Leu Cys Asn Ile Leu Arg Arg Pro Ile Ile
        195                 200                 205
Val Ile Ser Asp Lys Met Leu Arg Ser Leu Glu Ser Gly Ser Asn Phe
    210                 215                 220
Ala Pro Leu Lys Val Gly Gly Ile Tyr Leu Pro Leu His Trp Pro Ala
225                 230                 235                 240
Gln Glu Cys Tyr Arg Tyr Pro Ile Val Leu Gly Tyr Asp Ser His His
                245                 250                 255
Phe Val Pro Leu Val Thr Leu Lys Asp Ser Gly Pro Glu Ile Arg Ala
            260                 265                 270
Val Pro Leu Val Asn Arg Asp Arg Gly Arg Phe Glu Asp Leu Lys Val
        275                 280                 285
His Phe Leu Thr Asp Pro Glu Asn Glu Met Lys Glu Lys Leu Leu Lys
    290                 295                 300
Glu Tyr Leu Met Val Ile Glu Ile Pro Val Gln Gly Trp Asp His Gly
305                 310                 315                 320
Thr Thr His Leu Ile Asn Ala Ala Lys Leu Asp Glu Ala Asn Leu Pro
                325                 330                 335
Lys Glu Ile Asn Leu Val Asp Asp Tyr Phe Glu Leu Val Gln His Glu
            340                 345                 350
Tyr Lys Lys Trp Gln Glu Asn Ser Glu Gln Gly Arg Arg Glu Gly His
        355                 360                 365
Ala Gln Asn Pro Met Glu Pro Ser Val Pro Gln Leu Ser Leu Met Asp
    370                 375                 380
Val Lys Cys Glu Thr Pro Asn Cys Pro Phe Phe Met Ser Val Asn Thr
385                 390                 395                 400
Gln Pro Leu Cys His Glu Cys Ser Glu Arg Arg Gln Lys Asn Gln Asn
                405                 410                 415
Lys Leu Pro Lys Leu Asn Ser Lys Pro Gly Pro Glu Gly Leu Pro Gly
            420                 425                 430
```

```
Met Ala Leu Gly Ala Ser Arg Gly Glu Ala Tyr Glu Pro Leu Ala Trp
        435                 440                 445

Asn Pro Glu Glu Ser Thr Gly Gly Pro His Ser Ala Pro Pro Thr Ala
    450                 455                 460

Pro Ser Pro Phe Leu Phe Ser Glu Thr Thr Ala Met Lys Cys Arg Ser
465                 470                 475                 480

Pro Gly Cys Pro Phe Thr Leu Asn Val Gln His Asn Gly Phe Cys Glu
                485                 490                 495

Arg Cys His Asn Ala Arg Gln Leu His Ala Ser His Ala Pro Asp His
                500                 505                 510

Thr Arg His Leu Asp Pro Gly Lys Cys Gln Ala Cys Leu Gln Asp Val
        515                 520                 525

Thr Arg Thr Phe Asn Gly Ile Cys Ser Thr Cys Phe Lys Arg Thr Thr
    530                 535                 540

Ala Glu Ala Ser Ser Ser Leu Ser Thr Ser Leu Pro Pro Ser Cys His
545                 550                 555                 560

Gln Arg Ser Lys Ser Asp Pro Ser Arg Leu Val Arg Ser Pro Ser Pro
                565                 570                 575

His Ser Cys His Arg Ala Gly Asn Asp Ala Pro Ala Gly Cys Leu Ser
                580                 585                 590

Gln Ala Ala Arg Thr Pro Gly Asp Arg Thr Gly Thr Ser Lys Cys Arg
        595                 600                 605

Lys Ala Gly Cys Val Tyr Phe Gly Thr Pro Glu Asn Lys Gly Phe Cys
    610                 615                 620

Thr Leu Cys Phe Ile Glu Tyr Arg Glu Asn Lys His Phe Ala Ala Ala
625                 630                 635                 640

Ser Gly Lys Val Ser Pro Thr Ala Ser Arg Phe Gln Asn Thr Ile Pro
                645                 650                 655

Cys Leu Gly Arg Glu Cys Gly Thr Leu Gly Ser Thr Met Phe Glu Gly
                660                 665                 670

Tyr Cys Gln Lys Cys Phe Ile Glu Ala Gln Asn Gln Arg Phe His Glu
        675                 680                 685

Ala Lys Arg Thr Glu Glu Gln Leu Arg Ser Ser Gln Arg Asp Val
    690                 695                 700

Pro Arg Thr Thr Gln Ser Thr Ser Arg Pro Lys Cys Ala Arg Ala Ser
705                 710                 715                 720

Cys Lys Asn Ile Leu Ala Cys Arg Ser Glu Glu Leu Cys Met Glu Cys
                725                 730                 735

Gln His Pro Asn Gln Arg Met Gly Pro Gly Ala His Arg Gly Glu Pro
                740                 745                 750

Ala Pro Glu Asp Pro Pro Lys Gln Arg Cys Arg Ala Pro Ala Cys Asp
        755                 760                 765

His Phe Gly Asn Ala Lys Cys Asn Gly Tyr Cys Asn Glu Cys Phe Gln
    770                 775                 780

Phe Lys Gln Met Tyr Gly
785                 790

<210> SEQ ID NO 14
<211> LENGTH: 4705
<212> TYPE: DNA
<213> ORGANISM: Homo sapiens

<400> SEQUENCE: 14
ctttggaaag tcccgtggaa atccccgggc ctacaacccg catacaactg aaacggggca    60
```

```
aagcagactg cgcagtctgc agtcttcgtg gcgggccaag cgagcttgga gcccgcgggg      120
gcggagcggt gagagcggcc gccaagagag atcacacccc cagccgaccc tgccagcgag      180
cgagcccgac cccaggcgtc catggagcgt cgcctccgcc cggtccctgc cccgaccccc      240
gcctgcggcg cgctcctgcc ttgaccagga cttgggactt tgcgaaagga tcgcggggcc      300
cggagaggtg ttggagagca caatggctga acaagtcctt cctcaggctt tgtatttgag      360
caatatgcgg aaagctgtga agatacggga gagaactcca gaagacattt ttaaacctac      420
taatgggatc attcatcatt ttaaaaccat gcaccgatac acactggaaa tgttcagaac      480
ttgccagttt tgtcctcagt ttcgggagat catccacaaa gccctcatcg acagaaacat      540
ccaggccacc ctggaaagcc agaagaaact caactggtgt cgagaagtcc ggaagcttgt      600
ggcgctgaaa acgaacggtg acggcaattg cctcatgcat gccacttctc agtacatgtg      660
gggcgttcag gacacagact tggtactgag gaaggcgctg ttcagcacgc tcaaggaaac      720
agacacacgc aactttaaat tccgctggca actggagtct ctcaaatctc aggaatttgt      780
tgaaacgggg ctttgctatg atactcggaa ctggaatgat gaatgggaca atcttatcaa      840
aatggcttcc acagacacac ccatggcccg aagtggactt cagtacaact cactggaaga      900
aatacacata tttgtccttt gcaacatcct cagaaggcca atcattgtca tttcagacaa      960
aatgctaaga agtttggaat caggttccaa tttcgcccct ttgaaagtgg gtggaattta     1020
cttgcctctc cactggcctg cccaggaatg ctacagatac cccattgttc tcggctatga     1080
cagccatcat tttgtaccct tggtgaccct gaaggacagt gggcctgaaa tccgagctgt     1140
tccacttgtt aacagagacc ggggaagatt tgaagactta aaagttcact tttgacaga      1200 tcctgaaaat gagatgaagg agaagctctt aaaagagtac ttaatggtga tagaaatccc     1260
cgtccaaggc tgggaccatg gcacaactca tctcatcaat gccgcaaagt ggatgaagc      1320 taacttacca aaagaaatca atctggtaga tgattacttt gaacttgttc agcatgagta     1380
caagaaatgg caggaaaaca gcgagcaggg gaggagagag gggcacgccc agaatcccat     1440
ggaaccttcc gtgccccagc tttctctcat ggatgtaaaa tgtgaaacgc ccaactgccc     1500
cttcttcatg tctgtgaaca cccagccttt atgccatgag tgctcagaga ggcggcaaaa     1560
gaatcaaaac aaactcccaa agctgaactc caagccgggc cctgaggggc tccctggcat     1620
ggcgctcggg gcctctcggg gagaagccta tgagcccttg gcgtggaacc ctgaggagtc     1680
cactgggggg cctcattcgg ccccaccgac agcacccagc cctttctgt tcagtgagac      1740 cactgccatg aagtgcagga gccccggctg ccccttcaca ctgaatgtgc agcacaacgg     1800
attttgtgaa cgttgccaca acgcccggca acttcacgcc agccacgccc cagaccacac     1860
aaggcacttg gatcccggga agtgccaagc ctgcctccag gatgttacca ggacatttaa     1920
tgggatctgc agtacttgct tcaaaaggac tacagcagag gcctcctcca gcctcagcac     1980
cagcctccct ccttcctgtc accagcgttc caagtcagat ccctcgcggc tcgtccggag     2040
cccctccccg cattcttgcc acagagctgg aaacgacgcc cctgctggct gcctgtctca     2100
agctgcacgg actcctgggg acaggacggg gacgagcaag tgcagaaaag ccggctgcgt     2160
gtattttggg actccagaaa acaagggctt ttgcacactg tgtttcatcg agtacagaga     2220
aaacaaacat tttgctgctg cctcagggaa agtcagtccc acagcgtcca ggttccagaa     2280
caccattccg tgcctgggga gggaatgcgg cacccttgga agcaccatgt ttgaaggata     2340
ctgccagaag tgtttcattg aagctcagaa tcagagattt catgaggcca aaggacaga      2400
```

```
agagcaactg agatcgagcc agcgcagaga tgtgcctcga accacacaaa gcacctcaag    2460
gcccaagtgc gcccgggcct cctgcaagaa catcctggcc tgccgcagcg aggagctctg    2520
catggagtgt cagcatccca accagaggat gggccctggg gcccaccggg gtgagcctgc    2580
ccccgaagac ccccccaagc agcgttgccg ggccccgcc  tgtgatcatt ttggcaatgc    2640
caagtgcaac ggctactgca acgaatgctt tcagttcaag cagatgtatg ctaaccgga    2700 aacaggtggg tcacctcctg caagaagtgg ggcctcgagc tgtcagtcat catggtgcta    2760
tcctctgaac ccctcagctg ccactgcaac agtgggctta agggtgtctg agcaggagag    2820
gaaagataag ctcttcgtgg tgcccacgat gctcaggttt ggtaacccgg gagtgttccc    2880
aggtggcctt agaaagcaaa gcttgtaact ggcaagggat gatgtcagat tcagcccaag    2940
gttcctcctc tcctaccaag caggaggcca ggaacttctt tggacttgga aggtgtgcgg    3000
ggactggccg aggcccctgc accctgcgca tcaggactgc ttcatcgtct tggctgagaa    3060
agggaaaaga cacacaagtc gcgtgggttg gagaagccag agccattcca cctcccctcc    3120
cccagcatct ctcagagatg tgaagccaga tcctcatggc agcgaggccc tctgcaagaa    3180
gctcaaggaa gctcagggaa aatggacgta ttcagagagt gtttgtagtt catggttttt    3240
ccctacctgc ccggttcctt tcctgaggac ccggcagaaa tgcagaacca tccatggact    3300
gtgattctga ggctgctgag actgaacatg ttcacattga cagaaaaaca agctgctctt    3360
tataatatgc acctttttaaa aaattagaat atttttactgg gaagacgtgt aactctttgg    3420
gttattactg tctttacttc taagaagtt agcttgaact gaggagtaaa agtgtgtaca    3480
tatataatat acccttacat tatgtatgag ggatttttttt aaattatatt gaatgctgc    3540 cctagaagta caataggaag gctaaataat aataacctgt tttctggttg ttgttggggc    3600
atgagcttgt gtatacactg cttgcataaa ctcaaccagc tgcctttta  aagggagctc    3660 tagtcctttt tgtgtaattc actttattta ttttattaca aacttcaaga ttatttaagt    3720
gaagatattt cttcagctct ggggaaaatg ccacagtgtt ctcctgagag aacatccttg    3780 cttttgagtca ggctgtgggc aagttcctga ccacagggag taaattggcc tcttttgatac    3840 actttttgctt gcctccccag gaaagaagga attgcatcca aggtatacat acatattcat    3900
cgatgtttcg tgcttctcct tatgaaactc cagctatgta ataaaaaact atactctgtg    3960
ttctgttaat gcctctgagt gtcctacctc cttggagatg agataggaa  ggagcaggga    4020 tgagactggc aatggtcaca gggaaagatg tggccttttg tgatggtttt attttctgtt    4080
aacactgtgt cctgggggg  ctgggaagtc ccctgcatcc catggtaccc tggtattggg    4140
acagcaaaag ccagtaacca tgagtatgag gaaatctctt tctgttgctg gcttacagtt    4200
tctctgtgtg cttttgtggtt gctgtcatat ttgctctaga agaaaaaaaa aaaaggaggg    4260
gaaatgcatt ttccccagag ataaaggctg ccattttggg ggtctgtact tatggcctga    4320
aaatatttgt gatccataac tctacacagc ctttactcat actattaggc acacttttccc    4380 cttagagccc cctaagtttt tcccagacga atctttataa tttctttcca aagataccaa    4440
ataaacttca gtgttttcat ctaattctct taaagttgat atcttaatat tttgtgttga    4500
tcattatttc cattcttaat gtgaaaaaaa gtaattattt atacttatta taaaagtat    4560 ttgaaatttg cacatttaat tgtccctaat agaaagccac ctattctttg ttggattttct    4620 tcaagttttt ctaaataaat gtaacttttc acaagagtca acattaaaaa ataaattatt    4680
taagaacaga aaaaaaaaaa aaaaa                                         4705
```

<210> SEQ ID NO 15
<211> LENGTH: 129
<212> TYPE: PRT
<213> ORGANISM: Homo sapiens

<400> SEQUENCE: 15

```
Met Ala Arg Gly Ser Leu Arg Arg Leu Leu Arg Leu Leu Val Leu Gly
1               5                   10                  15
Leu Trp Leu Ala Leu Leu Arg Ser Val Ala Gly Glu Gln Ala Pro Gly
            20                  25                  30
Thr Ala Pro Cys Ser Arg Gly Ser Ser Trp Ser Ala Asp Leu Asp Lys
        35                  40                  45
Cys Met Asp Cys Ala Ser Cys Arg Ala Arg Pro His Ser Asp Phe Cys
    50                  55                  60
Leu Gly Cys Ala Ala Ala Pro Pro Ala Pro Phe Arg Leu Leu Trp Pro
65                  70                  75                  80
Ile Leu Gly Gly Ala Leu Ser Leu Thr Phe Val Leu Gly Leu Leu Ser
                85                  90                  95
Gly Phe Leu Val Trp Arg Arg Cys Arg Arg Arg Glu Lys Phe Thr Thr
            100                 105                 110
Pro Ile Glu Glu Thr Gly Gly Glu Gly Cys Pro Ala Val Ala Leu Ile
        115                 120                 125
Gln
```

<210> SEQ ID NO 16
<211> LENGTH: 1048
<212> TYPE: DNA
<213> ORGANISM: Homo sapiens

<400> SEQUENCE: 16

| | | |
|---|---|---|
| aaggcggggg cggggcggg gcggcggccg tgggtccctg ccggccggcg gcgggcgcag | 60 |
| acagcggcgg gcgcaggacg tgcactatgg ctcggggctc gctgcgccgg ttgctgcggc | 120 |
| tcctcgtgct ggggctctgg ctggcgttgc tgcgctccgt ggccggggag caagcgccag | 180 |
| gcaccgcccc ctgctcccgc ggcagctcct ggagcgcgga cctggacaag tgcatggact | 240 |
| gcgcgtcttg cagggcgcga ccgcacagcg acttctgcct gggctgcgct gcagcacctc | 300 |
| ctgccccctt ccggctgctt tggcccatcc ttggggcgc tctgagcctg accttcgtgc | 360 |
| tggggctgct ttctggcttt ttggtctgga cgatgccg caggagagag aagttcacca | 420 |
| cccccataga ggagaccggc ggagagggct gcccagctgt ggcgctgatc cagtgacaat | 480 |
| gtgcccctg ccagccgggg ctcgcccact catcattcat tcatccattc tagagccagt | 540 |
| ctctgcctcc cagacgcggc gggagccaag ctcctccaac cacaaggggg gtggggggcg | 600 |
| gtgaatcacc tctgaggcct gggcccaggg ttcaggggaa ccttccaagg tgtctggttg | 660 |
| ccctgcctct ggctccagaa cagaaaggga gcctcacgct ggctcacaca aaacagctga | 720 |
| cactgactaa ggaactgcag catttgcaca ggggaggggg gtgccctcct tcctagaggc | 780 |
| cctgggggcc aggctgactt gggggcaga cttgacacta ggccccactc actcagatgt | 840 |
| cctgaaattc caccacgggg gtcaccctgg ggggttaggg acctattttt aacactaggg | 900 |
| ggctggccca ctaggagggc tggccctaag atacagaccc ccccaactcc ccaaagcggg | 960 |
| gaggagatat ttattttggg gagagtttgg aggggaggga gaatttatta ataaaagaat | 1020 |
| ctttaacttt aaaaaaaaaa aaaaaaaa | 1048 |

<210> SEQ ID NO 17

```
<211> LENGTH: 706
<212> TYPE: PRT
<213> ORGANISM: Homo sapiens

<400> SEQUENCE: 17

Met Glu Glu Asn Pro Thr Leu Glu Ser Glu Ala Trp Gly Ser Ser Arg
1               5                   10                  15

Glu Trp Leu Ala Pro Arg Glu Ala Arg Gly Gly Pro Ser Leu Ser Ser
            20                  25                  30

Val Leu Asn Glu Leu Pro Ser Ala Ala Thr Leu Arg Tyr Arg Asp Pro
        35                  40                  45

Gly Val Leu Pro Trp Gly Ala Leu Glu Glu Glu Glu Asp Gly Gly
    50                  55                  60

Arg Ser Arg Lys Ala Phe Thr Glu Val Thr Gln Thr Glu Leu Gln Asp
65                  70                  75                  80

Pro His Pro Ser Arg Glu Leu Pro Trp Pro Met Gln Ala Arg Arg Ala
                85                  90                  95

His Arg Gln Arg Asn Ala Ser Arg Asp Gln Val Val Tyr Gly Ser Gly
            100                 105                 110

Thr Lys Thr Asp Arg Trp Ala Arg Leu Leu Arg Ser Lys Glu Lys
        115                 120                 125

Thr Lys Glu Gly Leu Arg Ser Leu Gln Pro Trp Ala Trp Thr Leu Lys
130                 135                 140

Arg Ile Gly Gly Gln Phe Gly Ala Gly Thr Glu Ser Tyr Phe Ser Leu
145                 150                 155                 160

Leu Arg Phe Leu Leu Leu Leu Asn Val Leu Ala Ser Val Leu Met Ala
                165                 170                 175

Cys Met Thr Leu Leu Pro Thr Trp Leu Gly Gly Ala Pro Pro Gly Pro
            180                 185                 190

Pro Gly Pro Asp Ile Ser Ser Pro Cys Gly Ser Tyr Asn Pro His Ser
        195                 200                 205

Gln Gly Leu Val Thr Phe Ala Thr Gln Leu Phe Asn Leu Leu Ser Gly
    210                 215                 220

Glu Gly Tyr Leu Glu Trp Ser Pro Leu Phe Tyr Gly Phe Tyr Pro Pro
225                 230                 235                 240

Arg Pro Arg Leu Ala Val Thr Tyr Leu Cys Trp Ala Phe Ala Val Gly
                245                 250                 255

Leu Ile Cys Leu Leu Leu Ile Leu His Arg Ser Val Ser Gly Leu Lys
            260                 265                 270

Gln Thr Leu Leu Ala Glu Ser Glu Ala Leu Thr Ser Tyr Ser His Arg
        275                 280                 285

Val Phe Ser Ala Trp Asp Phe Gly Leu Cys Gly Asp Val His Val Arg
    290                 295                 300

Leu Arg Gln Arg Ile Ile Leu Tyr Glu Leu Lys Val Glu Leu Glu Glu
305                 310                 315                 320

Thr Val Val Arg Arg Gln Ala Ala Val Arg Thr Leu Gly Gln Gln Ala
                325                 330                 335

Arg Val Trp Leu Val Arg Val Leu Leu Asn Leu Leu Val Val Ala Leu
            340                 345                 350

Leu Gly Ala Ala Phe Tyr Gly Val Tyr Trp Ala Thr Gly Cys Thr Val
        355                 360                 365

Glu Leu Gln Glu Met Pro Leu Val Gln Glu Leu Pro Leu Leu Lys Leu
    370                 375                 380

Gly Val Asn Tyr Leu Pro Ser Ile Phe Ile Ala Gly Val Asn Phe Val
```

Leu Pro Pro Val Phe Lys Leu Ile Ala Pro Leu Glu Gly Tyr Thr Arg
385                 390                 395                 400
                405                 410                 415

Ser Arg Gln Ile Val Phe Ile Leu Leu Arg Thr Val Phe Leu Arg Leu
                420                 425                 430

Ala Ser Leu Val Val Leu Leu Phe Ser Leu Trp Asn Gln Ile Thr Cys
            435                 440                 445

Gly Gly Asp Ser Glu Ala Glu Asp Cys Lys Thr Cys Gly Tyr Asn Tyr
        450                 455                 460

Lys Gln Leu Pro Cys Trp Glu Thr Val Leu Gly Gln Glu Met Tyr Lys
465                 470                 475                 480

Leu Leu Leu Phe Asp Leu Leu Thr Val Leu Ala Val Ala Leu Leu Ile
                485                 490                 495

Gln Phe Pro Arg Lys Leu Leu Cys Gly Leu Cys Pro Gly Ala Leu Gly
            500                 505                 510

Arg Leu Ala Gly Thr Gln Glu Phe Gln Val Pro Asp Glu Val Leu Gly
        515                 520                 525

Leu Ile Tyr Ala Gln Thr Val Val Trp Val Gly Ser Phe Phe Cys Pro
530                 535                 540

Leu Leu Pro Leu Leu Asn Thr Val Lys Phe Leu Leu Phe Tyr Leu
545                 550                 555                 560

Lys Lys Leu Thr Leu Phe Ser Thr Cys Ser Pro Ala Ala Arg Thr Phe
                565                 570                 575

Arg Ala Ser Ala Ala Asn Phe Phe Pro Leu Val Leu Leu Leu Gly
                580                 585                 590

Leu Ala Ile Ser Ser Val Pro Leu Leu Tyr Ser Ile Phe Leu Ile Pro
                595                 600                 605

Pro Ser Lys Leu Cys Gly Pro Phe Arg Gly Gln Ser Ser Ile Trp Ala
610                 615                 620

Gln Ile Pro Glu Ser Ile Ser Ser Leu Pro Glu Thr Thr Gln Asn Phe
625                 630                 635                 640

Leu Phe Phe Leu Gly Thr Gln Ala Phe Ala Val Pro Leu Leu Leu Ile
                645                 650                 655

Ser Ser Ile Leu Met Ala Tyr Thr Val Ala Leu Ala Asn Ser Tyr Gly
                660                 665                 670

Arg Leu Ile Ser Glu Leu Lys Arg Gln Arg Glu Thr Glu Ala Gln Asn
675                 680                 685

Lys Val Phe Leu Ala Arg Arg Ala Val Ala Leu Thr Ser Thr Lys Pro
            690                 695                 700

Ala Leu
705

<210> SEQ ID NO 18
<211> LENGTH: 2477
<212> TYPE: DNA
<213> ORGANISM: Homo sapiens

<400> SEQUENCE: 18
ctgagaaacc acaggaagtg taccttactc cctccgggcc acctgctggc caggtacaca    60 cctgccctg gccctccct tacctggggc agtgtctgcc tggtggccac tagagacagc    120
ccagcctggg gccatggaag aaaacccgac cttggaatca gaagcctggg gctcctctag    180
ggagtggctg gccccgggg aggccagagg aggcccatcg ctgtcttctg tgctgaacga    240
gctgcccagt gctgccaccc ttcggtaccg agacctgggg gtgctgcctt ggggggcgct    300

```
ggaggaggag gaggaggatg gaggaaggag cagaaaggcc ttcacagaag tcacccagac    360
agagctgcag gaccctcacc cttcccggga actgccctgg cccatgcagg ccagacgggc    420
acacaggcaa agaaatgcca gcagggacca ggtggtctat ggctctggaa ctaagacgga    480
ccgatgggcg cggctacttc ggaggtccaa ggagaaaaca aaggaaggct tgcgaagcct    540
gcagccctgg gcgtggacac tgaagaggat cggggggccag tttggcgccg gcacggagtc   600
ctacttctcc ctgctgcgct tcctgctcct tcttaacgtg ctggcctctg tgctcatggc    660
ctgcatgacg ctgctgccca cctggttggg aggcgctccc ccaggccctc ccggccccga    720
catctcctcg ccctgcggct cctataaccc ccactcccag ggcctggtca cctttgccac    780
ccagctcttc aacttgctct cgggtgaggg ttacctggaa tggtcccctc tcttctatgg    840
cttctacccg ccccgcccac gcctggcggt cacctacctg tgctgggcct ttgccgttgg    900
cctcatctgc ctcctgctca tcctgcatcg ctcggtgtct gggctgaagc agacactgct    960
ggcggagtcc gaggctctga ccagctacag ccaccgggtg ttctcggcct gggacttcgg   1020
tctctgcggg gacgtccacg tgcggctgcg ccagcgcatc atcttgtacg aattaaaggt   1080
ggagctggag gagacagtgg tgcggcgcca ggctgcggtg cggacgctgg gccagcaagc   1140
cagggtttgg ttggtgcggg tgctgctcaa cctgctggtg gtcgcgctcc tggggggcagc  1200 cttctatggc gtctactggg ctacggggtg caccgtggag ctgcaggaga tgccccttgt   1260
ccaggagttg ccactgctga agcttggggt gaattacctt ccgtccatct tcatcgctgg   1320
ggtcaatttt gtgctgccgc ccgtgttcaa gctcattgct ccactggagg gctacactcg   1380
gagtcgccag atcgttttta tcctgctcag gaccgtgttt cttcgcctcg cctccctggt   1440
ggtcctgctc ttctctctct ggaatcagat cacttgtggg ggcgactccg aggctgagga   1500
ctgcaaaacc tgtggctaca attacaaaca acttccgtgc tgggagactg tcctgggcca   1560
ggaaatgtac aaacttctgc tctttgatct gctgactgtc ttggcagtcg cgctgctcat   1620
ccagtttcct agaaagctcc tctgtggcct ctgtcctggg gcgctgggtc gtctggcggg   1680
gacccaagag ttccaggtgc ccgacgaggt gctgggctc atctacgcgc agacggtggt   1740
ctgggtgggg agttttttct gcccttttact gcccctgctt aacacggtca agttcctgct   1800
gcttttctac ctgaagaagc ttaccctctt ctccacctgc tccccggctg cccgcacctt   1860
ccgggcctcc gcggcgaatt tctttttccc cttggtcctt ctcctgggtc tggccatctc   1920
cagcgttccc ctgctttaca gcatcttcct gatcccgcct tctaagctgt gtggtccatt   1980
ccgggggcag tcgtccatct gggcccagat ccctgagtct atttccagcc tccctgagac   2040
cacccagaat ttcctcttct tcctggggac ccaggctttt gctgtgcccc ttctgctgat   2100
ctccagcatc ctgatggcgt acactgtggc tctggctaac tcctacggac gcctcatctc   2160
tgagctcaaa cgtcagagag agacggaggc gcagaataaa gtcttcctgg cacggcgcgc   2220
tgtggcgctg acctccacca aaccggctct ttgaccccg cagcccacgt cccgctttca   2280
gaccccaggc ccattgtaag cctaggtcac aacatctgta aactaggaga actggagaag   2340
actccacgcc cttccagctt tggtatctgg agattccag gcccctcgc cgccacgtcc     2400 ctgactctcg ggtgatcttc cttgtatcaa taaatacagc cgaggttgct gagcgcgctt   2460
tgaaaaaaaa aaaaaaa                                                   2477
```

IDENTIFICATION OF UNIQUE BLOOD-BASED GENE EXPRESSION PROFILES IN CHILDREN WITH REGRESSIVE AUTISM SPECTRUM DISORDER (ASD) AND ILEOCOLITIS

CROSS-REFERENCE TO RELATED APPLICATIONS

This present application is a 35 U.S.C. § 371 national phase application from, and claims priority to, International Application No. PCT/US2017/024037, filed Mar. 24, 2017, and published under PCT Article 21(2) in English, which claims priority under 35 U.S.C. § 119(e) to U.S. Provisional Patent Application No. 62/315,391, filed Mar. 30, 2016, which are incorporated herein by reference in their entirety.

BACKGROUND OF THE INVENTION

Gastrointestinal (GI) symptoms are a common comorbidity in children with autism (McElhanon et al., 2014, Pediatrics 133:872-883; Chaidez et al., 2014, J Autism Dev Disord 44:1117-1127; Gorrindo et al., 2012, Autism Res 5:101-108; Buie et al., 2010, Pediatrics 125 Suppl 1: S1-18; Bauman et al., 2010, Neurotherapeutics 7(3): 320-327; Smith et al., 2009, Autism 13:343-355; Valicenti-McDermott et al., 2006, J Dev Behav Pediatr 27(2 Suppl): S128-136; Horvath et al., 2002, Current Opinion in Ped 14: 583-587; Krigsman et al., 2010, Autism Insights 1: 1-11; Horvath et al., 1999, Journal of Pediatrics 135(5):559-563) occurring at a frequency as high as 85% (Gorrindo et al., 2012, Autism Res 5:101-108; Valicenti-McDermott et al., 2006, J Dev Behav Pediatr 27(2 Suppl): S128-136). Symptoms most often reported are constipation, diarrhea, abdominal pain, abdominal distention, and food intolerances (McElhanon et al., 2014, Pediatrics 133:872-883; Buie et al., 2010, Pediatrics 125 Suppl 1: S1-18; Bauman et al., 2010, Neurotherapeutics 7(3): 320-327; Krigsman et al., 2010, Autism Insights 1: 1-11). Following examination of endoscopically obtained gastrointestinal tissue in GI symptomatic autism spectrum disorder (ASD) children, numerous pathologic etiologies that may explain these GI symptoms have been described including gastroesophageal reflux (GERD) (Horvath et al., 1999, Journal of Pediatrics 135(5):559-563), eosinophilic esophagitis (Jarocka-Cyrta et al., 2011, J Autism Dev Disord 41(3): 372-374), food allergies (Lyall et al., 2015, Autism Res 8(5):567-574), and inflammatory bowel disease (IBD) (Doshi-Velez et al., 2015, Bowel Dis. 21(10):2281-2288). IBD has been shown to occur with greater frequency in ASD than in typically-developing children (Doshi-Velez et al., 2015, Bowel Dis. 21(10):2281-2288).

In addition to these diagnoses found also in non-ASD children, GI symptoms in ASD have also been attributed to a unique variant of inflammatory bowel disease seen only in children with ASD (Krigsman et al., 2010, Autism Insights 1: 1-11; Wakefield et al., 1998, Lancet 351(9103):637-41; Wakefield et al., 2000, American Journal of Gastroenterology 95(9):2285-2295; Gonzalez et al., 2005, Arch Venez Pueric Pediat 69: 19-25). Distinguishing features of this ASD-associated inflammatory bowel disease have been described in the stomach (Torrente et al., 2004, Am J Gastroenterol 4: 598-605), small intestine (Torrente et al., 2002, Mol Psychiatry 7: 375-382; Ashwood et al., 2004, J Clin Immunol 24: 664-673; Ashwood et al., 2006, Neuroimmunol 173: 126-134; Walker et al., 2013, PLoS One 8:e58058), and colon (Ashwood et al., 2004, J Clin Immunol 24: 664-673; Walker et al., 2013, PLoS One 8:e58058; Furlano et al., 2001, J Pediatr 138: 366-372) of GI symptomatic ASD children undergoing diagnostic endoscopy in which unique cellular, immunohistochemical and molecular properties have been characterized. ASD-associated ileocolitis has been shown to occur at a frequency of up to 70% in GI symptomatic children undergoing diagnostic ileocolonoscopy (Krigsman et al., 2010, Autism Insights 1: 1-11) and represents a much higher prevalence than the already increased incidence of "classic" IBD seen in these children (Doshi-Velez et al, 2015, Inflamm Bowel Dis. 21(10):2281-228813). The clinical significance of identification and treatment of ASD-associated ileocolitis and IBD extends beyond simple resolution of troubling chronic GI symptoms, especially in light of the association of GI symptoms with extremes of ASD behavioral features (Chaidez et al., 2014, J Autism Dev Disord 44:1117-1127; Gorrindo et al., 2012, Autism Res 5:101-108; Mazurek et al., 2013, J Abnorm Child Psychol 41(1): 165-176; Maenner et al., 2012, J Autism Dev Disord 42(7): 1520-1525; Adams et al., 2011, BMC Gastroenterology 11:22; Nikolov et al., 2009, J Autism Dev Disord 39(3):405-41323-26). As such, treatment of symptomatic underlying GI pathology, regardless of its etiology, may improve not only the presenting GI symptoms but behavioral symptoms as well.

Historically, GI symptoms presenting in the setting of ASD have often either gone unrecognized (Buie et al., 2010, Pediatrics 125 Suppl 1: S1-18) or been treated empirically. Empiric treatment of a chronic condition such an inflammatory bowel disease typically affords only transient improvement, if any at all. Because of the significant practical difficulties inherent in performing diagnostic endoscopy in GI symptomatic children with ASD, a blood biomarker that could reliably identify those GI symptomatic ASD children most likely to have an IBD, and thus be most likely to benefit from diagnostic endoscopy, would be of enormous clinical value.

Currently, a formal ASD diagnosis is based upon meeting DSMV criteria and unfortunately the diagnosis is often given at a time beyond the ideal "developmental window of opportunity" for commencing time-sensitive, maximally effective, interventions. For this reason the search for diagnostic biomarkers capable of identifying at-risk children as early as possible has become a priority (Loth et al., 2016, Nat Rev Drug Discov 15(1):70-73; Ruggeri et al., 2014, Psychopharmacology (Berl) 231(6):1201-1216; Pierce et al., 2009, Ann Clin Psychiatry 21(3):132-147). There are numerous efforts currently underway to identify diagnostically relevant biomolecules (e.g. microRNAs (Vasu et al., 2014, Mol Autism 5(40):1-9), mitochondrial DNA (Chen et al., 2015, BMC Psychiatry 15(50):1-7), cytokines (Jyonouchi et al., 2014, J Neuroinflammation 11(187): 1-13), mRNAs (Pramparo et al., 2015, JAMA Psychiatry 72(4):386-394; Yang et al., 2015, Neuroscience 284:290-296; Segura et al., 2015, Neurogenetics 16(2):123-131; Kong et al., 2013, Neurogenetics 14:143-152; Campbell et al., 2013, BMC Medical Genomics 6(34): 1-15; Kong et al., 2012, PLoS One 7(12):1-13; Glatt et al., 2012, J Am Acad Child Adolesc Psychiatry 51(9):934-944; Taurines et al., 2011, World J Biol Psychiatry Suppl 1:104-108) in the peripheral blood of at-risk children.

Given the broad heterogeneity that is the hallmark of ASD, coupled with the understanding that earlier diagnosis and treatment provides the greatest chance for the most positive outcomes, a blood-based test to diagnose autism (and/or ASD subtypes) early on would have tremendous clinical value. A key confound in these efforts, heterogeneity (in the form of ASD subtypes) exists within the core domains (language, social interaction, and range of interests), but also within associated medical comorbidity domains (e.g. epilepsy, sleep disorders, gastrointestinal disorders, etc.).

Biomarker discovery efforts especially relevant to the area of inflammatory bowel disease are numerous. Diagnostic uncertainty resultant from clinical overlap between the two recognized types of IBD—Crohn's disease (CD) and ulcerative colitis (UC)—have inspired the numerous attempts to delineate IBD subtypes through comparisons of gene expression profiles in either mucosal biopsy tissue (e.g. Wu et al., 2006, Inflamm Bowel Dis 13(7):807-821; von Stein et al., 2008, Gastroenterology 134(7):1869-1881; von Stein et al., 2009, Expert Rev Mol Diag 9(1):7-10; Granlund et al., 2013, PLoS One 8(2): 1-13] or peripheral blood (e.g., Mannick et al., 2004, Clin Immunol 112(3):247-257; Burczynski et al., 2005, J Mol Diag 8(1):51-61; Sipos et al., 2011, Dis Markers 30(1):1-17; Burakoff et al., 2011, Inflamm Bowel Dis 17(8):1719-1725; van Lierop et al., 2013, PLoS One 8(11):1-8). Moreover, these efforts are driven by the fact that getting the appropriate (and definitive) IBD diagnosis has important implications for early and successful therapeutic intervention and disease management. Because ileocolitis in ASD children shares many clinical and molecular similarities with classic pediatric IBD while at the same time having distinct clinical and molecular features, our original mucosal-based gene expression study in ASD$^{IC+}$ children (Walker et al., 2013, PLoS One 8:e58058) was modeled after the study by von Stein (von Stein et al., 2009, Expert Rev Mol Diag 9(1):7-10) that reported a biomarker, consisting of seven transcripts, which could be used to distinguish Crohn's disease from ulcerative colitis.

The rationale for evaluating peripheral blood in search of disease biomarkers begins with the answer to an important fundamental question: "To what extent does expression in WBCs (white blood cells) reflect expression in other organ systems?" (Kohane et al., 2012, Bioinformatics 28(4):538-545). More specifically, if one is investigating, for example, a neuropsychiatric disease with a known pathophysiological signature in the brain, can one use the correlation/overlap between brain and blood gene expression to derive a peripheral blood-based biomarker that will faithfully identify affected individuals? To answer that question, several groups have looked specifically at the overlap of gene expression in the blood and brain tissue from diseased and control individuals (Tsuang et al., 2005, Am J Genet B Neuropsychiatr Genet 133B(1):1-5; Glatt et al., 2005, Proc Natl Acad Sci USA 102(43):15533-15538; Sullivan et al., 2006, Am J Genet B Neuropsychiatr Genet 141B(3):261-268; Rollins et al., 2010, Am J Genet B Neuropsychiatr Genet 153B(3): 919-936). In fact, a recent review of eight brain/blood gene expression studies found that between 35% and 80% of known transcripts are found in both tissues and estimates of correlated (cross-tissue) expression levels ranged from 0.25-0.64, with the higher correlation found, not surprisingly, among specific subsets of genes (Tylee et al., 2013, Am J Genet B Neuropsychiatr Genet 162B(3):595-603). One of the studies in particular that measured gene expression in cadaveric brain tissue from patients with schizophrenia (SZ) and compared profiles to gene expression in peripheral blood from living SZ patients found (and validated) a strong SZ biomarker candidate gene (SELENBP1) (Glatt et al., 2005, Proc Natl Acad Sci USA 102(43): 15533-15538). The authors concluded that "the identification of valid peripheral biomarkers for SZ may ultimately facilitate early identification, intervention, and prevention efforts" (Glatt et al., 2005, Proc Natl Acad Sci USA 102(43):15533-15538).

A major limitation of these types of studies has always been the quantity and quality of human banked tissue available for study (Cai et al., 2010, BMC Genomics 11(589):1-15). A second important confound is that the brain gene expression data (often from brain bank tissues) and the blood gene expression data (often from living donors) typically do not come from the same individuals. Consequently, these types of studies—whose goal is to identify peripheral biomarkers through the evaluation and comparison of diseased organ tissues and peripheral blood—are rarely able to be performed optimally due to the difficulty in obtaining relevant tissues for analysis.

Therefore, there is a need in the art for blood-based methods of diagnosing ASD, and GI disorders in children with ASD. The present invention satisfies this unmet need.

SUMMARY OF THE INVENTION

In one aspect the invention comprises a method of treating a subject having a gastrointestinal disorder, the method comprising administering a treatment for gastrointestinal disorder to a pre-selected subject, wherein the subject is pre-selected by detecting an alteration in the level of a polypeptide or polynucleotide of at least one biomarker selected from the group consisting of FCER1A, CYP2S1, TMC4, IL1RN, TNFAIP3, CENPE, MTHFD2, and SIGLEC17P relative to a reference in a blood sample obtained from the subject.

In another aspect the invention comprises a method of diagnosing a gastrointestinal disorder in a subject, the method comprising measuring the level of a polypeptide or polynucleotide of at least one biomarker selected from the group consisting of FCER1A, CYP2S1, TMC4, IL1RN, TNFAIP3, CENPE, MTHFD2, and SIGLEC17P in a blood sample from the subject, wherein an alteration in the level of the polypeptide or polynucleotide relative to a reference indicates that the subject has a gastrointestinal disorder.

In some embodiments the subject is pre-selected by further detecting an alteration in the level of TNFRSF12A polypeptide or polynucleotide.

In some embodiments, the invention further comprises measuring the level of TNFRSF12A polypeptide or polynucleotide.

In some embodiments the subject is pre-selected by detecting an alteration in the level of a IL1RN polypeptide or polynucleotide, MTHFD2 polypeptide or polynucleotide, and SIGLEC17P polypeptide or polynucleotide.

In some embodiments the method comprises measuring the level of a IL1RN polypeptide or polynucleotide, MTHFD2 polypeptide or polynucleotide, and SIGLEC17P polypeptide or polynucleotide.

In some embodiments the alteration comprises an increase in the level of TMC4 polypeptide or polynucleotide, an increase in the level of TNFAIP3 polypeptide or polynucleotide, a decrease in the level of FCER1A polypeptide or polynucleotide, a decrease in the level of CYP2S1 polypeptide or polynucleotide, a decrease in the level of TNFRSF12A polypeptide or polynucleotide, a decrease in the level of IL1RN polypeptide or polynucleotide, a decrease in the level of CENPE polypeptide or polynucleotide, a decrease in the level of MTHFD2 polypeptide or polynucleotide, or a decrease in the level of SIGLEC17P polypeptide or polynucleotide.

In some embodiments the gastrointestinal disorder is ileocolitis, ileitis, colitis, enteritis, duodenitis, gastritis, and/or esophagitis.

In some embodiments the subject is a child.

In some embodiments the subject has an autism spectrum disorder.

In some embodiments measuring comprises PCR assays or microarrays.

In some embodiments the method further comprises a step of using the results obtained from the diagnostic assay to selecting or administering a treatment.

In some embodiments the treatment comprises corticosteroids, immunomodulators, 5-aminosalicylic acid preparations, cytokine specific antagonists, dietary restrictions, antimicrobials, probiotics, and/or supplemental digestive enzymes.

In another aspect the invention comprises a method of diagnosing autism spectrum disorder (ASD) in a subject, the method comprising measuring the level of a polypeptide or polynucleotide of at least one biomarker selected from the group consisting of FCER1A, CYP2S1, TMC4, IL1RN, TNFAIP3, CENPE, MTHFD2, and SIGLEC17P in a blood sample from the subject, wherein an alteration in the level of the polypeptide or polynucleotide relative to a reference indicates that the subject has autism spectrum disorder.

In some embodiments the method further comprises measuring the level of TNFRSF12A polypeptide or polynucleotide.

In some embodiments the method comprises measuring the level of a polypeptide or polynucleotide of biomarkers IL1RN, MTHFD2, and SIGLEC17P.

In some embodiments the alteration comprises an increase in the level of TMC4 polypeptide or polynucleotide, an increase in the level of TNFAIP3 polypeptide or polynucleotide, a decrease in the level of FCER1A polypeptide or polynucleotide, a decrease in the level of CYP2S1 polypeptide or polynucleotide, a decrease in the level of TNFRSF12A polypeptide or polynucleotide, a decrease in the level of IL1RN polypeptide or polynucleotide, a decrease in the level of CENPE polypeptide or polynucleotide, a decrease in the level of MTHFD2 polypeptide or polynucleotide, or a decrease in the level of SIGLEC17P polypeptide or polynucleotide.

In some embodiments the autism spectrum disorder is autism.

In some embodiments the subject is a child.

In some embodiments the measuring comprises PCR assays or microarrays.

In some embodiments the method further comprises a step of using the results obtained from the diagnostic assay to selecting or administering a treatment.

In some embodiments the treatment comprises corticosteroids, immunomodulators, 5-aminosalicylic acid preparations, cytokine specific antagonists, dietary restrictions, antimicrobials, probiotics, and/or supplemental digestive enzymes.

In another aspect the invention comprises a kit for the diagnosis of a gastrointestinal and/or autism spectrum disorder, the kit comprising at least one agent capable of specifically binding or hybridizing to a polypeptide or polynucleotide of a biomarker selected from the group consisting of FCER1A, CYP2S1, TMC4, IL1RN, TNFAIP3, CENPE, MTHFD2, or SIGLEC17P, and directions for using the agent for the diagnosis of a gastrointestinal and/or autism spectrum disorder.

In some embodiments the kit comprises an agent capable of specifically binding or hybridizing to a polypeptide or polynucleotide of TNFRSF12A.

In some embodiments the kit comprises an agent capable of specifically binding or hybridizing to a polypeptide or polynucleotide of IL1RN, an agent capable of specifically binding or hybridizing to a polypeptide or polynucleotide of MTHFD2, and an agent capable of specifically binding or hybridizing to a polypeptide or polynucleotide of SIGLEC17P.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 6A shows an ROC curve for gene FCER1A. FIG. 6B shows an ROC curve for gene CYP2S1. FIG. 6C shows an ROC curve for gene TNFRSF12A. FIG. 6D shows an ROC curve for gene TMC4. FIG. 6E shows an ROC curve for gene IL1RN. FIG. 6F shows an ROC curve for gene TNFAIP3. FIG. 6G shows an ROC curve for gene CENPE. FIG. 6H shows an ROC curve for gene MTHFD2. FIG. 6I shows an ROC curve for gene SIGLEC17P.

DETAILED DESCRIPTION

Figure 1:
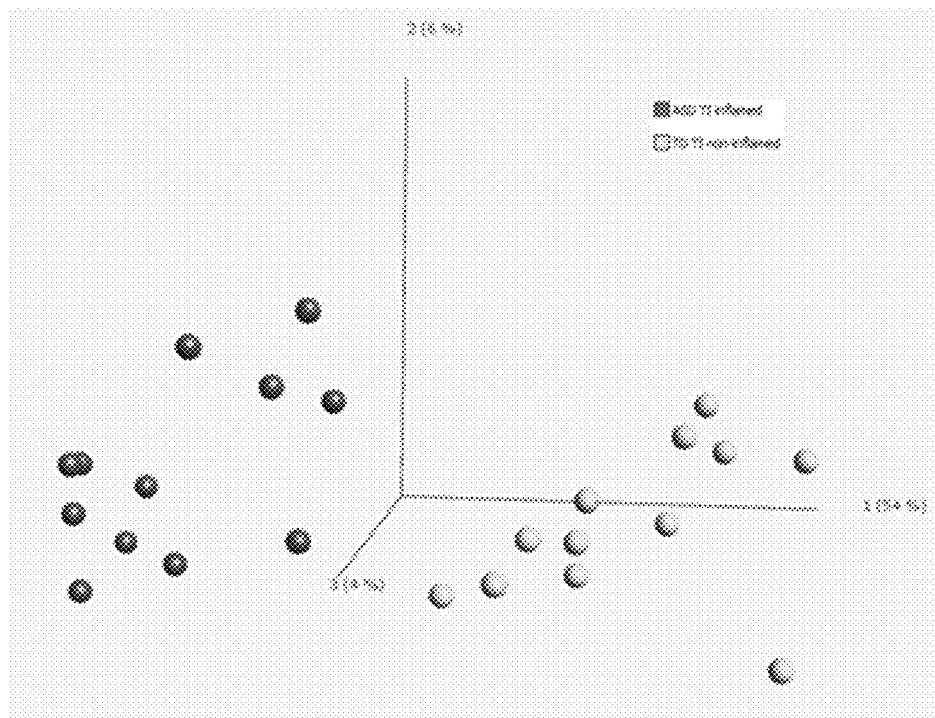
FIG. 1 is a set of plots showing a comparison of gene expression profiles from inflamed terminal ileum tissue from ASD patients compared to non-inflamed TI tissue from TD controls (top panel) and corresponding profiles in colonic tissue (bottom panel) at p=0.001 using principal component analysis (teal/dark grey=ASD-TI inflamed; yellow/light grey=TD-TI non-inflamed; violet/dark grey=ASD colon inflamed; yellow/light grey=TD colon non-inflamed).
Figure 1:
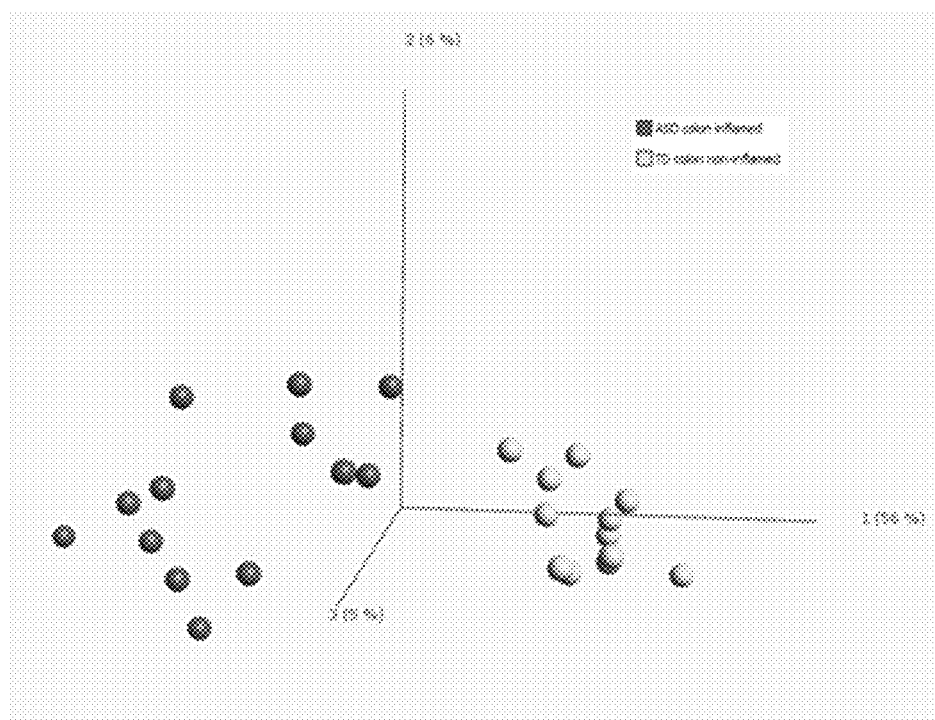

The present invention relates generally to diagnostic methods and markers, prognostic methods and markers, and therapy evaluators for autism. In one embodiment, the markers of the invention make up a gene expression profile unique to children (i.e., newborn to age 21) with autism spectrum disorder (ASD) who have comorbid gastrointestinal inflammation (referred herein as "ASD$^{IC}$").

Previously, an intestinally derived molecular profile of histological ASD-associated ileocolitis that confirms, on a molecular level, the presence of an ASD-associated inflammatory bowel disease ("IBD") and discriminates it from other IBDs such as Crohn's disease ("CD") and ulcerative colitis ("UC") was reported (Walker et al., 2013, PLoS One 8:e58058; United States Patent Publication No. 2015-0361499 A1). In the study described herein, the findings in Walker et al., 2013, PLoS One 8:e58058 were extended in an additional case/control cohort. Reported herein is the presence of a blood-based gene expression profile that reflects the presence of ASD-associated ileocolitis and provides a putative, clinically relevant, surrogate biomarker.

Accordingly, in one embodiment, the present invention relates to blood-based biomarkers of ASD$^{IC}$, methods for diagnosis of ASD$^{IC}$, methods of determining predisposition to ASD$^{IC}$, methods of monitoring progression/regression of ASD$^{IC}$, methods of assessing efficacy of compositions for treating ASD$^{IC}$, methods of screening compositions for activity in modulating biomarkers of ASD$^{IC}$, methods of treating ASD$^{IC}$, as well as other methods based on detection of biomarkers of ASD$^{IC}$ in a blood sample.

In one embodiment, the markers of the invention are useful for discriminating between different inflammatory disorders including but is not limited to Crohn's disease, ulcerative colitis, inflammatory bowel disease (IBD), and ASD$^{IC}$.

In one embodiment, the markers of the invention diagnose ASD-associated ileocolitis.

In one embodiment, the present invention relates to biomarkers of ASD-associated ileocolitis, methods for diagnosis of ASD-associated ileocolitis, methods of determining predisposition to ASD-associated ileocolitis, methods of monitoring progression/regression of ASD-associated ileocolitis, methods of assessing efficacy of compositions for treating ASD-associated ileocolitis, methods of screening compositions for activity in modulating biomarkers of ASD-associated ileocolitis, methods of treating ASD-associated ileocolitis, as well as other methods based on biomarkers of ASD-associated ileocolitis.

The invention also provides a method for permitting refinement of disease diagnosis, disease risk prediction, and clinical management of patients associated with ASD-associated inflammatory disease. That is, the biomarkers of the invention can be used as a marker for the disease state or disease risk. For example, the presence of the selective biomarkers of the invention permits refinement of disease diagnosis, disease risk prediction, and clinical management of patients being treated with agents that are associated with a particular ASD-associated inflammatory disease.

The invention also provides a method of diagnosing, treating, and monitoring autism, even without accompanying inflammatory bowel disease.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element. "About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%.

"Amplification" refers to any means by which a polynucleotide sequence is copied and thus expanded into a larger number of polynucleotide sequences, e.g., by reverse transcription, polymerase chain reaction or ligase chain reaction, among others.

An "analyte", as used herein refers to any substance or chemical constituent that is undergoing analysis. For example, an "analyte" can refer to any atom and/or molecule; including their complexes and fragment ions. The term may refer to a single component or a set of components. In the case of biological molecules/macromolecules, such analytes include but are not limited to: polypeptides, polynucleotides, proteins, peptides, antibodies, DNA, RNA, carbohydrates, steroids, and lipids, and any detectable moiety thereof, e.g. immunologically detectable fragments. In some instances, an analyte can be a biomarker.

The term "assessing" includes any form of measurement, and includes determining if an element is present or not. The terms "determining," "measuring," "evaluating," "assessing," and "assaying" are used interchangeably and include quantitative and qualitative determinations. Assessing may be relative or absolute. "Assessing the presence of" includes determining the amount of something present, and/or determining whether it is present or absent.

The term "autism spectrum disorder (ASD)" refers to a group of developmental brain disorders, having a wide range of symptoms characterized by social deficits and communication difficulties, stereotyped or repetitive behaviors and interests, and in some cases, cognitive delays. ASD is typically diagnosed according to guidelines listed in the American Psychiatric Association's *Diagnostic and Statistical Manual of Mental Disorders 5th edition* (DSM-5). ASDs include autism and Asperger syndrome. To various degrees, the psychiatric diagnosis of ASDs is subjective in nature as it based solely on observed behaviors and not on any quantifiable biologic, physiologic, immunologic, histologic processes or organ imaging technique.

The term "biomarker" or "marker" is a characteristic that is objectively measured and evaluated as an indicator of normal biological processes, pathological processes, or pharmacological responses to a therapeutic intervention. The biomarker can for example describe a substance whose detection indicates a particular disease state. The biomarker may be a peptide that causes disease or is associated with susceptibility to disease. In some instances, the biomarker may be a gene that causes disease or is associated with susceptibility to disease. In other instances, the biomarker is a metabolite. In any event, the biomarker can be differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker is preferably differentially present at a level that is statistically significant (i.e., a p-value less than 0.05 and/or a q-value of less than 0.10 as determined using either Welch's T-test or Wilcoxon's rank-sum Test).

By "CENPE polypeptide" is meant a polypeptide or fragment thereof having at least about 85% amino acid identity to NCBI Accession No. NP_001804.2 and having a biological activity of a CENPE (centromere-associated protein E) polypeptide. Biological activities of a CENPE polypeptide include microtubule motor activity, microtubule binding, ATP binding, and ATPase activity. The sequence at NCBI Accession No. NP_001804.2 is shown below: SEQ ID NO: 1

```
   1  maeegavavc vrvrplnsre eslgetaqvy wktdnnviyq vdgsksfnfd rvfhgnettk
  61  nvyeeiaapi idsaiqgyng tifaygqtas gktytmmgse dhlgviprai hdifqkikkf
 121  pdrefllrvs ymeiynetit dllcgtqkmk pliiredvnr nvyvadltee vvytsemalk
 181  witkgeksrh ygetkmnqrs srshtifrmi lesrekgeps ncegsvkvsh lnlvdlagse
 241  raaqtgaagv rlkegcninr slfilgqvik klsdgqvggf inyrdskltr ilqnslggna
 301  ktriictitp vsfdetltal qfastakymk ntpyvnevst deallkryrk eimdlkkqle
 361  evsletraqa mekdqlaqll eekdllqkvq nekienltrm lvtsssltlq qelkakrkrr
 421  vtwclgkink mknsnyadqf niptnittkt hklsinllre idesvcsesd vfsntldtls
 481  eiewnpatkl lnqeniesel nslradydnl vldyeqlrte keemelklke kndldefeal
 541  erktkkdqem qliheisnlk nlvkhaevyn qdlenelssk vellrekedq ikklqeyids
 601  qklenikmdl syslesiedp kqmkqtlfda etvaldakre saflrsenle lkekmkelat
 661  tykqmendiq lyqsqleakk kmqvdlekel qsafneitkl tslidgkvpk dllcnleleg
 721  kitdlqkeln keveenealr eevillselk slpseverlr keiqdkseel hiitsekdkl
 781  fsevvhkesr vqglleeigk tkddlattqs nykstdqefq nfktlhmdfe qkykmvleen
 841  ermnqeivnl skeaqkfdss lgalktelsy ktqelqektr evqerlneme qlkeqlenrd
 901  stlqtverek tliteklqqt leevktltqe kddlkqlqes lqierdqlks dihdtvnmni
 961  dtqeqlrnal eslkqhqeti ntlkskisee vsrnlhmeen tgetkdefqq kmvgidkkqd
1021  leakntqtlt advkdneiie qqrkifsliq eknelqqmle sviaekeqlk tdlkeniemt
1081  ienqeelrll gdelkkqqei vaqeknhaik kegelsrtcd rlaeveeklk eksqqlqekq
1141  qqllnvqeem semqkkinei enlknelknk eltlehmete rlelaqklne nyeevksitk
1201  erkvlkelqk sfeterdhlr gyireieatg lqtkeelkia hihlkehqet idelirsvse
1261  ktaqiintqd lekshtklqe eipvlheeqe llpnvkevse tqetmnelel lteqsttkds
1321  ttlariemer lrlnekfqes qeeiksltke rdnlktikea levkhdqlke hiretlakiq
1381  esqskqeqsl nmkekdnett kivsemeqfk pkdsallrie iemlglskrl qeshdemksv
1441  akekddlqrl qevlqsesdq lkenikeiva khleteeelk vahcclkeqe etinelrvnl
1501  seketeisti qkqleaindk lqnkiqeiye keeqfnikqi sevqekvnel kqfkehrkak
1561  dsalqsiesk mleltnrlqe sqeeiqimik ekeemkrvqe alqierdqlk entkeivakm
1621  kesqekeyqf lkmtavnetq ekmceiehlk eqfetqklnl enieteninrl tqilhenlee
1681  mrsvtkerdd lrsveetlkv erdqlkenlr etitrdlekq eelkivhmhl kehqetidkl
1741  rgivsektne isnmqkdleh sndalkaqdl kiqeelriah mhlkeqqeti dklrgivsek
```

-continued

```
1801  tdklsnmqkd  lensnaklqe  kiqelkaneh  qlitlkkdvn  etqkkvseme  qlkkqikdqs 1861  ltlskleien  lnlaqklhen  leemksvmke  rdnlrrveet  lklerdqlke  slqetkardl 1921  eiqqelktar  mlskehketv  dklrekisek  tiqisdiqkd  ldkskdelqk  kiqelqkkel 1981  qllrvkedvn  mshkkineme  qlkkqfeaqn  lsmqsvrmdn  fqltkklhes  leeirivake 2041  rdelrrikes  lkmerdqfia  tlremiardr  qnhqvkpekr  llsdgqqhlt  eslrekcsri 2101  kellkrysem  ddhyeclnrl  sldlekeief  qkelsmrvka  nlslpylqtk  hieklftanq 2161  rcsmefhrim  kklkyvlsyv  tkikeeqhes  inkfemdfid  evekqkelli  kiqhlqqdcd 2221  vpsrelrdlk  lnqnmdlhie  eilkdfsese  fpsiktefqq  vlsnrkemtq  fleewlntrf 2281  dieklkngiq  kendricqvn  nffnnriiai  mnestefeer  satiskeweq  dlkslkekne 2341  klfknyqtlk  tslasgaqvn  pttqdnknph  vtsratqltt  ekirelensl  heakesamhk 2401  eskiikmqke  levtndiiak  lqakvhesnk  clektketiq  vlqdkvalga  kpykeeiedl 2461  kmklvkidle  kmknakefek  eisatkatve  yqkevirllr  enlrrsqqaq  dtsvisehtd 2521  pqpsnkpltc  gggsgivqnt  kalilksehi  rlekeisklk  qqneqlikqk  nellsnnqhl 2581  snevktwker  tlkreahkqv  tcenspkspk  vtgtaskkkq  itpsqckern  lqdpvpkesp 2641  kscffdsrsk  slpsphpvry  fdnsslglcp  evqnagaesv  dsqpgpwhas  sgkdvpeckt 2701  q
```

By "CENPE polynucleotide" is meant a polynucleotide encoding a CENPE polypeptide. An exemplary CENPE polynucleotide is provided at NCBI Accession No. NM_001813.2. The sequence at NCBI Accession No. NM_001813.2 is provided below: SEQ ID NO: 2

```
   1  taaatttaaa  ggcggggcgg  cctgtgagcc  ctgaagtgcc  ggccgcggag  ggtcctggcc 61  attttcctgg  gaccagttca  gcctgatagg  atggcggagg  aaggagccgt  ggccgtctgc 121  gtgcgagtgc  ggccgctgaa  cagcagagaa  gaatcacttg  gagaaactgc  ccaagtttac 181  tggaaaactg  acaataatgt  catttatcaa  gttgatgaa   gtaaatcctt  caattttgat 241  cgtgtctttc  atggtaatga  aactaccaaa  aatgtgtatg  aagaaatagc  agcaccaatc 301  atcgattctg  ccatacaagg  ctacaatggt  actatatttg  cctatggaca  gactgcttca 361  ggaaaaacat  ataccatgat  gggttcagaa  gatcatttgg  gagttatacc  cagggcaatt 421  catgacattt  tccaaaaaat  taagaagttt  cctgataggg  aatttctctt  acgtgtatct 481  tacatggaaa  tatacaatga  aaccattaca  gatttactct  gtggcactca  aaaaatgaaa 541  cctttaatta  ttcgagaaga  tgtcaatagg  aatgtgtatg  ttgctgatct  cacagaagaa 601  gttgtatata  catcagaaat  ggctttgaaa  tggattacaa  agggagaaaa  gagcaggcat 661  tatggagaaa  caaaaatgaa  tcaaagaagc  agtcgttctc  ataccatctt  taggatgatt 721  ttggaaagca  gagagaaggg  tgaaccttct  aattgtgaag  gatctgttaa  ggtatcccat 781  ttgaatttgg  ttgatcttgc  aggcagtgaa  agagctgctc  aaacaggcgc  tgcaggtgtg 841  cggctcaagg  aaggctgtaa  tataaatcga  agcttattta  ttttgggaca  agtgatcaag 901  aaacttagtg  atggacaagt  tggtggtttc  ataaattatc  gagatagcaa  gttaacacga 961  attctccaga  attccttggg  aggaaatgca  aagacacgta  ttatctgcac  aattactcca 1021  gtatcttttg  atgaaacact  tactgctctc  cagtttgcca  gtactgctaa  atatatgaag 1081  aatactcctt  atgttaatga  ggtatcaact  gatgaagctc  tcctgaaaag  gtatagaaaa 1141  gaaataatgg  atcttaaaaa  acaattagag  gaggtttctt  tagagacgcg  ggctcaggca
```

-continued

```
1201  atggaaaaag accaattggc caacttttg gaagaaaaag atttgcttca gaaagtacag
1261  aatgagaaaa ttgaaaactt aacacggatg ctggtgacct cttcttccct cacgttgcaa
1321  caggaattaa aggctaaaag aaaacgaaga gttacttggt gccttggcaa aattaacaaa
1381  atgaagaact caaactatgc agatcaattt aatataccaa caaatataac aacaaaaaca
1441  cataagcttt ctataaattt attacgagaa attgatgaat ctgtctgttc agagtctgat
1501  gttttcagta cactcttga tacattaagt gagatagaat ggaatccagc aacaaagcta
1561  ctaaatcagg agaatataga aagtgagttg aactcacttc gtgctgacta tgataatctg
1621  gtattagact atgaacaact acgaacagaa aaagaagaaa tggaattgaa attaaaagaa
1681  aagaatgatt tggatgaatt tgaggctcta gaaagaaaaa ctaaaaaaga tcaagagatg
1741  caactaattc atgaaatttc gaacttaaag aatttagtta agcatgcaga agtatataat
1801  caagatcttg agaatgaact cagttcaaaa gtagagctgc ttagagaaaa ggaagaccag
1861  attaagaagc tacaggaata catagactct caaaagctag aaaatataaa aatggacttg
1921  tcatactcat tggaaagcat tgaagaccca aaacaaatga agcagactct gtttgatgct
1981  gaaactgtag cccttgatgc aagagagaa tcagcctttc ttagaagtga aaatctggag
2041  ctgaaggaga aaatgaaaga acttgcaact acatacaagc aaatggaaaa tgatattcag
2101  ttatatcaaa gccagttgga ggcaaaaaag aaaatgcaag ttgatctgga aaagaatta
2161  caatctgctt ttaatgagat aacaaaactc acctcccctta tagatggcaa agttccaaaa
2221  gatttgctct gtaatttgga attggaagga agattactg atcttcagaa agaactaaat
2281  aaagaagttg aagaaaatga agctttgcgg gaagaagtca tttgctttc agaattgaaa
2341  tctttaccct ctgaagtaga aaggctgagg aaagagatac aagacaaatc tgaagagctc
2401  catataataa catcagaaaa agataaattg ttttctgaag tagttcataa ggagagtaga
2461  gttcaaggtt tacttgaaga aattgggaaa acaaaagatg acctagcaac tacacagtcg
2521  aattataaaa gcactgatca agaattccaa aatttcaaaa cccttcatat ggactttgag
2581  caaaagtata agatggtcct tgaggagaat gagagaatga atcaggaaat agttaatctc
2641  tctaaagaag cccaaaaatt tgattcgagt ttgggtgctt tgaagaccga gctttcttac
2701  aagacccaag aacttcagga gaaaacacgt gaggttcaag aaagactaaa tgagatggaa
2761  cagctgaagg aacaattaga aaatagagat tctacgctgc aaactgtaga aagggagaaa
2821  acactgatta ctgagaaact gcagcaaact ttagaagaag taaaaacttt aactcaagaa
2881  aaagatgatc taaaacaact ccaagaaagc ttgcaaattg agagggacca actcaaaagt
2941  gatattcacg atactgttaa catgaatata gatactcaag aacaattacg aaatgctctt
3001  gagtctctga acaacatca agaaacaatt aatacactaa atcgaaaat ttctgaggaa
3061  gtttccagga atttgcatat ggaggaaaat acaggagaaa ctaaagatga atttcagcaa
3121  aagatggttg gcatagataa aaaacaggat ttggaagcta aaaatacca aacactaact
3181  gcagatgtta aggataatga gataattgag caacaaagga agatattttc tttaatacag
3241  gagaaaaatg aactccaaca aatgttagag agtgttatag cagaaaagga acaattgaag
3301  actgacctaa aggaaaatat tgaaatgacc attgaaaacc aggaagaatt aagacttctt
3361  ggggatgaac ttaaaagcaa acaagagata gttgcacaag aaaagaacca tgccataaag
3421  aaagaggag agctttctag gacctgtgac agactggcag aagttgaaga aaaactaaag
3481  gaaagagcc agcaactcca agaaaaacag caacaacttc ttaatgtaca agaagagatg
3541  agtgagatgc agaaaaagat taatgaaata gagaatttaa agaatgaatt aaagaacaaa
3601  gaattgacat tggaacatat ggaaacagag aggcttgagt tggctcagaa acttaatgaa
```

-continued

```
3661   aattatgagg aagtgaaatc tataaccaaa gaaagaaaag ttctaaagga attacagaag
3721   tcatttgaaa cagagagaga ccaccttaga ggatatataa gagaaattga agctacaggc
3781   ctacaaacca aagaagaact aaaaattgct catattcacc taaaagaaca ccaagaaact
3841   attgatgaac taagaagaag cgtatctgag aagacagctc aaataataaa tactcaggac
3901   ttagaaaaat cccataccaa attacaagaa gagatcccag tgcttcatga ggaacaagag
3961   ttactgccta atgtgaaaga agtcagtgag actcaggaaa caatgaatga actggagtta
4021   ttaacagaac agtccacaac caaggactca acaacactgg caagaataga aatggaaagg
4081   ctcaggttga atgaaaaatt tcaagaaagt caggaagaga taaaatctct aaccaaggaa
4141   agagacaacc ttaaaacgat aaaagaagcc cttgaagtta acatgacca gctgaaagaa
4201   catattagag aaactttggc taaaatccag gagtctcaaa gcaaacaaga acagtcctta
4261   aatatgaaag aaaaagacaa tgaaactacc aaaatcgtga gtgagatgga gcaattcaaa
4321   cccaaagatt cagcactact aaggatagaa atagaaatgc tcggattgtc caaaagactt
4381   caagaaagtc atgatgaaat gaaatctgta gctaaggaga aagatgacct acagaggctg
4441   caagaagttc ttcaatctga aagtgaccag ctcaaagaaa acataaaaga aattgtagct
4501   aaacacctgg aaactgaaga ggaacttaaa gttgctcatt gttgcctgaa agaacaagag
4561   gaaactatta atgagttaag agtgaatctt tcagagaagg aaactgaaat atcaaccatt
4621   caaaagcagt tagaagcaat caatgataaa ttacagaaca agatccaaga gatttatgag
4681   aaagaggaac aatttaatat aaaacaaatt agtgaggttc aggaaaaagt gaatgaactg
4741   aaacaattca aggagcatcg caaagccaag gattcagcac tacaaagtat agaaagtaag
4801   atgctcgagt tgaccaacag acttcaagaa agtcaagaag aaatacaaat tatgattaag
4861   gaaaagagg aaatgaaaag agtacaggag gcccttcaga tagagagaga ccaactgaaa
4921   gaaaacacta agaaattgt agctaaaatg aaagaatctc aagaaaaga atatcagttt
4981   cttaagatga cagctgtcaa tgagactcag gagaaaatgt gtgaaataga acacttgaag
5041   gagcaatttg agacccagaa gttaaacctg gaaaacatag aaacggagaa tataaggttg
5101   actcagatac tacatgaaaa ccttgaagaa atgagatctg taacaaaaga aagagatgac
5161   cttaggagtg tggaggagac tctcaaagta gagagagacc agctcaagga aaaccttaga
5221   gaaactataa ctagagaccct agaaaaacaa gaggagctaa aaattgttca catgcatctg
5281   aaggagcacc aagaaactat tgataaacta agagggattg tttcagagaa aacaaatgaa
5341   atatcaaata tgcaaaagga cttagaacac tcaaatgatg ccttaaaagc acaggatctg
5401   aaaatacaag aggaactaag aattgctcac atgcatctga agagcagca ggaaactatt
5461   gacaaactca gaggaattgt ttctgagaag acagataaac tatcaaatat gcaaaagat
5521   ttagaaaatt caaatgctaa attacaagaa aagattcaag aacttaaggc aaatgaacat
5581   caacttatta cgttaaaaaa agatgtcaat gagacacaga aaaaagtgtc tgaaatggag
5641   caactaaaga aacaaataaa agaccaaagc ttaactctga gtaaattaga aatagagaat
5701   ttaaatttgg ctcagaaact tcatgaaaac cttgaagaaa tgaaatctgt aatgaaagaa
5761   agagataatc taagaagagt agaggagaca ctcaaactgg agagagacca actcaaggaa
5821   agcctgcaag aaaccaaagc tagagatctg gaaatacaac aggaactaaa aactgctcgt
5881   atgctatcaa agaacacaa agaaactgtt gataaactta gagaaaaaat ttcagaaaag
5941   acaattcaaa tttcagacat tcaaaaggat ttagataaat caaaagatga attacagaaa
6001   aagatccaag aacttcagaa aaaagaactt caactgctta gagtgaaaga agatgtcaat
```

-continued

```
6061  atgagtcata aaaaaattaa tgaaatggaa cagttgaaga agcaatttga ggcccaaaac
6121  ttatctatgc aaagtgtgag aatggataac ttccagttga ctaagaaact tcatgaaagc
6181  cttgaagaaa taagaattgt agctaaagaa agagatgagc taaggaggat aaaagaatct
6241  ctcaaaatgg aaagggacca attcatagca accttaaggg aaatgatagc tagagaccga
6301  cagaaccacc aagtaaaacc tgaaaaaagg ttactaagtg atggacaaca gcaccttacg
6361  gaaagcctga gagaaaagtg ctctagaata aaagagcttt tgaagagata ctcagagatg
6421  gatgatcatt atgagtgctt gaatagattg tctcttgact tggagaagga aattgaattc
6481  caaaagagc tttcaatgag agttaaagca aacctctcac ttccctattt acaaaccaaa
6541  cacattgaaa aacttttttac tgcaaaccag atgctcca tggaattcca cagaatcatg
6601  aagaaactga agtatgtgtt aagctatgtt acaaaaataa aagaagaaca catgaatcc
6661  atcaataaat ttgaaatgga ttttattgat gaagtggaaa agcaaaagga attgctaatt
6721  aaaatacagc accttcaaca agattgtgat gtaccatcca gagaattaag ggatctcaaa
6781  ttgaaccaga atatggatct acatattgag gaaattctca agatttctc agaaagtgag
6841  ttccctagca taaagactga atttcaacaa gtactaagta ataggaaaga aatgacacag
6901  tttttggaag agtggttaaa tactcgtttt gatatagaaa agcttaaaaa tggcatccag
6961  aaagaaaatg ataggatttg tcaagtgaat aacttctttta ataacagaat aattgccata
7021  atgaatgaat caacagagtt tgaggaaaga agtgctacca tatccaaaga gtgggaacag
7081  gacctgaaat cactgaaaga gaaaaatgaa aaactattta aaaactacca acattgaag
7141  acttccttgg catctggtgc ccaggttaat cctaccacac aagacaataa gaatcctcat
7201  gttacatcaa gagctacaca gttaaccaca gagaaaattc gagagctgga aaattcactg
7261  catgaagcta agaaagtgc tatgcataag gaaagcaaga ttataaagat gcagaaagaa
7321  cttgaggtga ctaatgacat aatagcaaaa cttcaagcca aagttcatga atcaaataaa
7381  tgccttgaaa aaacaaaaga gacaattcaa gtacttcagg acaaagttgc tttaggagct
7441  aagccatata agaagaaat tgaagatctc aaaatgaagc ttgtgaaaat agacctagag
7501  aaaatgaaaa atgccaaaga atttgaaaag gaaatcagtg ctacaaaagc cactgtagaa
7561  tatcaaaagg aagttataag gctattgaga gaaaatctca gaagaagtca acaggcccaa
7621  gataccctcag tgatatcaga acatactgat cctcagcctt caaataaacc cttaacttgt
7681  ggaggtggca gcggcattgt acaaaacaca aaagctctta ttttgaaaag tgaacatata
7741  aggctagaaa agaaaatttc taagttaaag cagcaaaatg aacagctaat aaaacaaaag
7801  aatgaattgt taagcaataa tcagcatctt tccaatgagg tcaaaacttg gaaggaaaga
7861  acccttaaaa gagaggctca caaacaagta acttgtgaga attctccaaa gtctcctaaa
7921  gtgactggaa cagcttctaa aaagaaacaa attacaccct ctcaatgcaa ggaacggaat
7981  ttacaagatc ctgtgccaaa ggaatcacca aaatcttgtt tttttgatag ccgatcaaag
8041  tctttaccat cacctcatcc agttcgctat tttgataact caagtttagg cctttgtcca
8101  gaggtgcaaa atgcaggagc agagagtgtg gattctcagc caggtccttg gcacgcctcc
8161  tcaggcaagg atgtgcctga gtgcaaaact cagtagactc ctctttgtca cttctctgga
8221  gatccagcat tccttatttg gaaatgactt tgtttatgtg tctatccctg gtaatgatgt
8281  tgtagtgcag cttaatttca attcagtctt tactttgcca ctagagttga aagataaggg
8341  aacaggaaat gaatgcattg tggtaattta gaatggtgat agcaatacct tcttcttgca
8401  tatggtaata cttttaaaag ttgaattgtt ttatttattt gtatattttg taaagaataa
8461  agttattgaa agaaatgtaa agttatctac atgacttagc atattccaaa gcataataca
```

```
8521  tacattaata taaaacatca ttttattaac aaaattgtaa atgtttttaa taccttacac 8581  attcaataaa tgtttagtag ttctgaatca ccaaaaaaaa aaaaaaaaaa
```

By "CYP2S1 polypeptide" is meant a polypeptide or fragment thereof having at least about 85% amino acid identity to NCBI Accession No. NP_085125.1 and having a biological activity of a CYP2S1 (cytochrome P450, family 2) polypeptide. Biological activities of a CYP2S1 polypeptide include steroid hydroxylase activity, oxidoreductase activity, and extrahepatic xenobiotic metabolism. The sequence at NCBI Accession No. NP_085125.1 is shown below: SEQ ID NO: 3

```
  1  meatgtwall lalallllt lalsgtrarg hlppgptplp llgnllqlrp galysglmrl 61  skkygpvfti ylgpwrpvvv lvgqeavrea lggqaeefsg rgtvamlegt fdghgvffsn 121  gerwrqlrkf tmlalrdlgm gkregeeliq aearclvetf qgtegrpfdp slllaqatsn 181  vvcsllfglr fsyedkefqa vvraaggtll gvssqggqty emfswflrpl pgphkqllhh 241  vstlaaftvr qvqqhqgnld asgpardlvd afllkmaqee qnpgteftnk nmlmtviyll 301  fagtmtvstt vgytllllmk yphvqkwvre elnrelgagq apslgdrtrl pytdavlhea 361  qrllalvpmg iprtlmrttr frgytlpqgt evfpllgsil hdpnifkhpe efnpdrflda 421  dgrfrkheaf lpfslgkrvc lgeglakael flffttilqa fslespcppd tlslkptvsg 481  lfnippafql qvrptdlhst tqtr
```

By "CYP2S1 polynucleotide" is meant a polynucleotide encoding a CYP2S1 polypeptide. An exemplary CYP2S1 polynucleotide sequence is provided at NCBI Accession No. NM_030622.7. The exemplary sequence provided at NCBI Accession No. NM_030622.7 is reproduced below: SEQ ID NO: 4

```
  1  cctaactagc ccagccgcgc ggagcgcctg ggagaggaga aggagccgac ctgccgagat 61  ggaggcgacc ggcacctggg cgctgctgct ggcgctggcg ctgctcctgc tgctgacgct 121  ggcgctgtcc gggaccaggg cccgaggcca cctgccccc gggcccacgc cgctaccact 181  gctgggaaac ctcctgcagc tacggcccgg ggcgctgtat tcagggctca tgcggctgag 241  taagaagtac ggaccggtgt tcaccatcta cctgggaccc tggcggcctg tggtggtcct 301  ggttgggcag gaggctgtgc gggaggccct gggaggtcag gctgaggagt tcagcggccg 361  gggaaccgta gcgatgctgg aagggacttt tgatggccat ggggttttct tctccaacgg 421  ggagcggtgg aggcagctga ggaagtttac catgcttgct ctgcgggacc tgggcatggg 481  gaagcgagaa ggcgaggagc tgatccaggc ggaggcccgg tgtctggtgg agacattcca 541  ggggacagaa ggacgcccat tcgatccctc cctgctgctg cccaggcca cctccaacgt 601  agtctgctcc ctcctctttg gctccgcctt ctcctatgag gataaggagt tccaggccgt 661  ggtccgggca gctggtggta ccctgctggg agtcagctcc caggggggtc agacctacga 721  gatgttctcc tggttcctgc ggcccctgcc aggccccac aagcagctcc tccaccgt 781  cagcaccttg gctgccttca cagtccggca ggtgcagcag caccagggga acctggatgc 841  ttcgggcccc gcacgtgacc ttgtcgatgc cttcctgctg aagatggcac aggaggaaca 901  aaacccaggc acagaattca ccaacaagaa catgctgatg acagtcattt atttgctgtt 961  tgctgggacg atgacggtca gcaccacggt cggctatacc ctcctgctcc tgatgaaata
```

-continued

```
1021  ccctcatgtc caaaagtggg tacgtgagga gctgaatcgg gagctggggg ctggccaggc 1081  accaagccta ggggaccgta cccgcctccc ttacaccgac gcggttctgc atgaggcgca 1141  gcggctgctg gcgctggtgc ccatgggaat accccgcacc ctcatgcgga ccacccgctt 1201  ccgagggtac accctgcccc agggcacgga ggtcttcccc ctccttggct ccatcctgca 1261  tgaccccaac atcttcaagc acccagaaga gttcaaccca daccgtttcc tggatgcaga 1321  tggacggttc aggaagcatg aggcgttcct gcccttctcc ttagggaagc gtgtctgcct 1381  tggagagggc ctggcaaaag cggagctctt cctcttcttc accaccatcc tacaagcctt 1441  ctccctggag agcccgtgcc cgccggacac cctgagcctc aagcccaccg tcagtggcct 1501  tttcaacatt cccccagcct tccagctgca agtccgtccc actgaccttc actccaccac 1561  gcagaccaga tgaaggaagg caacttggaa gtggtgggtg cccaggacgg tgcctccagc 1621  ctcaacagtg ggcatggaca gggttaatgt ctccagagtg tacactgcag gcagccacat 1681  ttacacgcct gcagttgttt tccggagtct gtcccacggc ccacacgctc acttgactca 1741  tgctgctaag atgcacaacc gcacacccat acacaactac aagggccaca aagcaactgc 1801  tgggttagct ttccacagac ataaatatag tccatctgca atcacaagca catagccagg 1861  taacccacca actccctgg atctgcagcc cacacgtggg agtctggctg tcaccttcac 1921  aagccacaga aacggccaca catgttcaca gctcacacgc cctctccatt catcgaactt 1981  ctcagtgtcc ctgtccctgg tgcctggcac agggaacagc atgcccctc cggggtcatg 2041  ccacccgag actgtcgctg tctatggccc caactcatgc tccctctctt ggctacacca 2101  ctctcccagc ctgtgaccac cgatgtccac acaccccaa ccacttgtcc acacagctac 2161  ccacgtacga catcgtcctg gctccccaga gtatcttccc actgagacac gccgccccca 2221  cagaggcaca gtccccagcc acctctgcaa ctgcagccct cagtcacccc tttttaagca 2281  ccctgattct accaaatgca aacacatctg ggtctgcgat tatgcacaga gactttggac 2341  atacgaggac cctcagaccg gaggaacacc tgcccaaccc caacacgtgc ttatgtaacc 2401  acgtggaaag cggcccctgc tgcccctcca cacacacata cacactcact gatctacagc 2461  ccctgttcgg cgtcagagtc cccactagac ccagtggaag gggttagaga ccaagtaggg 2521  gccagtttcc aattcaccct gtcagggagt gagccggatc tgacgttcct tgtgacttaa 2581  gggtccggct tgggaattaa agtttgtttc tggcctttag cctaaaaaaa aaaaaaaaaa 2641  aaaaaaaaaa aaaaaaaaaa
```

By "capture reagent" is meant a reagent that specifically binds a nucleic acid molecule or polypeptide to select or isolate the nucleic acid molecule or polypeptide.

By "decreases" is meant a negative alteration of at least 10%, 25%, 50%, 75%, 100%, 200%, 300%, 400%, 500%, 1000%, or more.

By "detect" refers to identifying the presence, absence, level, or concentration of an agent.

By "detectable" is meant a moiety that when linked to a molecule of interest renders the latter detectable. Such detection may be via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. Preferably, the animal is a mammal. More preferably, the mammal is a human.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "expression" as used herein is defined as the transcription and/or translation of a particular nucleotide sequence driven by its promoter.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "FCER1A polypeptide" is meant a polypeptide or fragment thereof having at least about 85% amino acid identity to NCBI Accession No. NP_001992.1 and having a biological activity of a FCER1A (high affinity IgE receptor FcɛR1) polypeptide. Biological activities of a FCER1A polypeptide include IgE receptor activity and IgE binding. The sequence at NCBI Accession No. NP_001992.1 is shown below: SEQ ID NO: 5

```
  1  mapamesptl  lcvallffap  dgvlavpqkp  kvslnppwnr  ifkgenvtlt  cngnnffevs
 61  stkwfhngsl  seetnsslni  vnakfedsge  ykcqhqqvne  sepvylevfs  dwlllgasae
121  vvmegqplfl  rchgwrnwdv  ykviyykdge  alkywyenhn  isitnatved  sgtyyctgkv
181  wqldyesepl  nitvikapre  kywlqffipl  lvvilfavdt  glfistqqqv  tfllkikrtr
241  kgfrllnphp  kpnpknn
```

By "FCER1A polynucleotide" is meant a polynucleotide encoding a FCER1A polypeptide. An exemplary FCER1A polynucleotide sequence is provided at NCBI Accession No. NM_002001.3. The exemplary sequence provided at NCBI Accession No. NM_002001.3 is reproduced below: SEQ ID NO: 6

```
  1  tactaagagt  ctccagcatc  ctccacctgt  ctaccaccga  gcatgggcct  atatttgaag
 61  ccttagatct  ctccagcaca  gtaagcacca  ggagtccatg  aagaagatgg  ctcctgccat
121  ggaatcccct  actctactgt  gtgtagcctt  actgttcttc  gctccagatg  gcgtgttagc
181  agtccctcag  aaacctaagg  tctccttgaa  ccctccatgg  aatagaatat  ttaaaggaga
241  gaatgtgact  cttacatgta  atgggaacaa  tttctttgaa  gtcagttcca  ccaaatggtt
301  ccacaatggc  agcctttcag  aagagacaaa  ttcaagtttg  aatattgtga  atgccaaatt
361  tgaagacagt  ggagaataca  aatgtcagca  ccaacaagtt  aatgagagtg  aacctgtgta
421  cctggaagtc  ttcagtgact  ggctgctcct  tcaggcctct  gctgaggtgg  tgatggaggg
481  ccagccccctc  ttcctcaggt  gccatggttg  gaggaactgg  gatgtgtaca  aggtgatcta
541  ttataaggat  ggtgaagctc  tcaagtactg  gtatgagaac  cacaacatct  ccattacaaa
601  tgccacagtt  gaagacagtg  gaacctacta  ctgtacgggc  aaagtgtggc  agctggacta
661  tgagtctgag  cccctcaaca  ttactgtaat  aaaagctccg  cgtgagaagt  actggctaca
721  attttttatc  ccattgttgg  tggtgattct  gtttgctgtg  gacacaggat  tatttatctc
781  aactcagcag  caggtcacat  ttctcttgaa  gattaagaga  accaggaaag  gcttcagact
841  tctgaaccca  catcctaagc  caaacccaa  aaacaactga  tataattact  caagaaatat
901  ttgcaacatt  agttttttc  cagcatcagc  aattgctact  caattgtcaa  acacagcttg
961  caatatacat  agaaacgtct  gtgctcaagg  atttatagaa  atgcttcatt  aaactgagtg
```

```
1021  aaactggtta agtggcatgt aatagtaagt gctcaattaa cattggttga ataaatgaga 1081  gaatgaatag attcatttat tagcatttgt aaaagagatg ttcaatttca ataaaataaa 1141  tataaaacca tgtaacagaa tgcttctgag taaaaaaaaa aaaaaaaaaa aaaaaaaa
```

By "genotype" is meant the genetic composition of a cell, organism, or individual.

By "IL1RN polypeptide" is meant a polypeptide or fragment thereof having at least about 85% amino acid identity to NCBI Accession No. NP_776214.1 and having a biological activity of a IL1RN (interleukin 1 receptor antagonist) polypeptide. Biological activities of a IL1RN polypeptide include cytokine activity, interleukin-1 receptor binding, and interleukin-1 receptor antagonist activity. The sequence at NCBI Accession No. NP_776214.1 is shown below: SEQ ID NO: 7

```
  1  meicrglrsh litlllflfh seticrpsgr ksskmqafri wdvnqktfyl rnnqlvagyl 61  qgpnvnleek idvvpiepha lflgihggkm clscvksgde trlqleavni tdlsenrkqd 121  krfafirsdf gpttsfesaa cpgwflctam eadqpvsltn mpdegvmvtk fyfqede
```

By "IL1RN polynucleotide" is meant a polynucleotide encoding a IL1RN polypeptide. An exemplary IL1RN polynucleotide sequence is provided at NCBI Accession No. NM_173842.2. The exemplary sequence provided at NCBI Accession No. NM 173842.2 is reproduced below: SEQ ID NO: 8

```
   1  atttctttat aaaccacaac tctgggcccg caatggcagt ccactgcctt gctgcagtca 61  cagaatggaa atctgcagag gcctccgcag tcacctaatc actctcctcc tcttcctgtt 121  ccattcagag acgatctgcc gaccctctgg gagaaaatcc agcaagatgc aagccttcag 181  aatctgggat gttaaccaga agaccttcta tctgaggaac aaccaactag ttgctggata 241  cttgcaagga ccaaatgtca atttagaaga aaagatagat gtggtaccca ttgagcctca 301  tgctctgttc ttgggaatcc atggagggaa gatgtgcctg tcctgtgtca agtctggtga 361  tgagaccaga ctccagctgg aggcagttaa catcactgac ctgagcgaga acagaaagca 421  ggacaagcgc ttcgccttca tccgctcaga cagtggcccc accaccagtt ttgagtctgc 481  cgcctgcccc ggttggttcc tctgcacagc gatggaagct gaccagcccg tcagcctcac 541  caatatgcct gacgaaggcg tcatggtcac caaattctac ttccaggagg acgagtagta 601  ctgcccaggc ctgcctgttc ccattcttgc atggcaagga ctgcagggac tgccagtccc 661  cctgcccag ggctcccggc tatggggca ctgaggacca gccattgagg ggtggaccct 721  cagaaggcgt cacaacaacc tggtcacagg actctgcctc ctcttcaact gaccagcctc 781  catgctgcct ccagaatggt ctttctaatg tgtgaatcag agcacagcag ccctgcaca 841  aagcccttcc atgtcgcctc tgcattcagg atcaaacccc gaccacctgc ccaacctgct 901  ctcctcttgc cactgcctct tcctccctca ttccaccttc ccatgccctg gatccatcag 961  gccacttgat gaccccaac caagtggctc ccacaccctg ttttacaaaa aagaaaagac 1021  cagtccatga gggaggtttt taagggtttg tggaaaatga aaattaggat ttcatgattt 1081  ttttttttca gtccccgtga aggagagccc ttcatttgga gattatgttc tttcggggag 1141  aggctgagga cttaaaatat tcctgcattt gtgaaatgat ggtgaaagta agtggtagct 1201  tttcccttct ttttcttctt tttttgtgat gtcccaactt gtaaaaatta aaagttatgg
```

```
1261  tactatgtta gccccataat ttttttttc cttttaaaac acttccataa tctggactcc 1321  tctgtccagg cactgctgcc cagcctccaa gctccatctc cactccagat tttttacagc 1381  tgcctgcagt actttacctc ctatcagaag tttctcagct cccaaggctc tgagcaaatg 1441  tggctcctgg gggttctttc ttcctctgct gaaggaataa attgctcctt gacattgtag 1501  agcttctggc acttggagac ttgtatgaaa gatggctgtg cctctgcctg tctccccac 1561  cgggctggga gctctgcaga gcaggaaaca tgactcgtat atgtctcagg tccctgcagg 1621  gccaagcacc tagcctcgct cttggcaggt actcagcgaa tgaatgctgt atatgttggg 1681  tgcaaagttc cctacttcct gtgacttcag ctctgtttta caataaaatc ttgaaaatgc 1741  ctaaaaaaaa aaaaaaaaa aaaaaaaaa aaaaaaaaa aaaa
```

By "increases" is meant a positive alteration of at least 10%, 25%, 50%, 75%, 100%, 200%, 300%, 400%, 500%, 1000%, or more.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

By "marker profile" is meant a characterization of the expression or expression level of two or more polypeptides or polynucleotides "Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

By "MTHFD2 polypeptide" is meant a polypeptide or fragment thereof having at least about 85% amino acid identity to NCBI Accession No. NP_006627.2 and having a biological activity of a MTHFD2 (methylenetetrahydrofolate dehydrogenase (NADP+ dependent) 2, methenyltetrahydrofolate cyclohydrolase) polypeptide. Biological activities of a MTHFD2 polypeptide include methylenetetrahydrofolate dehydrogenase activity and methenyltetrahydrofolate cyclohydrolase activity. The sequence at NCBI Accession No. NP_006627.2 is shown below: SEQ ID NO: 9

```
  1  maatslmsal aarllqpahs cslrlrpfhl aavrneavvi sgrklaqqik qevrqeveew 61  vasgnkrphl svilvgenpa shsyvlnktr aaavvginse timkpasise eellnlinkl 121  nnddnvdgll vqlplpehid erricnavsp dkdvdgfhvi nvgrmcldqy smlpatpwgv 181  weiikrtgip tlgknvvvag rsknvgmpia mllhtdgahe rpggdatvti shrytpkeql 241  kkhtiladiv isaagipnli tadmikegaa vidvginrvh dpvtakpklv gdvdfegvrq 301  kagyitpvpg gvgpmtvaml mkntiiaakk vlrleerevl kskelgvatn
```

By "MTHFD2 polynucleotide" is meant a polynucleotide encoding an MTHFD2 polypeptide. An exemplary MTHFD2 polynucleotide is provided at NCBI Accession No. NM_006636.3. The sequence at NCBI Accession No. NM_006636.3 is provided below: SEQ ID NO: 10

```
  1  ggggcctgcc acgaggccgc agtataaccg cgtggcccgc gcgcgcgctt ccctcccggc 61  gcagtcaccg gcgcggtcta tggctgcgac ttctctaatg tctgctttgg ctgcccggct 121  gctgcagccc gcgcacagct gctcccttcg ccttcgccct ttccacctcg cggcagttcg 181  aaatgaagct gttgtcattt ctggaaggaa actggcccag cagatcaagc aggaagtgcg 241  gcaggaggta gaagagtggg tggcctcagg caacaaacgg ccacacctga gtgtgatcct 301  ggttggcgag aatcctgcaa gtcactccta tgtcctcaac aaaaccaggg cagctgcagt 361  tgtgggaatc aacagtgaga caattatgaa accagcttca atttcagagg aagaattgtt 421  gaatttaatc aataaactga ataatgatga taatgtagat ggcctccttg ttcagttgcc
```

```
 481   tcttccagag catattgatg agagaaggat ctgcaatgct gtttctccag acaaggatgt
 541   tgatggcttt catgtaatta atgtaggacg aatgtgtttg gatcagtatt ccatgttacc
 601   ggctactcca tggggtgtgt gggaaataat caagcgaact ggcattccaa ccctagggaa
 661   gaatgtggtt gtggctggaa ggtcaaaaaa cgttggaatg cccattgcaa tgttactgca
 721   cacagatggg gcgcatgaac gtcccggagg tgatgccact gttacaatat ctcatcgata
 781   tactcccaaa gagcagttga agaaacatac aattcttgca gatattgtaa tatctgctgc
 841   aggtattcca aatctgatca cagcagatat gatcaaggaa ggagcagcag tcattgatgt
 901   gggaataaat agagttcacg atcctgtaac tgccaaaccc aagttggttg gagatgtgga
 961   ttttgaagga gtcagacaaa aagctgggta tatcactcca gttcctggag gtgttggccc
1021   catgacagtg gcaatgctaa tgaagaatac cattattgct gcaaaaaagg tgctgaggct
1081   tgaagagcga gaagtgctga agtctaaaga gcttggggta gccactaatt aactactgtg
1141   tcttctgtgt cacaaacagc actccaggcc agctcaagaa gcaaagcagg ccaatagaaa
1201   tgcaatattt ttaatttatt ctactgaaat ggtttaaaat gatgccttgt atttattgaa
1261   agcttaaatg ggtgggtgtt tctgcacata cctctgcagt acctcaccag ggagcattcc
1321   agtatcatgc agggtcctgt gatctagcca ggagcagcca ttaacctagt gattaatatg
1381   ggagacatta ccatatggag gatggatgct tcactttgtc aagcacctca gttacacatt
1441   cgcctttct aggattgcat ttcccaagtg ctattgcaat aacagttgat actcatttta
1501   ggtaccaaac cttttgagtt caactgatca aaccaaagga aaagtgttgc tagagaaaat
1561   tagggaaaag gtgaaaaaga aaaatggta gtaattgagc agaaaaaaat taatttatat
1621   atgtattgat tggcaaccag atttatctaa gtagaactga attggctagg aaaaaagaaa
1681   aactgcatgt taatcatttt cctaagctgt cctttttgagg cttagtcagt ttattgggaa
1741   aatgtttagg attattcctt gctattagta ctcattttat gtatgttacc cttcagtaag
1801   ttctccccat tttagttttc taggactgaa aggattcttt tctacattat acatgtgtgt
1861   tgtcatattt ggcttttgct atatacttta acttcattgt taaattttg tattgtatag
1921   tttctttggt gtatcttaaa acctattttt gaaaaacaaa cttggcttga taatcatttg
1981   ggcagcttgg gtaagtacgc aacttacttt tccaccaaag aactgtcagc agctgcctgc
2041   ttttctgtga tgtatgtatc ctgttgactt ttccagaaat ttttaagag tttgagttac
2101   tattgaattt aatcagactt tctgattaaa gggttttctt tcttttttaa taaaacacat
2161   ctgtctggta tggtatgaat ttctgaaaaa aaaaaaaaaa aaaaaaaa
```

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein a "nucleic acid or oligonucleotide probe" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target gene of interest.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "quantitative trait" refer to a phenotype or characteristics of an individual that can be attributed to the effect two or more genes.

As used herein, "quantitative trait locus (QTL)" refers to a DNA sequence or segment located within the genome containing or linked to the genes that underlie a quantitative trait.

As used herein, "expression quantitative trait loci (eQTLs)" are genomic loci that regulate expression levels of mRNAs or proteins. The abundance of a gene transcript is directly modified by polymorphisms in regulatory elements that alter the level of a gene transcript. These can be mapped and the level of a gene transcript can be used as a quantitative trait. Mapping eQTLs is performed using standard QTL mapping methods that test the linkage between variation in expression and genetic polymorphisms. In one embodiment, eQTL is determined by statistical regression of the genotype of an SNP and the expression for the transcript.

By "reference" is meant a standard or control condition. In one embodiment, the level of gene expression in a tissue sample of a subject having GI Symptomatic ASD is compared to the gene expression in a tissue sample from a control subject.

"Sample" or "biological sample" as used herein means a biological material isolated from a subject, including any tissue, cell, fluid, or other material obtained or derived from the subject (e.g., a human). The biological sample may contain any biological material suitable for detecting the desired analytes, and may comprise cellular and/or non-cellular material obtained from the subject. In various embodiments, the biological sample may be obtained from the small bowel, stomach, or esophagus. In particular embodiments, the biological sample is a blood sample.

By "single nucleotide polymorphism" or "SNP" is meant a DNA sequence variation occurring when a single nucleotide in the genome differs between members of a biological species or paired chromosomes in an individual. SNPs are used as genetic markers for variant alleles.

By "SIGLEC17P polypeptide" is meant a polypeptide or fragment thereof having at least about 85% amino acid identity to GenBank No. AAF28901.1 and having a biological activity of a SIGLEC17P (sialic acid binding Ig-like lectin 17) polypeptide. SIGLEC17P polypeptide is also referred to herein as "SIGLECP3 polypeptide". Biological activities of a SIGLEC17P polypeptide include sialic acid binding. The sequence at GenBank No. AAF28901.1 is shown below: SEQ ID NO: 11

```
  1  erccrcccrc pccgqgprsg ckipagdarv rdgaggsvhl calfgllprv wlerfypclw
 61  plvpgkgqcr pgdsmatnns tqkvqketqg rfhllgdpsr nncslsirda rrrdngsyff
121  wvarrrtkfs ykysplsvyv talthrpdil ipeflksghp snltcsvpwv ceqgtppifs
181  wmsaaptslg prtlhsselt iiprpqdhgt nlicqvtfpg agvttertiq lsvswksgtv
241  eevvvlavgv vavkilllcl cliilsfhkk kavravevee nvyavmg
```

By "SIGLEC17P polynucleotide" or "SIGLECP3 polynucleotide" is meant a polynucleotide encoding a SIGLEC17P polypeptide. An exemplary SIGLEC17P polynucleotide is provided at NCBI Accession No. NR_002804. The sequence at NCBI Accession No. NR_002804 is provided below: SEQ ID NO: 12

```
CCAAGATCTCATGCTCCTCCCCACAGCCCTCTTCTCTGCTCACACAGGAA

GCCCAGGAAGCCTCTGCCTC

AGAGATGCTGCCGCTGCTGCTGCCGCTGCCCCTGCTGTGGGCAGGGCCCT

CGCTCAGGATGCAAGATTCC

GGCTGGAGATGCCAGAGTCCGTGACGGTGCAGGAGGGTCTGTGCATCTTT

GTGCACTGTTCGGTCTTCTA

CCTCGAGTATGGCTGGAAAGATTCTACCCCTGCTTATGGCCACTGGTTCC

GGGAAGGGGTCAGTGTAGAC

CAGGAGACTCCAGTGGCCACAAACAACTCAACTCAAAAAGTGCAGAAGGA

GACCCAGGGCCGATTCCACC

TCCTCGGTGATCCCTCAAGGAACAACTGCTCCCTGAGCATCAGAGACGCC

AGGAGGAGGGACAACGGTTC

ATACTTCTTTTGGGTGGCGAGAGGAAGAACAAAATTTAGTTACAAATATT

CCCCGCTCTCTGTGTATGTG

ACAGCCCTGACCCACAGGCCCGACATCCTCATCCCGGAGTTCCTAAAGTC

TGGCCATCCCAGCAACCTGA

CCTGCTCTGTGCCCTGGGTCTGTGAGCAGGGAACACCCCCCATCTTCTCC

TGGATGTCAGCTGCCCCCAC
```

-continued

```
CTCCCTGGGCCCCAGGACCCTCCACTCCTCAGTGCTCACGATCATCCCAC

GGCCTCAGGACCACGGCACC

AACCTCATCTGTCAGGTGACGTTCCCCGGAGCTGGTGTGACCACGGAGAG

AACCATCCAGCTCAGTGTCT

CCTGGAAATCAGGAACCGTGGAAGAGGTGGTTGTTTTGGCCGTGGGGTA

GTGGCTGTGAAGATCCTGCT

TCTCTGCCTTTGCCTCATCATCCTCAGGTAAGCACTGCCTGAAGACCAAG

GACAGGCATGGGGAGGGCAG

AGGACATGATGCTGAATCCCAGAATCTCAATCCTGGGGGTATGCAGACAG

TTTACGTGGTCCTGGGGCCA

GGCTGGAGGCTGAATTGGTGGTGAGAATTACACATGGGCCATTTGTGGTC

AGTTTGTGTCTGTCCCAACT

GAGGGCCAAATGCCAGGATGGGGAGCTTCCTGTTGTCATCAAGGAAGTCT

AGACCTGCTCTTCCTCCCTG

TGATCCCTCCAGCCTCTAGCAGGGCACAGGAAGTTGAGTTGGCTGCCCTT

TGCTCCCTTCATGTGGCCAC

ACTTACAGGTCCTTGTCTCTTCACTCAATGTCAGTTTCCACAAGAAGAAG

GCGGTGAGGGCAGTGGAGGT

TGAGGAGAATGTATATGCTGTCATGGGTTAATCTCTCAGGTGAGTGATGT

GGGCCTCTCACTCTTCAACA

TCCTGCTGGATAACTCCTCCACAATGGCCTCCAGGATTGCTCTGCCCATC

ATGGCCAAAGTTAAGCCAAC

TGTCTTCCTCCTCAAACCTACTTTTCCTGGGATGTGGGTTCTTCATCCTG

CAGATGACAAAGAGGCCTCA

TCTCTAAAGTCAGAACCTGGGTGTGGGTCTCCATCTTGACCCCCCTCCCT

TCTCTAGATCCCATAAATTA

CTAGCTCTTGTCCCTCCTTCTCCTAAGCAGGGCTCATCTTGATGCCCTTT

TCTCCATCCTGACCCTGGTC

ATTCTTGCGGCCTCACCTCTTCCCTGATCACTGAACCCTTTTCACCTCCT

GCCTCCATCTCTCCCCAACA

CAGGCCTCCAGACTGTACTTCCAGATGTCTCCTCATCCAGTTCCTCCACA

GTCTGAATGGCCATGTTTCC

TCTTCATTGCTGGAGAATGAAGTGCAAATGCCACTGCCTGGACTGAAGGC

CTTTCACGATCTGTCTTCTG

CTGGACTCTGCTCCTGATCCCCCTTCTCCTTGCATCACCCGAAGTCTCCC

TACACCCACCAGGCCAAGC

CTCTGTGATTCTGAGACTTTGCATGTGTAGTTACTTCTCCTGAAATGGCC

TTCCTCCCCATTCCTGCCAA

TCCAGGTCCTTATCATCCTTCAGGTTGTCTTAAATGTCATCCAGGTGTGT

GTATTTTTATGTAATCCTTG

TATGATATTAAGCGGAGATGTGGCATTTGTTCATTAATTTGTAGACATAT

TCAGTAACCATACTGAATAC

ATATAATGACTATGTGCCAGCATTTCCGTATGTGCAGAAGTTCATCAATA

GATATAGACTCAAAGAGCTC

TGTCATCAAGCTGTTGTTCTGAAGAGCAGAAGGATACAAATAAAAAGAAA

TAAGTAAAATAAAAAAAAAA

AAAAAAAAAA
```

By "specifically binds" is meant a compound or antibody that recognizes and binds a polypeptide of the invention, but which does not substantially recognize and bind other molecules in a sample.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaC, 75 mM trisodium citrate, and 1% SDS. In a more preferred embodiment, hybridization will occur at 37° C. C in 500 mM NaC, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS.

Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "target nucleic acid molecule" is meant a nucleic acid or biomarker of the sample that is to be detected.

By "TNFAIP3 polypeptide" is meant a polypeptide or fragment thereof having at least about 85% amino acid identity to NCBI Accession No. NP_006281.1 and having a biological activity of a TNFAIP3 (tumor necrosis factor, alpha-induced protein 3) polypeptide. Biological activities of a TNFAIP3 polypeptide include ubiquitin ligase activity and deubiquitinase activity. The sequence at NCBI Accession No. NP_006281.1 is shown below: SEQ ID NO: 13

```
  1  maeqvlpqal  ylsnmrkavk  irertpedif  kptngiihhf  ktmhrytlem  frtcqfcpqf
 61  reiihkalid  rniqatlesq  kklnwcrevr  klvalktngd  gnclmhatsq  ymwgvqdtdl
121  vlrkalfstl  ketdtrnfkf  rwqleslksq  efvetglcyd  trnwndewdn  likmastdtp
181  marsglqyns  leeihifvlc  nilrrpiivi  sdkmlrsles  gsnfaplkvg  giylplhwpa
241  qecyrypivl  gydshhfvpl  vtlkdsgpei  ravplvnrdr  grfedlkvhf  ltdpenemke
301  kllkeylmvi  eipvqgwdhg  tthlinaakl  deanlpkein  lvddyfelvq  heykkwqens
361  eqgrreghaq  npmepsvpql  slmdvkcetp  ncpffmsvnt  qplchecser  rqknqnklpk
421  lnskpgpegl  pgmalgasrg  eayeplawnp  eestggphsa  pptapspflf  settamkcrs
481  pgcpftlnvq  hngfcerchn  arqlhashap  dhtrhldpgk  cqaclqdvtr  tfngicstcf
541  krttaeasss  lstslppsch  qrsksdpsrl  vrspsphsch  ragndapagc  lsqaartpgd
601  rtgtskcrka  gcvyfgtpen  kgfctlcfie  yrenkhfaaa  sgkvsptasr  fqntipclgr
661  ecgtlgstmf  egycqkcfie  aqnqrfheak  rteeqlrssq  rrdvprttqs  tsrpkcaras
721  cknilacrse  elcmecqhpn  qrmgpgahrg  epapedppkq  rcrapacdhf  gnakcngycn
781  ecfqfkqmyg
```

By "TNFAIP3 polynucleotide" is meant a polynucleotide encoding an TNFAIP3 polypeptide. An exemplary TNFAIP3 polynucleotide is provided at NCBI Accession No. NM_006290.3. The sequence at NCBI Accession No. NM_006290.3 is provided below: SEQ ID NO: 14

```
  1  ctttggaaag  tcccgtggaa  atccccgggc  ctacaacccg  catacaactg  aaacggggca
 61  aagcagactg  cgcagtctgc  agtcttcgtg  gcgggccaag  cgagcttgga  gcccgcgggg
121  gcggagcggt  gagagcggcc  gccaagagag  atcacacccc  cagccgaccc  tgccagcgag
```

-continued

```
 181   cgagcccgac cccaggcgtc catggagcgt cgcctccgcc cggtccctgc cccgaccccc
 241   gcctgcggcg cgctcctgcc ttgaccagga cttgggactt tgcgaaagga tcgcggggcc
 301   cggagaggtg ttggagagca caatggctga acaagtcctt cctcaggctt tgtatttgag
 361   caatatgcgg aaagctgtga agatacggga gagaactcca gaagacattt ttaaacctac
 421   taatgggatc attcatcatt ttaaaaccat gcaccgatac acactggaaa tgttcagaac
 481   ttgccagttt tgtcctcagt ttcgggagat catccacaaa gccctcatcg acagaaacat
 541   ccaggccacc ctggaaagcc agaagaaact caactggtgt cgagaagtcc ggaagcttgt
 601   ggcgctgaaa acgaacggtg acggcaattg cctcatgcat gccacttctc agtacatgtg
 661   gggcgttcag gacacagact tggtactgag gaaggcgctg ttcagcacgc tcaaggaaac
 721   agacacacgc aactttaaat tccgctggca actggagtct ctcaaatctc aggaatttgt
 781   tgaaacgggg ctttgctatg atactcggaa ctggaatgat gaatgggaca atcttatcaa
 841   aatggcttcc acagacacac ccatggcccg aagtggactt cagtacaact cactggaaga
 901   aatacacata tttgtccttt gcaacatcct cagaaggcca atcattgtca tttcagacaa
 961   aatgctaaga agtttggaat caggttccaa tttcgcccct tgaaagtgg gtggaattta
1021   cttgcctctc cactggcctg cccaggaatg ctacagatac ccattgttc tcggctatga
1081   cagccatcat tttgtaccct tggtgaccct gaaggacagt gggcctgaaa tccgagctgt
1141   tccacttgtt aacagagacc ggggaagatt tgaagactta aaagttcact ttttgacaga
1201   tcctgaaaat gagatgaagg agaagctctt aaaagagtac ttaatggtga tagaaatccc
1261   cgtccaaggc tgggaccatg gcacaactca tctcatcaat gccgcaaagt tggatgaagc
1321   taacttacca aaagaaatca atctggtaga tgattacttt gaacttgttc agcatgagta
1381   caagaaatgg caggaaaaca gcgagcaggg gaggagagag gggcacgccc agaatcccat
1441   ggaaccttcc gtgccccagc tttctctcat ggatgtaaaa tgtgaaacgc ccaactgccc
1501   cttcttcatg tctgtgaaca cccagccttt atgccatgag tgctcagaga ggcggcaaaa
1561   gaatcaaaac aaactcccaa agctgaactc caagccgggc cctgaggggc tccctggcat
1621   ggcgctcggg gcctctcggg gagaagccta tgagcccttg gcgtggaacc ctgaggagtc
1681   cactgggggg cctcattcgg ccccaccgac agcacccagc ccttttctgt tcagtgagac
1741   cactgccatg aagtgcagga gccccggctg ccccttcaca ctgaatgtgc agcacaacgg
1801   attttgtgaa cgttgccaca acgcccggca acttcacgcc agccacgccc cagaccacac
1861   aaggcacttg gatcccggga gtgccaagc ctgcctccag gatgttacca ggacatttaa
1921   tgggatctgc agtacttgct tcaaaaggac tacagcagag gcctcctcca gcctcagcac
1981   cagcctccct ccttcctgtc accagcgttc caagtcagat ccctcgcggc tcgtccggag
2041   cccctccccg cattcttgcc acagagctgg aaacgacgcc cctgctggct gcctgtctca
2101   agctgcacg actcctgggg acaggacggg gacgagcaag tgcagaaaag ccggctgcgt
2161   gtattttggg actccagaaa acaagggctt tgcacactg tgtttcatcg agtacagaga
2221   aaacaaacat tttgctgctg cctcagggaa agtcagtccc acagcgtcca ggttccagaa
2281   caccattccg tgcctgggga gggaatgcgg cacccttgga agcaccatgt ttgaaggata
2341   ctgccagaag tgtttcattg aagctcagaa tcagagattt catgaggcca aaaggacaga
2401   agagcaactg agatcgagca gcgcagaga tgtgcctcga accacacaaa gcacctcaag
2461   gcccaagtgc gcccgggcct cctgcaagaa catcctggcc tgccgcagcg aggagctctg
2521   catggagtgt cagcatccca accagaggat gggccctggg gccaccggg gtgagcctgc
2581   ccccgaagac cccccaagc agcgttgccg ggccccccgcc tgtgatcatt ttggcaatgc
```

```
2641  caagtgcaac ggctactgca acgaatgctt tcagttcaag cagatgtatg gctaaccgga 2701  aacaggtggg tcacctcctg caagaagtgg ggcctcgagc tgtcagtcat catggtgcta 2761  tcctctgaac ccctcagctg ccactgcaac agtgggctta agggtgtctg agcaggagag 2821  gaaagataag ctcttcgtgg tgcccacgat gctcaggttt ggtaacccgg gagtgttccc 2881  aggtggcctt agaaagcaaa gcttgtaact ggcaagggat gatgtcagat tcagcccaag 2941  gttcctcctc tcctaccaag caggaggcca ggaacttctt tggacttgga aggtgtgcgg 3001  ggactggccg aggcccctgc accctgcgca tcaggactgc ttcatcgtct tggctgagaa 3061  agggaaaaga cacacaagtc gcgtgggttg gagaagccag agccattcca cctcccctcc 3121  cccagcatct ctcagagatg tgaagccaga tcctcatggc agcgaggccc tctgcaagaa 3181  gctcaaggaa gctcagggaa atggacgta ttcagagagt gtttgtagtt catggttttt 3241  ccctacctgc ccggttcctt tcctgaggac ccggcagaaa tgcagaacca tccatggact 3301  gtgattctga ggctgctgag actgaacatg ttcacattga cagaaaaaca agctgctctt 3361  tataatatgc accttttaaa aaattagaat attttactgg gaagacgtgt aactctttgg 3421  gttattactg tctttacttc taaagaagtt agcttgaact gaggagtaaa agtgtgtaca 3481  tatataatat acccttacat tatgtatgag ggattttttt aaattatatt gaaatgctgc 3541  cctagaagta caataggaag gctaaataat aataacctgt tttctggttg ttgttggggc 3601  atgagcttgt gtatacactg cttgcataaa ctcaaccagc tgcctttta aagggagctc 3661  tagtcctttt tgtgtaattc actttattta ttttattaca aacttcaaga ttatttaagt 3721  gaagatattt cttcagctct ggggaaaatg ccacagtgtt ctcctgagag aacatccttg 3781  ctttgagtca ggctgtgggc aagttcctga ccacagggag taaattggcc tctttgatac 3841  acttttgctt gcctccccag gaaagaagga attgcatcca aggtatacat acatattcat 3901  cgatgtttcg tgcttctcct tatgaaactc cagctatgta ataaaaaact atactctgtg 3961  ttctgttaat gcctctgagt gtcctacctc cttggagatg agatagggaa ggagcaggga 4021  tgagactggc aatggtcaca gggaaagatg tggccttttg tgatggtttt attttctgtt 4081  aacactgtgt cctgggggg ctgggaagtc ccctgcatcc catggtaccc tggtattggg 4141  acagcaaaag ccagtaacca tgagtatgag gaaatctctt tctgttgctg gcttacagtt 4201  tctctgtgtg ctttgtggtt gctgtcatat ttgctctaga agaaaaaaaa aaaggaggg 4261  gaaatgcatt tcccccagag ataaaggctg ccattttggg ggtctgtact tatggcctga 4321  aaatatttgt gatccataac tctacacagc ctttactcat actattaggc acactttccc 4381  cttagagccc cctaagtttt tcccagacga atctttataa tttctttcca agataccaa 4441  ataaacttca gtgttttcat ctaattctct taaagttgat atcttaatat tttgtgttga 4501  tcattatttc cattcttaat gtgaaaaaaa gtaattattt atacttatta taaaaagtat 4561  ttgaaatttg cacatttaat tgtccctaat agaaagccac ctattctttg ttggatttct 4621  tcaagttttt ctaaataaat gtaacttttc acaagagtca acattaaaaa ataaattatt 4681  taagaacaga aaaaaaaaaa aaaaa
```

By "TNFRSF12A polypeptide" is meant a polypeptide or fragment thereof having at least about 85% amino acid identity to NCBI Accession No. NP_057723.1 and having a biological activity of a TNFRSF12A (tumor necrosis factor receptor superfamily 12A) polypeptide. Biological activities of a TNFRSF12A polypeptide include TNFSF12/TWEAK receptor activity. The sequence at NCBI Accession No. NP_057723.1 is shown below: SEQ ID NO: 15

```
  1  margslrrll rllvlglwla llrsvageqa pgtapcsrgs swsadldkcm dcascrarph
 61  sdfclgcaaa ppapfrllwp ilggalsltf vlgllsgflv wrrcrrrekf ttpieetgge
121  gcpavaliq
```

By "TNFRSF12A polynucleotide" is meant a polynucleotide encoding an 50 TNFRSF12A polypeptide. An exemplary TNFRSF12A polynucleotide is provided at NCBI Accession No. NM_016639.2. The sequence at NCBI Accession No. NM_016639.2 is provided below: SEQ ID NO: 16

```
   1  aaggcggggg cggggcggg gcggcggccg tgggtccctg ccggccggcg gcgggcgcag
  61  acagcggcgg gcgcaggacg tgcactatgg ctcggggctc gctgcgccgg ttgctgcggc
 121  tcctcgtgct ggggctctgg ctggcgttgc tgcgctccgt ggccggggag caagcgccag
 181  gcaccgcccc ctgctcccgc ggcagctcct ggagcgcgga cctggacaag tgcatggact
 241  gcgcgtcttg cagggcgcga ccgcacagcg acttctgcct gggctgcgct gcagcacctc
 301  ctgcccoctt ccggctgctt tggcccatcc ttgggggcgc tctgagcctg accttcgtgc
 361  tggggctgct ttctggcttt ttggtctgga cgatgccg caggagagag aagttcacca
 421  cccccataga ggagaccggc ggagagggct gcccagctgt ggcgctgatc cagtgacaat
 481  gtgcccctg ccagccgggg ctcgcccact catcattcat tcatccattc tagagccagt
 541  ctctgcctcc cagacgcggc gggagccaag ctcctccaac cacaagggg gtggggggcg
 601  gtgaatcacc tctgaggcct gggcccaggg ttcagggaa ccttccaagg tgtctggttg
 661  ccctgcctct ggctccagaa cagaaaggga gcctcacgct ggctcacaca aaacagctga
 721  cactgactaa ggaactgcag catttgcaca ggggaggggg gtgccctcct tcctagaggc
 781  cctgggggcc aggctgactt gggggggcaga cttgacacta ggccccactc actcagatgt
 841  cctgaaattc caccacgggg gtcaccctgg ggggttaggg acctattttt aacactaggg
 901  ggctggccca ctaggagggc tggccctaag atacagaccc ccccaactcc ccaaagcggg
 961  gaggagatat ttattttggg gagagtttgg aggggaggga gaatttatta ataaaagaat
1021  ctttaacttt aaaaaaaaaa aaaaaaaa
```

By "TMC4 polypeptide" is meant a polypeptide or fragment thereof having at least about 85% amino acid identity to NCBI Accession No. NP_653287.2 (isoform 2) or NP_001138775.2 (isoform 1) and having a biological activity of a TMC4 (transmembrane channel-like protein 4 isoform 2) polypeptide. Biological activities of a TMC4 polypeptide include ion transport activity. The sequence at NCBI Accession No. NP_653287.2 is shown below: SEQ ID NO: 17

```
  1  meenptlese awgssrewla prearggpsl ssvlnelpsa atlryrdpgv lpwgaleeee
 61  edggrsrkaf tevtqtelqd phpsrelpwp mqarrahrqr nasrdqvvyg sgtktdrwar
```

```
121  llrrskektk eglrslqpwa wtlkriggqf gagtesyfsl lrflllllnvl asvlmacmtl
181  lptwlggapp gppgpdissp cgsynphsqg lvtfatqlfn llsgegylew splfygfypp
241  rprlavtylc wafavglicl llilhrsvsg lkqtllaese altsyshrvf sawdfglcgd
301  vhvrlrqrii lyelkvelee tvvrrqaavr tlgqqarvwl vrvllnllvv allgaafygv
361  ywatgctvel qemplvqelp llklgvnylp sifiagvnfv lppvfkliap legytrsrqi
421  vfillrtvfl rlaslvvllf slwnqitcgg dseaedcktc gynykqlpcw etvlgqemyk
481  lllfdlltvl avalliqfpr kllcglcpga lgrlagtqef qvpdevlgli yaqtvvwvgs
541  ffcpllplln tvkflllfyl kkltlfstcs paartfrasa anfffplvll lglaissvpl
601  lysiflipps klcgpfrgqs siwaqipesi sslpettqnf lfflgtqafa vplllissil
661  maytvalans ygrliselkr qreteaqnkv flarravalt stkpal
```

By "TMC4 polynucleotide" is meant a polynucleotide encoding a TMC4 polypeptide. An exemplary TMC4 polynucleotide sequence is provided at NCBI Accession No. NM_144686.3. The exemplary sequence provided at NCBI Accession No. NM_144686.3 is reproduced below: SEQ ID NO: 18

```
   1  ctgagaaacc acaggaagtg taccttactc cctccgggcc acctgctggc caggtacaca
  61  cctgcccctg gcccctccct tacctggggc agtgtctgcc tggtggccac tagagacagc
 121  ccagcctggg gccatggaag aaaacccgac cttggaatca gaagcctggg gctcctctag
 181  ggagtggctg gccccccggg aggccagagg aggcccatcg ctgtcttctg tgctgaacga
 241  gctgcccagt gctgccaccc ttcggtaccg agaccctggg gtgctgcctt gggggcgct
 301  ggaggaggag gaggaggatg gaggaaggag cagaaaggcc ttcacagaag tcacccagac
 361  agagctgcag gaccctcacc cttcccggga actgccctgg cccatgcagg ccagacgggc
 421  acacaggcaa agaaatgcca gcagggacca ggtggtctat ggctctggaa ctaagacgga
 481  ccgatgggcg cggctacttc ggaggtccaa ggagaaaaca aaggaaggct gcgaagcct
 541  gcagccctgg gcgtggacac tgaagaggat cgggggccag tttggcgccg gcacggagtc
 601  ctacttctcc ctgctgcgct tcctgctcct tcttaacgtg ctggcctctg tgctcatggc
 661  ctgcatgacg ctgctgccca cctggttggg aggcgctccc ccaggccctc ccggccccga
 721  catctcctcg ccctgcggct cctataaccc ccactcccag ggcctggtca cctttgccac
 781  ccagctcttc aacttgctct cgggtgaggg ttacctggaa tggtcccctc tcttctatgg
 841  cttctacccg ccccgcccac gcctggcggt cacctacctg tgctgggcct ttgccgttgg
 901  cctcatctgc ctcctgctca tcctgcatcg ctcggtgtct gggctgaagc agacactgct
 961  ggcggagtcc gaggctctga ccagctacag ccaccgggtg ttctcggcct gggacttcgg
1021  tctctgcggg gacgtccacg tgcggctgcg ccagcgcatc atcttgtacg aattaaaggt
1081  ggagctggag gagacagtgg tgcggcgcca ggctgcggtg cggacgctgg gccagcaagc
1141  cagggtttgg ttggtgcggg tgctgctcaa cctgctggtg gtcgcgctcc tgggggcagc
1201  cttctatggc gtctactggg ctacggggtg caccgtggag ctgcaggaga tgcccttgt
1261  ccaggagttg ccactgctga agcttggggt gaattacctt ccgtccatct tcatcgctgg
1321  ggtcaatttt gtgctgccgc ccgtgttcaa gctcattgct ccactggagg ctacactcg
1381  gagtcgccag atcgttttta tcctgctcag gaccgtgttt cttcgcctcg cctccctggt
1441  ggtcctgctc ttctctctct ggaatcagat cacttgtggg ggcgactccg aggctgagga
1501  ctgcaaaacc tgtggctaca attacaaaca acttccgtgc tgggagactg tcctgggcca
1561  ggaaatgtac aaacttctgc tctttgatct gctgactgtc ttggcagtcg cgctgctcat
```

```
-continued
1621   ccagtttcct agaaagctcc tctgtggcct ctgtcctggg gcgctgggtc gtctggcggg 1681   gacccaagag ttccaggtgc ccgacgaggt gctggggctc atctacgcgc agacggtggt 1741   ctgggtgggg agttttttct gcccttact  gccctgctt  aacacggtca agttcctgct 1801   gcttttctac ctgaagaagc ttaccctctt ctccacctgc tcccggctg  cccgcacctt 1861   ccgggcctcc gcggcgaatt tctttttccc cttggtcctt ctcctgggtc tggccatctc 1921   cagcgttccc ctgctttaca gcatcttcct gatcccgcct tctaagctgt gtggtccatt 1981   ccggggcag  tcgtccatct gggcccagat ccctgagtct atttccagcc tccctgagac 2041   cacccagaat ttcctcttct tcctggggac ccaggctttt gctgtgcccc ttctgctgat 2101   ctccagcatc ctgatggcgt acactgtggc tctggctaac tcctacggac gcctcatctc 2161   tgagctcaaa cgtcagagag agacggaggc gcagaataaa gtcttcctgg cacggcgcgc 2221   tgtggcgctg acctccacca aaccggctct ttgaccccg  cagcccacgt cccgctttca 2281   gaccccaggc ccattgtaag cctaggtcac aacatctgta aactaggaga actggagaag 2341   actccacgcc cttccagctt tggtatctgg agatttccag ggcccctcgc cgccacgtcc 2401   ctgactctcg ggtgatcttc cttgtatcaa taaatacagc cgaggttgct gagcgcgctt 2461   tgaaaaaaaa aaaaaaa
```

A "therapeutic" treatment is a treatment administered to a subject who exhibits a sign or symptom of pathology, for the purpose of diminishing or eliminating that sign or symptom.

As used herein, "treating a disease or disorder" means reducing the frequency with which a sign or symptom of the disease or disorder is experienced by a patient.

The phrase "therapeutically effective amount," as used herein, refers to an amount that is sufficient or effective to prevent or treat (delay or prevent the onset of, prevent the progression of, inhibit, decrease or reverse) a disease or disorder associated with ASD, including alleviating signs and symptoms of such diseases or disorders.

By "variant" as is meant a polynucleotide or polypeptide sequence that differs from a wild-type or reference sequence by one or more nucleotides or one or more amino acids.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the identification of blood-based biomarkers that are associated with an ASD-associated inflammatory disorder. The invention is based at least in part on the comparison of gene expression profiles (differentially expressed transcripts) in inflamed ileocolonic tissues from GI symptomatic ASD children and in peripheral blood of ASD children. In an earlier study, the molecular profile in gastrointestinal mucosal biopsies from $ASD^{IC+}$ children was found to yield unique differentially expressed transcripts, not present in pediatric Crohn's disease (CD) or ulcerative colitis (UC). In studies described herein, the mucosal expression profile is compared to the peripheral blood expression profile in a second cohort of cases and controls. In two separate case/control mucosal-based cohorts, an overlap of 59 differentially expressed transcripts that are unique to inflamed ileocolonic tissues from GI symptomatic ASD children was found. Nine of these 59 transcripts are also differentially expressed in the peripheral blood of ASD children. These nine transcripts therefore represent a blood-based biomarker for ASD-associated ileocolonic inflammation.

In one embodiment, the biomarkers of the invention are useful for discriminating between different inflammatory disorders.

Such biomarkers could be used for ASD-associated inflammatory disorder screening and diagnosis, as well as potentially for designing novel pharmaceuticals that would target the genes responsible for the DETs, and in assessing response to new therapies. Given the probability of multiple underlying pathogenic mechanisms of some ASD-associated inflammatory disorders, the present invention provides novel biomarkers present in a blood sample of a subject. The biomarkers of the invention allow a more accurate diagnosis, prognosis, or treatment strategy of an ASD-associated inflammatory disorder.

In one embodiment, the present invention includes a method of screening for an Autism Spectrum Disorder in a patient by analyzing differential gene expression patterns comprising the steps of: obtaining a nucleic acid sample from cells of a patient; performing a nucleic acid analysis on the nucleic acid samples to obtain a gene expression analysis data set; and comparing said data set to a control data set corresponding to a gene ensemble of differentially expressed genes indicative of autism spectrum disorder, wherein autism spectrum disorder is indicated upon observing statistically significant differential gene expression. In one embodiment, the nucleic acid sample is obtained from a blood sample of a patient.

In some embodiments of the invention, one can observe an expression profile of at least, 2, 3, 4, 5, 6, 7, 8, 9 or 10 or more genes whose expression is shown to be dysregulated in autism spectrum disorders (e.g. using microarray technologies). In certain embodiments of the invention, the method is performed on a plurality of individuals and the results are then categorized based upon similarities or differences in their gene expression profiles. Optionally, the expression profile(s) is observed and/or collected and/or stored using a computer system comprising a processor element and a memory storage element adapted to process and store data from one or more expression profiles (e.g. in a library of such profiles). In this context, certain embodiments of the invention comprise an electronically searchable library of profiles, wherein the profiles include an individual's gene expression data in combination with other diagnostic data, for example assessments of behavior associated with autism spectrum disorders.

In one embodiment, the invention relates to one or more biomarkers of ASD. The invention is partly based upon the discovery of differentially expressed transcripts (DETs) detected in samples obtained from subjects with $ASD^{IC}$, compared to samples obtained from either non-disease control subjects, subjects with Crohn's disease, or subjects with ulcerative colitis. Given the broad heterogeneity that is the hallmark of ASD, coupled with the understanding that earlier diagnosis and treatment provides the greatest chance for the most positive outcomes, a blood-based test to diagnose autism (and/or ASD subtypes) early on would have tremendous clinical value. A key confound in these efforts, heterogeneity (in the form of ASD subtypes) exists within the core domains (language, social interaction, and range of interests), but also within associated medical comorbidity domains (e.g. epilepsy, sleep disorders, gastrointestinal disorders, etc.). Without being bound by theory, it is believed the most promising validated blood-based biomarkers would be derived within ASD subtypes. It is an ASD subtype within the comorbidity domains, i.e. gastrointestinal disorders, that is the focus of the studies described herein.

In one embodiment, the present invention includes a method of treating a pre-selected patient, comprising the step of administering a treatment for a gastrointestinal disorder. The patient is pre-selected by detecting an alteration in the level of a polynucleotide or polypeptide of at least one biomarker of the invention.

In one embodiment, the biomarker of the invention is FCER1A, CYP2S1, TMC4, TNFRSF12A, IL1RN, TNFAIP3, CENPE, MTHFD2, or SIGLEC17P. In one embodiment, the biomarker of the invention is detected to have decreased expression in a subject with ASD compared to a control sample. In another embodiment, the biomarker of the invention is detected to have increased expression in a subject with ASD compared to a control sample.

Methods of Treatment

The methods of the invention include methods of treating gastrointestinal disorders or ASD-associated inflammatory disorders in pre-selected patients. In one embodiment, a patient is pre-selected by detecting an alteration in the level of a polynucleotide or polypeptide of any one or more of biomarkers FCER1A, CYP2S1, TMC4, TNFRSF12A, IL1RN, TNFAIP3, CENPE, MTHFD2, or SIGLEC17P relative to a reference. In a particular embodiment, a patient is pre-selected by detecting an increase in the level of TMC4 polypeptide or polynucleotide, an increase in the level of TNFAIP3 polypeptide or polynucleotide, a decrease in the level of FCER1A polypeptide or polynucleotide, a decrease in the level of CYP2S1 polypeptide or polynucleotide, a decrease in the level of TNFRSF12A polypeptide or polynucleotide, a decrease in the level of IL1RN polypeptide or polynucleotide, a decrease in the level of CENPE polypeptide or polynucleotide, a decrease in the level of MTHFD2 polypeptide or polynucleotide, or a decrease in the level of SIGLEC17P polypeptide or polynucleotide, relative to a reference. Methods of detecting levels of polynucleotides or polypeptides of the biomarkers of the invention are described elsewhere herein.

The methods include the step of administering a treatment for gastrointestinal disorders or ASD-associated inflammatory disorders to a pre-selected subject. Treatments for such gastrointestinal disorders or ASD-associated inflammatory disorders include, without limitation, treatment with therapeutic agents such as corticosteroids, immunomodulators, 5-aminosalicylic acid preparations, cytokine specific antagonists, antimicrobials, probiotics, and supplemental digestive enzymes. Exemplary corticosteroids include, without limitation, budesonide, dexamethasone, hydrocortisone, methylprednisolone, prednisolone, and prednisone. Examples of immunomodulators include, without limitation, azathioprine, mercaptopurine, and methotrexate. Treatment for gastrointestinal disorders or ASD-associated inflammatory disorders also includes dietary restrictions. Additionally, treatment for such gastrointestinal disorders or ASD-associated inflammatory disorders may include targeted therapies that decrease or eliminate the expression of any of the polynucleotides or polypeptides of the genes responsible for the unique biomarker profiles described herein.

In one embodiment, a therapeutically effective amount of a composition comprising the therapeutic agent is administered to the subject that is sufficient to treat the gastrointestinal disorder or ASD-associated inflammatory disorder, or symptom thereof, under conditions such that the disorder is treated. The composition may be administered systemically, for example, formulated in a pharmaceutically-acceptable buffer such as physiological saline. The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy. In particular embodiments, the treatment is administered orally, intravenously, topically, by enema, or by suppository.

The amount of the therapeutic agent to be administered varies depending upon the manner of administration, the age and body weight of the patient, and with the clinical symptoms of the gastrointestinal disorder or ASD-associated inflammatory disorder. Generally, amounts will be in the range of those used for other agents used in the treatment of gastrointestinal disorders or ASD-associated inflammatory disorders, although in certain instances lower amounts will be needed because of the increased specificity of the agent. A composition is administered at a dosage that decreases effects or symptoms of a gastrointestinal disorder or ASD-associated inflammatory disorder as determined by a method known to one skilled in the art.

Diagnostic Methods

The methods of the invention also include the use of a biomarker to detect a gastrointestinal disorder and/or autism spectrum disorder in a subject (e.g., a human subject). As described herein, altered gene expression of transcripts indicated the presence of a gastrointestinal disorder in ASD individuals. The molecular evidence indicated an overlapping, yet unique, IBD-like condition in ASD children.

Biological samples include tissue samples (e.g., cell samples, biopsy samples), such as tissue from colon or ileum. Biological samples also include bodily fluids, including, but not limited to, blood, blood serum, plasma, saliva, and urine. Altered levels of a biomarker alone or in combination with one or more additional markers relative to a reference are considered a positive indicator of a gastrointestinal and/or autism spectrum disorder. In one embodiment, the biological sample is blood.

Any suitable method can be used to detect one or more of the markers described herein. Successful practice of the invention can be achieved with one or a combination of methods that can detect and, preferably, quantify the markers. These methods include, without limitation, hybridization-based methods, including those employed in biochip arrays, mass spectrometry (e.g., laser desorption/ionization mass spectrometry), fluorescence (e.g. sandwich immunoassay), surface plasmon resonance, ellipsometry and atomic force microscopy. Expression levels of markers (e.g., polynucleotides or polypeptides) are compared by procedures well known in the art, such as RT-PCR, Northern blotting, Western blotting, flow cytometry, immunocytochemistry, binding to magnetic and/or antibody-coated beads, in situ hybridization, fluorescence in situ hybridization (FISH), flow chamber adhesion assay, ELISA, microarray analysis, or colorimetric assays. Methods may further include, one or more of electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)", atmospheric pressure photoionization mass spectrometry (APPI-MS), APPI-MS/MS, and APPI-(MS)n, quadrupole mass spectrometry, fourier transform mass spectrometry (FTMS), and ion trap mass spectrometry, where n is an integer greater than zero. Detection methods may include use of a biochip array. Biochip arrays useful in the invention include protein and polynucleotide arrays. One or more markers are captured on the biochip array and subjected to analysis to detect the level of the markers in a sample.

Markers may be captured with capture reagents immobilized to a solid support, such as a biochip, a multiwell microtiter plate, a resin, or a nitrocellulose membrane that is subsequently probed for the presence or level of a marker. Capture can be on a chromatographic surface or a biospecific surface. For example, a sample containing the markers, such as serum, may be used to contact the active surface of a biochip for a sufficient time to allow binding. Unbound molecules are washed from the surface using a suitable eluant, such as phosphate buffered saline. In general, the more stringent the eluant, the more tightly the proteins must be bound to be retained after the wash.

Upon capture on a biochip, analytes can be detected by a variety of detection methods selected from, for example, a gas phase ion spectrometry method, an optical method, an electrochemical method, atomic force microscopy and a radio frequency method. In one embodiment, mass spectrometry, and in particular, SELDI, is used. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and nonimaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Mass spectrometry (MS) is a well-known tool for analyzing chemical compounds. Thus, in one embodiment, the methods of the present invention comprise performing quantitative MS to measure the serum peptide marker. The method may be performed in an automated (Villanueva, et al., Nature Protocols (2006) 1(2):880-891) or semi-automated format. This can be accomplished, for example with MS operably linked to a liquid chromatography device (LC-MS/MS or LC-MS) or gas chromatography device (GC-MS or GC-MS/MS). Methods for performing MS are known in the field and have been disclosed, for example, in US Patent Application Publication Nos: 20050023454; 20050035286; U.S. Pat. No. 5,800,979 and references disclosed therein.

In an additional embodiment of the methods of the present invention, multiple markers are measured. The use of multiple markers increases the predictive value of the test and provides greater utility in diagnosis, patient stratification and patient monitoring. The process called "Pattern recognition" detects the patterns formed by multiple markers greatly improves the sensitivity and specificity of clinical markers for predictive medicine. Subtle variations in data from clinical samples indicate that certain patterns of protein expression can predict phenotypes such as the presence or absence of a certain disease, a particular stage of disease-progression, or a positive or adverse response to drug treatments. In the present invention, additional markers may include cytokine profiles and/or serum antibodies directed against gut microbes.

Expression levels of particular nucleic acids or polypeptides are correlated with a gastrointestinal disorder and/or autistic spectrum disorder and thus are useful in diagnosis. Methods for measuring levels of polypeptide include immunoassay, ELISA, western blotting and radioimmunoassay. Oligonucleotides or longer fragments derived from a nucleic acid sequence described herein, antibodies that bind a polypeptide described herein, or any other method known in the art may be used to monitor expression of a polynucleotide or polypeptide of interest. In other embodiments, a 1.5, 2, 3, 4, 5, or 6-fold change in the level of a marker of the invention is indicative of a gastrointestinal and/or autistic spectrum disorder. In yet another embodiment, an expression profile that characterizes alterations in the expression two or more markers is correlated with a particular disease state (e.g., gastrointestinal and/or autistic spectrum disorder).

The diagnostic methods described herein can be used individually or in combination with any other diagnostic method described herein for a more accurate diagnosis of the presence of a gastrointestinal and/or autistic spectrum disorder. The diagnostic methods described herein can also be used to reliably distinguish ileoclitis in an individual having autism spectrum disorder from Crohn's disease or inflammatory bowel disease.

As indicated above, the invention provides methods for aiding diagnosis of a gastrointestinal and/or autism spectrum disorder using one or more markers, as specified herein. These markers can be used alone, in combination with other markers in any set, or with entirely different markers in aiding diagnosis. The measurement of markers may also involve quantifying the markers to correlate the detection of markers with a diagnosis of a gastrointestinal and/or autism spectrum disorder. Thus, if the amount of the markers detected in a subject being tested is different compared to a control amount (i.e., higher than the control), then the subject being tested has a higher probability of having a gastrointestinal and/or autism spectrum disorder. The correlation may take into account the amount of the marker or markers in the sample compared to a control amount of the marker or markers (e.g., in normal subjects). A control can be, e.g., the average or median amount of marker present in comparable samples of normal subjects in normal subjects or in subjects such as where the disease or disorder is undetectable. The control amount is measured under the same or substantially similar experimental conditions as in measuring the test amount. As a result, the control can be employed as a reference standard, where the normal (non-disease) phenotype is known, and each result can be compared to that standard, rather than re-running a control.

Accordingly, a marker profile may be obtained from a subject sample and compared to a reference marker profile obtained from a reference population, so that it is possible to classify the subject as belonging to or not belonging to the reference population. The correlation may take into account the presence or absence of the markers in a test sample and the frequency of detection of the same markers in a control. The correlation may take into account both of such factors to facilitate diagnosis of a gastrointestinal and/or autism spectrum disorder.

In certain embodiments of the methods of qualifying a disorder, the methods further comprise managing subject treatment based on the status. The invention also provides for such methods where the markers (or specific combination of markers) are measured again after subject management. In these cases, the methods are used to monitor the status of the disorder or progression of the disorder.

Any marker, individually, is useful in aiding in the diagnosis of a gastrointestinal and/or autistic spectrum disorder. First, the selected marker is detected in a subject sample using the methods described herein. Then, the result is compared with a control that distinguishes disorder status from non-disorder status. As is well understood in the art, the techniques can be adjusted to increase sensitivity or specificity of the diagnostic assay depending on the preference of the diagnostician.

The diagnosis of a gastrointestinal and/or autistic spectrum disorder can be used to inform treatment selection. Treatments for such ASD or ASD inflammatory disorders include without limitation treatment with corticosteroids, immunomodulators, 5-aminosalicylic acid preparations, cytokine specific antagonists, dietary restrictions, antimicrobials, probiotics, and supplemental digestive enzymes. Additionally, treatment for such ASD or ASD inflammatory disorders may include targeted therapies that decrease or eliminate the expression of any of the nucleic acid molecules or polypeptides of the genes responsible for the unique transcriptomes described herein.

While individual markers are useful diagnostic markers, in some instances, a combination of markers provides greater predictive value than single markers alone. The detection of a plurality of markers (or absence thereof, as the case may be) in a sample can increase the percentage of true positive and true negative diagnoses and decrease the percentage of false positive or false negative diagnoses. Thus, preferred methods of the present invention comprise the measurement of more than one marker.

Microarrays

As reported herein, a number of biomarkers have been identified that are associated with a gastrointestinal and/or autistic spectrum disorder. In particular, the invention provides diagnostic methods and compositions useful for identifying an expression profile that identifies a subject as having a gastrointestinal and/or autistic spectrum disorder. Such assays can be used to measure an alteration in the level of a gene transcript or polypeptide encoded by the transcript.

The polypeptides and polynucleotides of the invention are useful as hybridizable array elements in a microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14: 1675-1680, 1996), and Schena, et al. (Proc. Natl. Acad. Sci. 93: 10614-10619, 1996), herein incorporated by reference. Methods for making polypeptide microarrays are described, for example, by Ge (Nucleic Acids Res. 28: e3.i-e3. vii, 2000), MacBeath et al., (Science 289: 1760-1763, 2000), Zhu et al. (Nature Genet. 26:283-289), and in U.S. Pat. No. 6,436,665, hereby incorporated by reference.

Nucleic Acid Microarrays

To produce a nucleic acid microarray, oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

A nucleic acid molecule (e.g. RNA or DNA) derived from a biological sample may be used to produce a hybridization probe as described herein. The biological samples are generally derived from a patient, preferably as a bodily fluid (such as blood, blood serum, plasma, saliva, urine, seminal fluids, and ejaculate) or tissue sample (e.g. a tissue sample obtained by biopsy). For some applications, cultured cells or other tissue preparations may be used. The mRNA is isolated according to standard methods, and cDNA is produced and used as a template to make complementary RNA suitable for hybridization. Such methods are known in the art. The RNA is amplified in the presence of fluorescent nucleotides, and the labeled probes are then incubated with the microarray to allow the probe sequence to hybridize to complementary oligonucleotides bound to the microarray.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37 C, and most preferably of at least about 42° C.

Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/µl denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

A detection system may be used to measure the absence, presence, and amount of hybridization for all of the distinct nucleic acid sequences simultaneously (e.g., Heller et al., Proc. Natl. Acad. Sci. 94:2150-2155, 1997). Preferably, a scanner is used to determine the levels and patterns of fluorescence.

Polymerase Chain Reaction (PCR)

Polymerase chain reaction (PCR) is widely known in the art. For example, U.S. Pat. Nos. 4,683,195, 4,683,202, and 4,800,159; K. Mullis, Cold Spring Harbor Symp. Quant. Biol., 51:263-273 (1986); and C. R. Newton & A. Graham, Introduction to Biotechniques: PCR, 2nd Ed., Springer-Verlag (New York: 1997), the disclosures of which are incorporated herein by reference, describe processes to amplify a nucleic acid sample target using PCR amplification extension primers which hybridize with the sample target. As the PCR amplification primers are extended, using a DNA polymerase (preferably thermostable), more sample target is made so that more primers can be used to repeat the process, thus amplifying the sample target sequence. Typically, the reaction conditions are cycled between those conducive to hybridization and nucleic acid polymerization, and those that result in the denaturation of duplex molecules.

In the first step of the reaction, the nucleic acid molecules of the sample are transiently heated, and then cooled, in order to denature double stranded molecules. Forward and reverse primers are present in the amplification reaction mixture at an excess concentration relative to the sample target. When the sample is incubated under conditions conducive to hybridization and polymerization, the primers hybridize to the complementary strand of the nucleic acid molecule at a position 3' to the sequence of the region desired to be amplified that is the complement of the sequence whose amplification is desired. Upon hybridization, the 3' ends of the primers are extended by the polymerase. The extension of the primer results in the synthesis of a DNA molecule having the exact sequence of the complement of the desired nucleic acid sample target. The PCR reaction is capable of exponentially amplifying the desired nucleic acid sequences, with a near doubling of the number of molecules having the desired sequence in each cycle. Thus, by permitting cycles of hybridization, polymerization, and denaturation, an exponential increase in the concentration of the desired nucleic acid molecule can be achieved.

The methods of the present invention involve amplifying regions of a polynucleotide with high fidelity using a thermostable DNA polymerase having 3'→5' exonuclease activity. As defined herein, "3'→5' exonuclease activity" refers to the activity of a template-specific nucleic acid polymerase having a 3'→5' exonuclease activity associated with some DNA polymerases, in which one or more nucleotides are removed from the 3' end of an oligonucleotide in a sequential manner. Polymerase enzymes having high fidelity 3'→5' exonuclease activity are useful, for example, when primer extension must be performed with high specificity. Polymerase enzymes having 3'→5' exonuclease proofreading activity are known to those in the art. Examples of suitable proofreading enzymes include TaKaRa LA Taq (Takara Shuzo Co., Ltd.) and Pfu (Stratagene), Vent, Deep Vent (New England Biolabs). Exemplary methods for performing long range PCR are disclosed, for example, in U.S. Pat. No. 5,436,149; Barnes, Proc. Natl. Acad. Sci. USA 91:2216-2220 (1994); Tellier et al., Methods in Molecular Biology, Vol. 226, PCR Protocols, 2nd Edition, pp. 173-177; and, Cheng et al., Proc. Natl. Acad. Sci. 91:5695-5699 (1994); the contents of which are incorporated herein by reference. In various embodiments, long range PCR involves one DNA polymerase. In some embodiments, long range PCR may involve more than one DNA polymerase. When using a combination of polymerases in long range PCR, it is preferable to include one polymerase having 3'→5' exonuclease activity, which assures high fidelity generation of the PCR product from the DNA template. Typically, a non-proofreading polymerase, which is the main polymerase is also used in conjunction with the proofreading polymerase in long range PCR reactions. Long range PCR can also be performed using commercially available kits, such as LA PCR kit available from Takara Bio Inc.

Hybridization

There are a variety of ways by which one can assess genetic profiles, and many of these rely on nucleic acid hybridization. Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary, but are mismatched at one or more positions.

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Kits

The present compositions may be assembled into kits or pharmaceutical systems for use in detecting or diagnosing a gastrointestinal disorder and/or autism spectrum disorder. Materials and reagents required for measuring the level of a polynucleotide or polypeptide in a sample may be assembled together in a kit. This generally will comprise a capture reagent, primer, or probe designed to hybridize specifically to target polynucleotides of interest. The primer or probe may be labeled with a radioisotope, a fluorophore, a chromophore, a dye, an enzyme, or TOF carrier. Also included may be enzymes suitable for amplifying nucleic acids, including various polymerases (reverse transcriptase, Taq, etc.), dNTPs/rNTPs and buffers (e.g., 10× buffer=100 mM Tris-HCl (pH 8.3), and 500 mM KCl) to provide the necessary reaction mixture for amplification. One or more of the deoxynucleotides may be labeled with a radioisotope, a fluorophore, a chromophore, a dye, or an enzyme. Such kits may also include enzymes and other reagents suitable for detection of specific nucleic acids or amplification products. The kits of the invention may also comprise associated instructions for using the agents of the invention. Additionally, one or more agents for treating a gastrointestinal disorder or autism spectrum disorder may be included.

Kits according to this aspect of the invention comprise a carrier means, such as a box, carton, tube or the like, having in close confinement therein one or more container means, such as vials, tubes, ampoules, bottles and the like. The container means of the kits will generally include at least one vial, test tube, flask, bottle, or other container means, into which a component may be placed, and preferably, suitably aliquoted. Where there is more than one component in the kit, the kit also will generally contain additional containers into which the additional components may be separately placed. However, various combinations of components may be comprised in a container. The kits of the present invention also will typically include a means for packaging the component containers in close confinement for commercial sale. Such packaging may include injection or blow-molded plastic containers into which the desired component containers are retained.

In General

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Identification of a Blood-Based Biomarker in Patients with Autism Spectrum Disorder Associated Ileocolitis Gastrointestinal (GI) symptoms are common in children with autism spectrum disorder (ASD) with a significant proportion of GI symptomatic ASD children having histologic ileocolitis (inflammation of the terminal ileum and/or colon). Previously, the molecular characterization of GI biopsy tissue from ASD children with ileocolitis ($ASD^{IC+}$) compared to anatomically similar inflamed mucosal GI tissue from typically developing (TD) children with inflammatory bowel disease (IBD; i.e. Crohn's disease or ulcerative colitis) and TD GI symptomatic children without evidence of GI mucosal inflammation ($TD^{IC-}$) was reported. In that study, it was found that inflamed ileocolonic tissue in ASD children possess a gene expression profile that, while overlapping with known IBD, has distinct features.

In this study, experiments performed were designed to: (1) confirm the earlier differential gene expression results from inflamed gastrointestinal biopsy tissue in autism spectrum disorder children compared to non-inflamed tissue from typically developing children and, (2) examine the overlap between gene expression in gastrointestinal biopsy tissue and whole blood samples derived from the same patients, in order to identify a putative blood-based test that is diagnostic for ileocolonic inflammation in ASD children.

The study presented herein provides confirmation of the findings of the previous study by replicating this molecular characterization in a second cohort of cases ($ASD^{IC}$) and controls ($TD^{IC-}$). In these two separate case/control mucosal-based cohorts, an overlap of 59 differentially expressed transcripts that are unique to inflamed ileocolonic tissue from GI symptomatic ASD children is demonstrated. Additionally, the study presented herein demonstrates that nine of these 59 transcripts are also differentially expressed in the peripheral blood of $ASD^{IC+}$ children. These nine transcripts therefore represent a blood-base biomarker for ASD-associated ileocolonic inflammation.

The materials and methods used in these experiments are now described.

Participants

Permission to perform this study was obtained from the Wake Forest University Health Sciences Institutional Review Board (IRB approvals: #IRB00007834 (control samples) and #BG03-464 (ASD samples)). Forty-eight sample sets from this IRB-approved study tissue bank were selected based on presence/absence of inflammation in the relevant tissue sample. For each subject, either 1 or 2 biopsies, and a single sample consisting of 2.5 ml whole blood (collected into a PaxGene Blood RNA tube (PreAnalytiX)), were processed.

Study Design

Case ($ASD^{IC+}$; N=21) & Control ($TD^{IC-}$; N=24)
1. ASDTI
  TI-inflamed (9)
  ASDTI blood (12 {same individuals})
2. ASDcolon
  colon-inflamed (9)
  ASDcolon blood (12 {same individuals})
3. ASDTI & ASDcolon
  TI & colon-inflamed (3)
  blood (3 {same individuals})
4. TDTI
  TDTI—not inflamed—'control' (12)
  TDTI blood (12 {same individuals})
5. TDcolon
  TDcolon—not inflamed—'control' (12)
  TD colon blood (12 {same individuals})

Microarray Assay

Total RNA was isolated from each biopsy tissue sample as described earlier (Walker et al, 2013, PLoS One 8:e58058). Briefly, total RNA was isolated from mucosal biopsies that had been stored in RNAlater by sonicating the tissue in the presence of TriReagent® reagent (Molecular Research Center, Inc., Cincinnati, Ohio) according to the method of Chomcynski and Sacchi (Chomcynski et al., 1987, Anal Biochem 162(1):156-159). Total RNA was purified using RNeasy® Minelute Plus columns (includes an on-column DNAse step) and reagents (Qiagen, Valencia, Calif.) and eluted in nuclease-free water. RNA concentration and quality were determined using a Nanodrop™ ND-1000 spectrophotometer (Nanodrop Technologies, Wilmington, Del.) and Agilent Bioanalyzer, respectively. A single biopsy specimen was typically 3-5 mg of tissue and yielded from 3-10 μg of high quality (e.g. RIN≥7) total RNA.

For the PaxGene blood tubes, total RNA was isolated in a QIAcube robotic workstation using RNeasy® Plus kits (Qiagen, Valencia, Calif.) following the manufacturer's protocols. RNA quantity and relative quality was assessed using a Nanodrop™ ND-1000 spectrophotometer. RNA integrity was determined using a bioanalyzer (Agilent Technologies, Palo Alto, Calif.). Total RNA for each sample (0.5-2.0 μg; RIN≥7) was delivered to the Center for Genomics and Personalized Medicine Research Core Facility (Wake Forest Baptist Medical Center) for microarray assay, where labeled cDNA, generated from total RNA, was assayed on Illumina HT v4 BeadArray microarrays (Illumina Inc.). Following hybridization, washing, and scanning, data were extracted from scanned images using Genome Studio Software (Gene Expression module; Illumina Inc.) and processed for upload to gene expression analysis software.

Statistical Analysis

Following normalization (quantile) and log 2 transformation of the raw data, unsupervised hierarchical clustering and analysis of variance (ANOVA) were performed, using Qlucore Omics Explorer software (Qlucore, Lund, Sweden), to generate principal component analysis (PCA) plots and heat maps. Individual pair-wise comparisons were performed using Student's t-test (fold change ≥1.5; p≤0.05) and groups of differentially-expressed genes (DEGs) were compared between groups using GeneSifter® Analysis Edition software (Perkin Elmer). A receiver operating characteristic (ROC) curve analysis was also performed to evaluate the predictive performance of the most discriminating biomarkers in the peripheral blood.

Pair-Wise Analysis to Determine Differentially-Expressed Transcripts

Gene expression data were uploaded into the GeneSifter® Analysis Edition software (Geospiza, Inc, Seattle, Wash.) software suite. For pair-wise comparisons the data were log transformed (log base 2) prior to performing the Student's t-test, to generate lists of differentially-expressed transcripts (DETs). The fold-change threshold was set at 1.5 and the data were considered significant if the comparison had an associated log ratio p-value ≤0.05.

Principal Component Analysis

In order to determine the overall similarity between samples, ratio data were subjected to Principal Components Analysis (PCA) and two-way agglomerative cluster analysis using Ward's minimum variance as heuristic criteria and Pearson correlation as the distance metric for experiments, and average linkage as heuristic and Pearson correlation distance as the distance metric for genes to determine the overall similarity between samples and within groups. No filtering was applied to the profile level data prior to PCA. These analyses were performed using Qlucore Omics Explorer software (Lund, Sweden). This study examined gene expression in histologically inflamed colonic and/or ileal intestinal mucosal tissue, as well as whole blood, from GI symptomatic children undergoing diagnostic ileocolonoscopy and biopsy for active GI symptoms (Table 1). Subjects included children with a diagnosis of ASD ($ASD^{IC+}$; n=21; mean age=8.11 years old±4.86; 17 males and 4 females). The control group consisted of typically-developing children who underwent diagnostic ileocolonoscopy for chronic GI symptoms in which no histopathology was found (n=24; mean age=12.66 years old±4.08; 18 males and 6 females).

Case Selection and Biopsy Procurement

The $ASD^{IC+}$ group was selected based upon a history of normal development for at least 12 months followed by developmental regression and onset of GI symptoms. For all individuals in this group, this was their first diagnostic ileocolonoscopy and no patients were taking medication thought to alter the histologic appearance of the GI mucosa. All cases had histologically-confirmed ileitis, colitis, or both in at least one of seven collected and archived colonic biopsies. All patients were assigned a diagnosis of either autism (N=13), ASD (N=4) or PDD-NOS (N=4) (Table 1), given by one or more practitioners from the following specialties: pediatric neurology, developmental pediatrics, pediatric psychiatry or psychology. A detailed history of GI symptoms was documented (Table 2). Patients who met clinical criteria for diagnostic ileocolonoscopy and biopsy and whose parents agreed to participate in this IRB-approved study (Copernicus Group Independent Review Board; WFU1-11-081) were provided with a study description and provided fully informed, written consent. Informed written consent from the next of kin, care givers or guardians on the behalf of all the minors/children participants involved in all studies was obtained. Specimens were obtained using a standard disposable forceps biopsy device, in accordance with routine diagnostic biopsy protocol. Immediately upon procurement of biopsy tissue, a specimen from each of seven anatomic locations (from the terminal ileum to rectum) was processed for paraffin embedding and subsequent routine histopathology. Biopsies for microarray analysis were obtained from the divided mucosal specimen at each anatomic location. These tissues were placed directly into RNAlater® solution (Qiagen Inc; Valencia, Calif.) and stored at −80° C. prior to processing.

TABLE 1

Clinical and demographic characteristics of the study population

|  | Cases<br>ASD with inflammation | Controls<br>TD without inflammation |
|---|---|---|
| Number | 21 | 24 |
| Age (years) | | |
| Mean (SD) | 8.11 (4.86) | 12.66 (4.08) |
| Range | 2.3-19.25 | 2.08-17.9 |
| Gender | | |
| Male (%) | 17(81) | 18(75) |
| Female (%) | 4(19) | 6(25) |
| Diagnosis | | |
| Autism | 13 | — |
| ASD | 4 | — |
| PDD-NOS | 4 | — |

TABLE 2

Gastrointestinal symptoms in the ASD study population

|  | $ASD^{IC+}$ N = 21<br>n (%) |
|---|---|
| Abdominal pain | 18 (86) |
| Diarrhea | 16 (76) |
| Constipation | 8 (38) |
| Food sensitivities | 8 (38) |
| Abdominal distention | 7 (33) |
| Failure to thrive | 5 (24) |

Control Biopsy Procurement

Prospective controls (Table 1) were recruited through an IRB approved protocol (Wake Forest University Health Sciences Institutional Review Board; #IRB00007834) from the Pediatric Gastroenterology Clinic at the Wake Forest University Health Sciences. Non-IBD Control subjects were further defined as those who, following ileocolonoscopy, were without endoscopic or pathologic findings explaining their symptoms. However, the initial indication for ileocolonoscopy was presence of unexplained GI symptoms ranging from abdominal pain, diarrhea, malnutrition, blood observed in the stools, etc. Failure to diagnose the etiology of observed symptoms by endoscopy was subsequently followed by clinical reassessment or additional diagnostic testing.

No concerns regarding developmental delays for any participant in the control group were reported by parents, relatives, caretakers, or teachers and none were noted by physicians at the Wake Forest Pediatric GI Clinic.

Tissues for microarray analysis were collected, processed and stored in identical fashion to those from children with ASD. Informed written consent from the next of kin, care givers or guardians on the behalf of all the minors/children participants involved in all studies was obtained.

All specimens (cases and controls) have been collected and stored in identical fashion (e.g. pinch cold biopsy forceps, immediate placement in RNA later, and long-term storage at −20 degrees within 24-48 hours post-collection). Cases were collected at a two locations (Far Rockaway, N.Y. and Austin, Tex.) with controls collected at a third location (Winston Salem, N.C.), and both cases and controls were collected using identical specimen collection protocols as outlined in the SOP submissions to the respective IRB's.

The results of experiments are now described.

Demographics of Cases and Controls $ASD^{IC+}$ Samples

Samples from twenty one children with a diagnosis of ASD (Table 1), chronic unexplained GI symptoms (Table 2) and histologic inflammation of either the terminal ileum (N=9), the colon (N=9), or both locations (N=3) were selected for this study. For each individual, ileal and/or colonic biopsies and a sample of whole blood were collected and processed.

Non-ASD ($TD^{IC-}$) Controls

Samples from twenty four GI symptomatic non-ASD typically developing children without identifiable histologic inflammation on any biopsies in either the ileum or colon ($TD^{IC-}$) were included in this study (Table 1). For each control individual, a terminal ileum or a colonic biopsy specimen, as well as a whole blood sample, was collected and processed.

Principal Component Analysis (PCA)

Unsupervised PCA and hierarchical clustering of the sample level data were performed to determine variability/similarity among samples. No filtering was applied to the profile level data prior to PCA. In this current GI mucosal-based replication study gene expression profiles of inflamed ASD GI mucosal tissue ($ASD^{IC+}$) were compared to non-inflamed TD mucosal tissue ($TD^{IC-}$). There were 21 samples in the $ASD^{IC+}$ group (1 sample from 9 children with histologic ileitis, 1 sample from 9 children with histologic colitis, and 2 samples (1 from the ileum, 1 from the colon) each from 3 children with ileocolitis) and 24 samples (12 from terminal ileum; 12 from colon) in the non-ASD, non-inflamed group. As in the original study (Walker et al., 2013, PLoS One 8:e58058), a clear segregation of GI mucosal derived gene expression profiles emerged between the inflamed and non-inflamed biopsy samples is apparent (FIG. 1).

Ileal Mucosal Gene Expression Profiles

In the PCA plot illustrating the findings in ileal mucosa, profiles from the 12 TD control children without identifiable ileal (nor colonic) inflammation cluster together in one area of the plot while gene expression profiles from inflamed ileal mucosa representing the $ASD^{IC+}$ samples also cluster together, but apart from controls (FIG. 1—top panel).

Colonic Mucosa Gene Expression Profiles

In the PCA plot comparing gene expression profiles in colonic mucosa, samples from the 12 TD control children without identifiable colonic (nor ileal) inflammation cluster relatively tightly together, while inflamed colonic mucosa representing the $ASD^{IC+}$ samples show a separate and much broader distribution (FIG. 1—bottom panel).

Overlapping Gene Expression Profiles from Two Mucosal Based Studies

Figure 2:
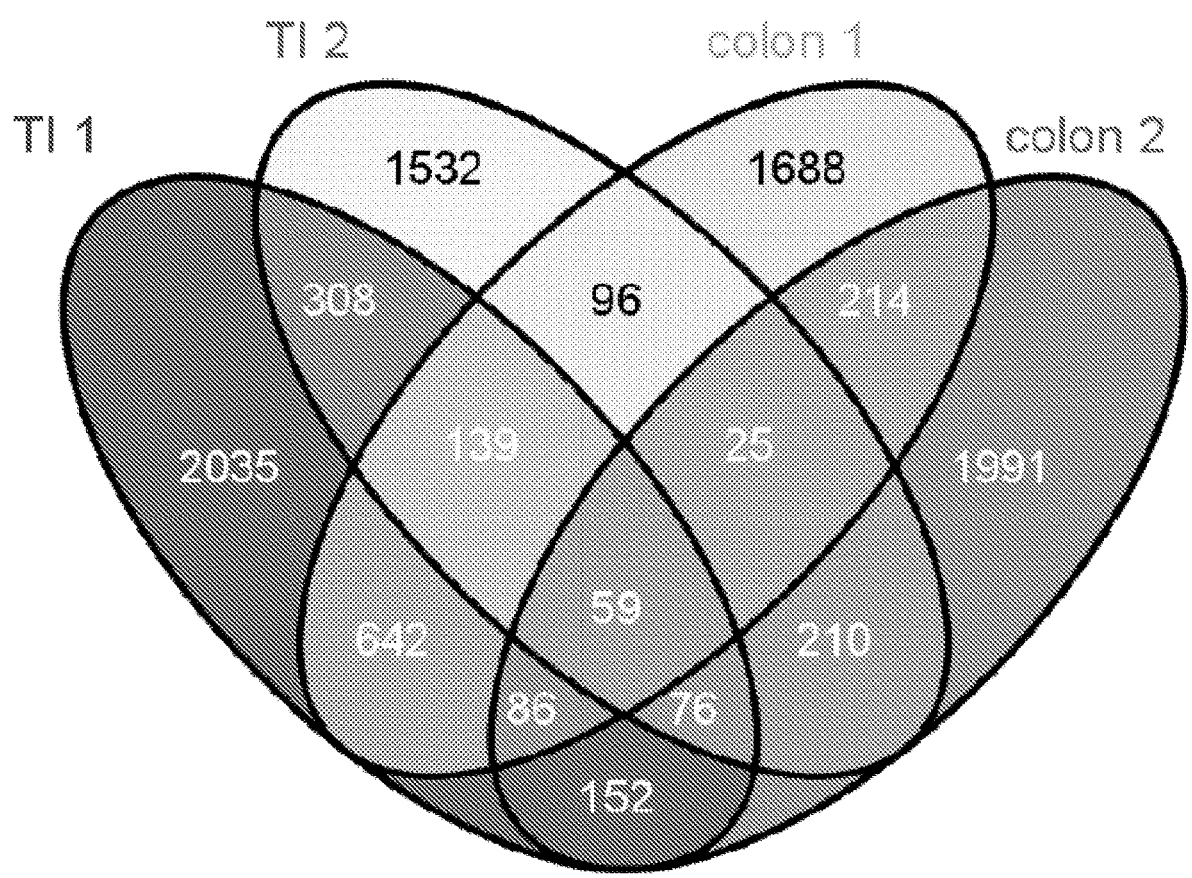
FIG. 2 is a diagram showing differentially-expressed transcripts in two independent studies. Whole genome gene expression was measured in inflamed ileocolonic tissue (either terminal ileum or colon) from ASD patients with ileocolitis and compared to the corresponding non-inflamed tissue from non-ASD controls in two separate studies. The overlap in expression profiles is shown in FIG. 2 (TI 1=terminal ileum data from the first study (25); TI 2=terminal ileum data from the second study; colon 1=colon data from the first study; colon 2=colon data from the second study).

When differential gene expression in GI ileocolonic mucosa biopsy tissue between $ASD^{IC+}$ and non-$ASD^{IC-}$ from our earlier published study (Walker et al., 2013, PLoS One 8:e58058) were compared with the results from this confirmation study, 59 transcripts that were consistently differentially expressed only in inflamed tissue from ASD patients, but not in anatomically matched $TD^{IC-}$ controls were found (FIG. 2; Table 4).

TABLE 4

Transcripts that are differentially expressed in inflamed ileum and colon in $ASD^{IC+}$ cases from two studies

| Gene Name | Gene Identifier |
| --- | --- |
| neurotensin | NM_006183 |
| V-set and immunoglobulin domain containing 2 | NM_014312 |
| neuropeptide Y | NM_000905 |
| gamma-aminobutyric acid type A receptor alpha2 subunit | NM_000807 |
| aquaporin 11 | NM_173039 |
| testis-specific transcript, Y-linked 15 (non-protein coding) | NR_001545 |
| WAP four-disulfide core domain 1 | NM_021197 |
| ephrin-A1 | NM_004428 |
| interleukin 2 receptor subunit alpha | NM_000417 |
| Fc fragment of IgE receptor Ia | NM_002001 |
| solute carrier family 22 member 4 | NM_003059 |
| cytochrome P450 family 2 subfamily S member 1 | NM_030622 |
| meprin A subunit alpha | NM_005588 |
| N-acetylated alpha-linked acidic dipeptidase-like 1 | NM_005468 |
| RAB17, member RAS oncogene family | NM_022449 |
| biotinidase | NM_000060 |
| solute carrier family 26 (anion exchanger), member 2 | NM_000112 |
| vasoactive intestinal peptide receptor 1 | NM_004624 |
| transmembrane channel like 4 | NM_144686 |
| meprin A subunit beta | NM_005925 |
| glucosidase, beta, acid 3 (gene/pseudogene) | NM_020973 |
| period circadian clock 3 | NM_016831 |
| troponin C2, fast skeletal type | NM_003279 |
| ornithine carbamoyltransferase | NM_000531 |
| glutathione S-transferase mu 2 (muscle) pseudogene 1 | NR_002932 |
| actin binding LIM protein family member 2 | NM_032432 |
| thyrotrophic embryonic factor | NM_003216 |
| formyl peptide receptor 1 | NM_002029 |
| epoxide hydrolase 1 | NM_000120 |
| tumor necrosis factor receptor superfamily member 12A | NM_016639 |
| interleukin 1 receptor antagonist | NM_173842 |
| ribosomal protein L39 like | NM_052969 |
| LDL receptor related protein 8 | NM_033300 |
| cyclic nucleotide gated channel alpha 1 | NM_000087 |
| Cdk5 and Abl enzyme substrate 1 | NM_138375 |
| membrane spanning 4-domains A10 | NM_206893 |
| high mobility group box 2 | NM_002129 |
| centromere protein L | NM_033319 |
| dishevelled-binding antagonist of beta-catenin 2 | NM_214462 |
| TNF alpha induced protein 3 | NM_006290 |
| zinc finger protein 358 | NM_018083 |
| polo like kinase 4 | NM_014264 |
| shugoshin-like 2 (S. pombe) | NM_152524 |
| TIMELESS interacting protein | NM_017858 |
| kinesin family member 14 | NM_014875 |
| solute carrier family 27 member 2 | NM_003645 |
| centromere protein E | NM_001813 |
| methylenetetrahydrofolate dehydrogenase 2, methenyltetrahydrofolate cyclohydrolase | NM_006636 |
| ubiquitin like with PHD and ring finger domains 1 | NM_013282 |
| 5PC25, NDC80 kinetochore complex component | NM_020675 |
| sulfiredoxin 1 | NM_080725 |
| sialic acid binding Ig like lectin 17, pseudogene | NR_002804 |
| replication factor C subunit 3 | NM_002915 |
| BUB1 mitotic checkpoint serine/threonine kinase B | NM_001211 |
| helicase, lymphoid-specific | NM_018063 |
| non-SMC condensin I complex subunit G | NM_022346 |
| cytochrome P450 family 51 subfamily A member 1 | NM_000786 |
| calcium voltage-gated channel auxiliary subunit alpha2delta 4 | NM_172364 |
| paired like homeodomain 1 | NM_002653 |

Blood Gene Expression Profiles

Peripheral blood gene expression is being used extensively to identify surrogate markers for disease and, relevant to this study, specifically for discrimination and classification of inflammatory bowel disease. This approach is based on the premise that
peripheral blood, as it interacts with the tissues and cells of the body, may manifest gene
expression changes in response to or because of the diseased tissue they encounter. The second part of the current study was designed to identify transcripts that are differentially expressed in peripheral blood of $ASD^{IC+}$ patients compared to peripheral blood obtained from $TD^{IC-}$ controls. Both $ASD^{IC+}$ and $TD^{IC-}$ control blood was obtained from the same patients, and at the same time, as their respective mucosal tissue. The resulting $ASD^{IC+}$-specific peripheral blood gene expression profile was also compared to DETs that were uniquely expressed in the inflamed ileocolonic mucosal tissue from those same individuals as well as from the original case/control cohort (59 overlapping mucosal DETs; FIG. 2).

Figure 3:
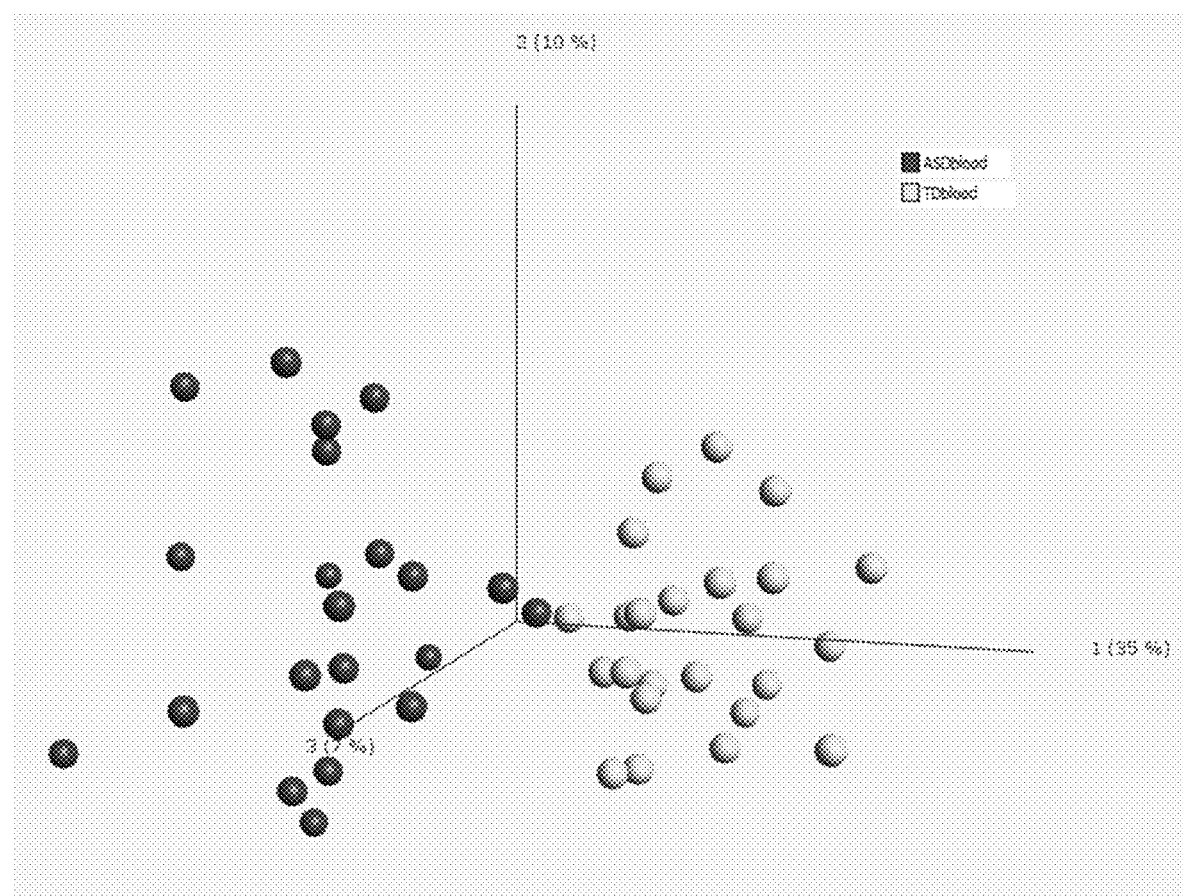
FIG. 3 is a plot showing a comparison of gene expression profiles in peripheral blood from ASD patients with inflamed ileocolonic tissue compared to peripheral blood gene expression from TD controls without ileocolonic inflammation at p=0.001 using principal component analysis. Red/dark grey=ASD blood; Yellow/light grey=TD blood.

Similar to what we found with gene expression in the ileocolonic mucosal tissue sample comparisons, the PCA plots reveal a clear separation between cases and controls in the peripheral blood gene expression profiles (FIG. 3).

Overlapping Differential Gene Expression in Blood and GI Biopsy Tissue in $ASD^{IC+}$ Samples.

Figure 4:
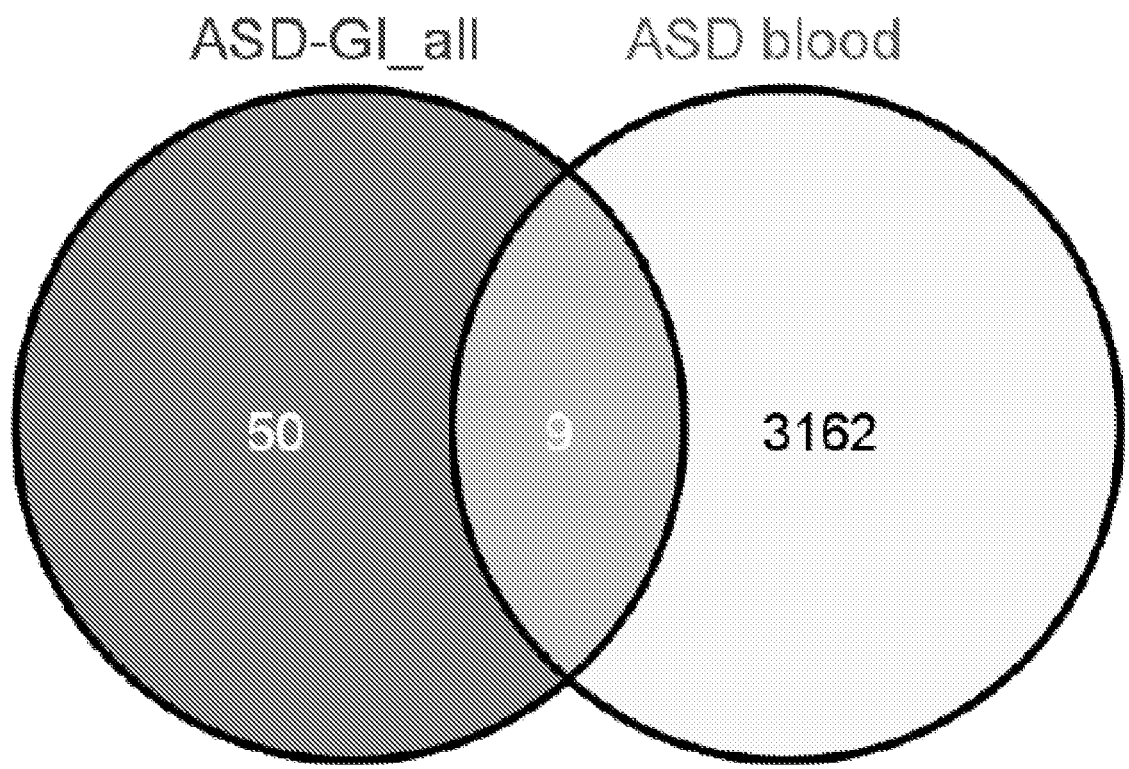
FIG. 4 is a diagram showing overlapping gene expression. Genes that were uniquely differentially-expressed in inflamed gastrointestinal (GI) tissue from ASD patients in two separate studies and the corresponding differential gene expression in blood from all of the cases and controls (from the second study only) were compared to identify those DETs that occur in both tissues.

A pairwise comparison of blood gene expression in $ASD^{IC+}$ samples compared to controls revealed 3171 transcripts that were uniquely differentially-expressed in the blood of $ASD^{IC+}$ individuals. When the overlap of uniquely differentially expressed transcripts (DETs) in the inflamed ileocolonic mucosal tissue from both of the mucosal-based studies were examined, 59 DETs were identified (FIG. 2). Further comparison between these 59 mucosal-based DETs (both studies) with the blood-based DETs (from this study only) revealed nine transcripts that were differentially expressed in both blood and inflamed mucosa in all of the $ASD^{IC+}$ cases (FIG. 4; Table 3). Four of these nine DETs are up-regulated in both ileum and colon in all samples from both studies, and four are down-regulated. One DET, TNFRSF12A, is up-regulated in colon, but down-regulated in terminal ileum (Table 3). In the peripheral blood, the direction of differential
expression (up- or down-regulated) of these nine transcripts matches that in the mucosal tissue in five of nine instances (Table 3). PCR validation of representative DETs in these studies has shown significant agreement with microarray-based findings (Walker et al., 2013, PLoS One 8:e58058).

Receiver Operating Characteristic (ROC) Curve Analysis

Figure 5:
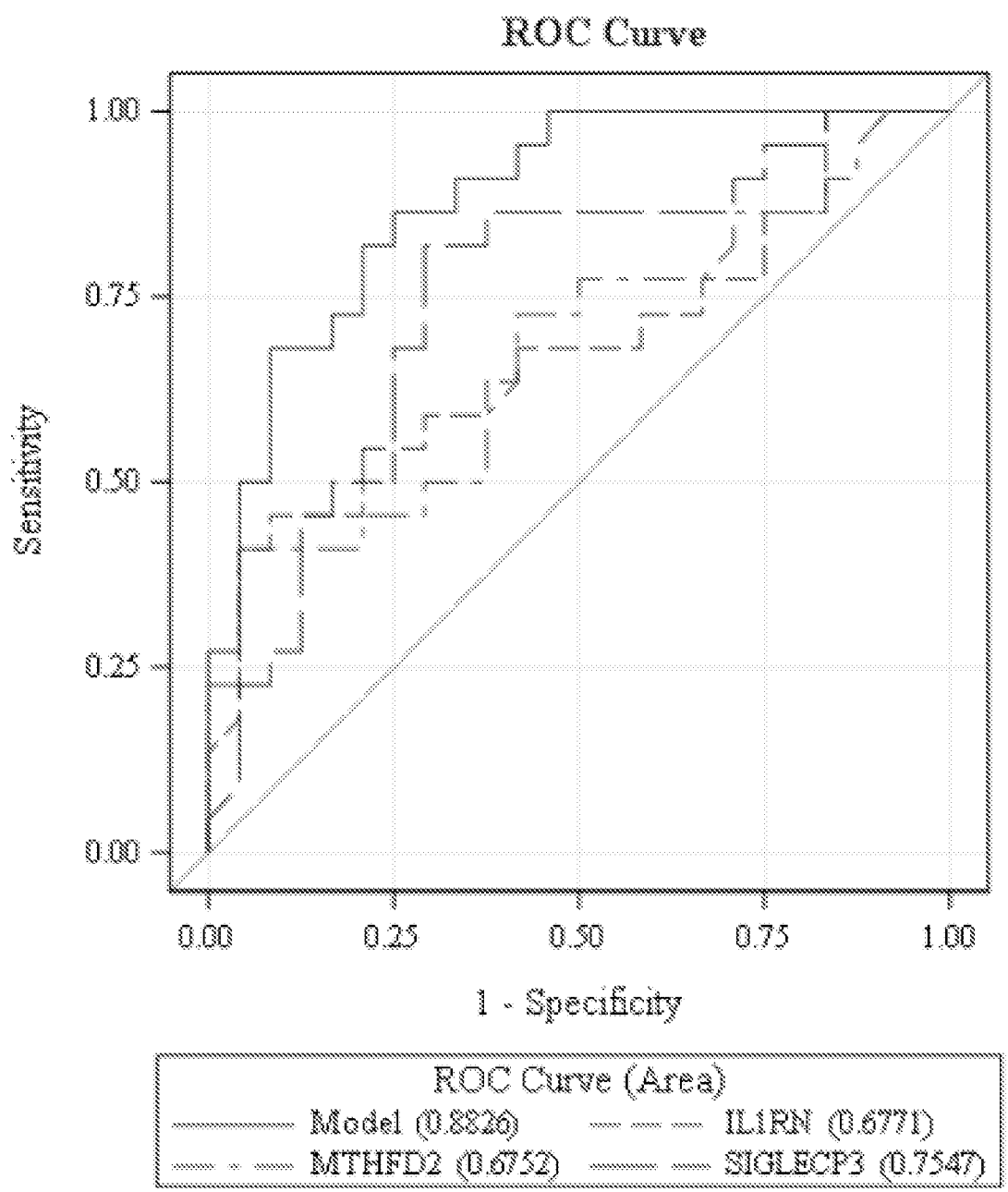
FIG. 5 is a plot showing a receiver operating characteristic (ROC) analysis of blood. The variable selection procedure identified a linear combination of three transcripts that together yielded an area under the curve (AUC) of 0.883.
Figure 6A:
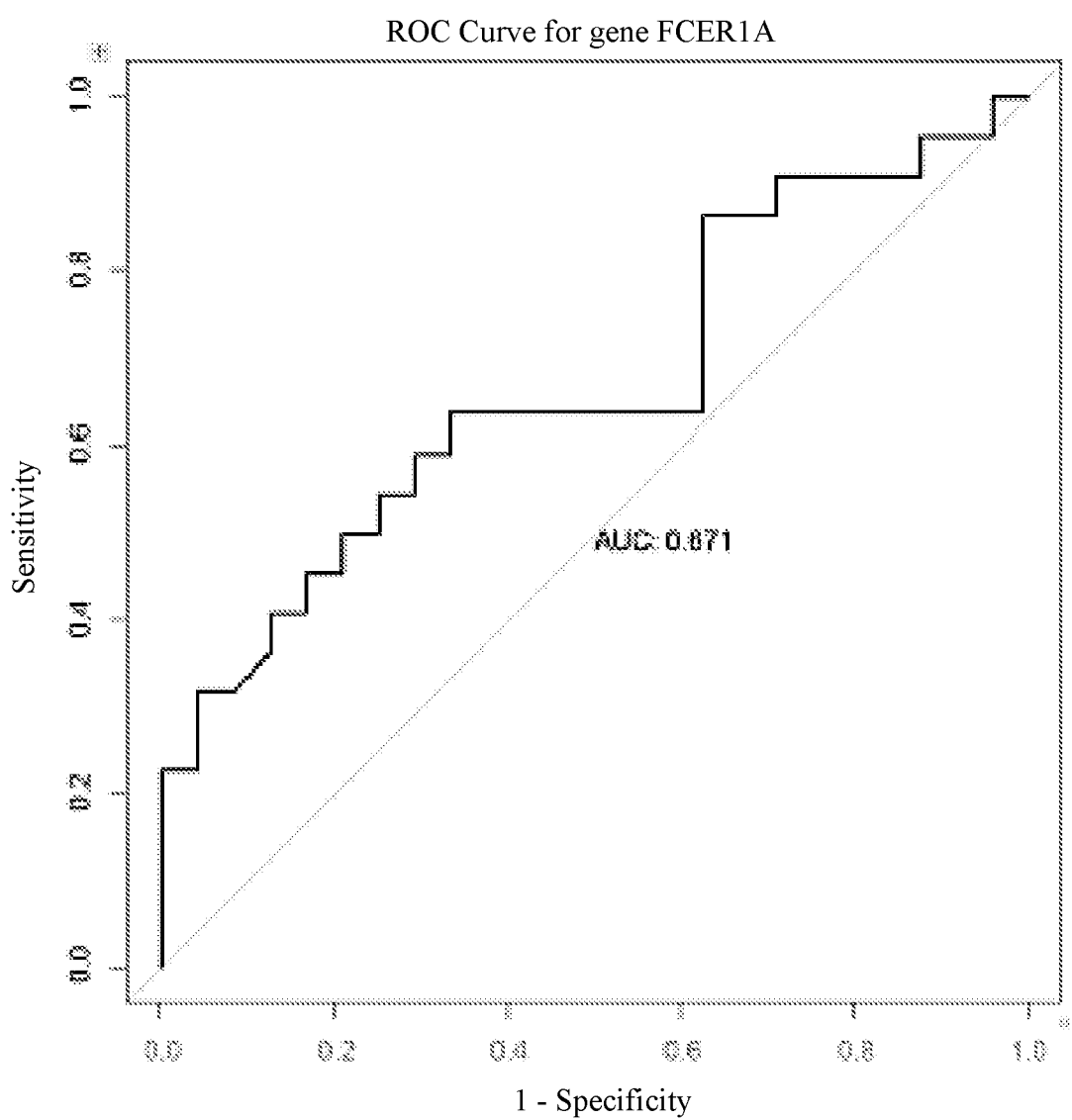
FIGS. 6A-6I are plots showing univariate ROC curves for the nine transcripts found to be differentially expressed in mucosal tissue and blood in $ASD^{IC+}$ individuals.
Figure 6B:
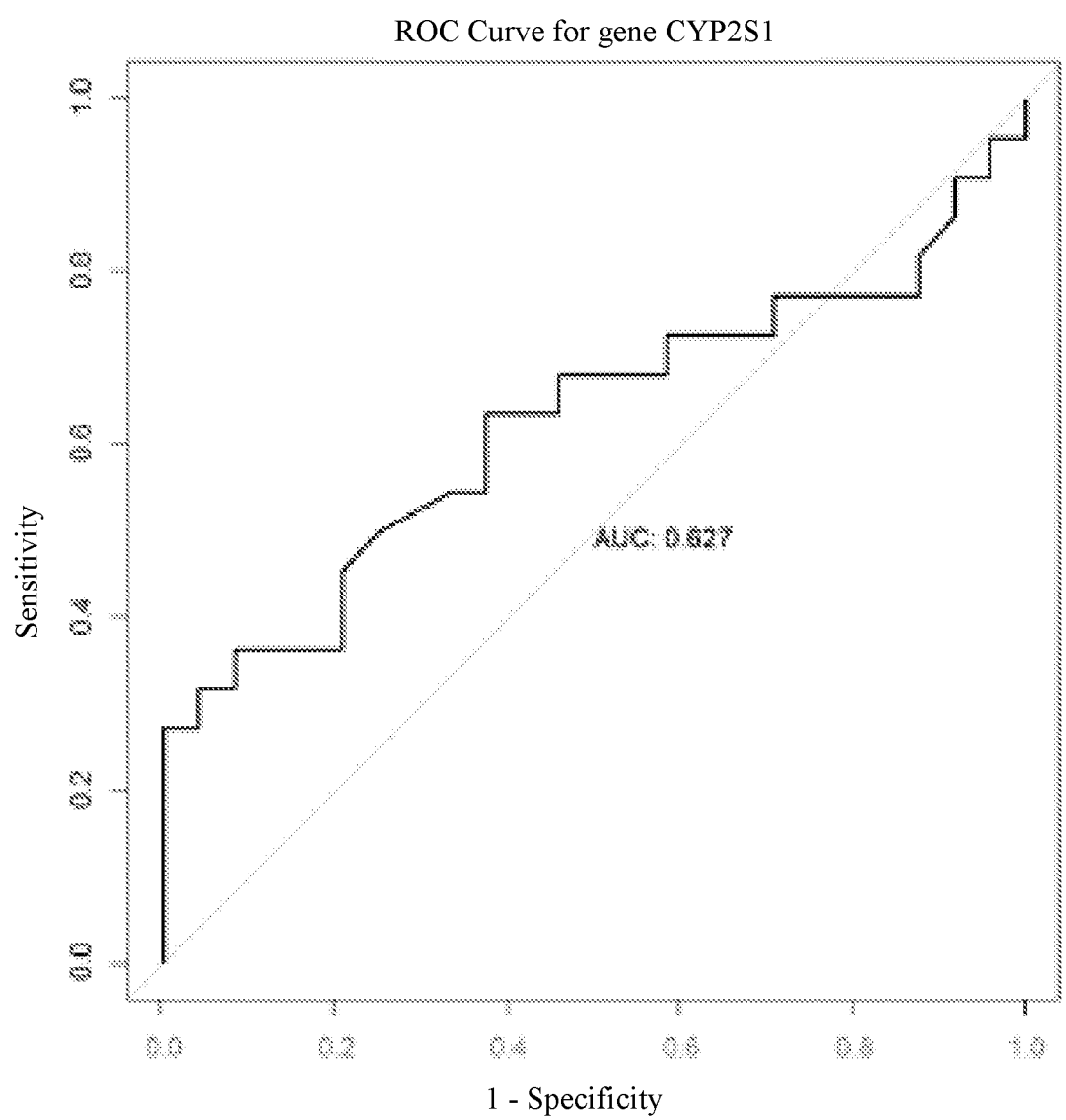
Figure 6C:
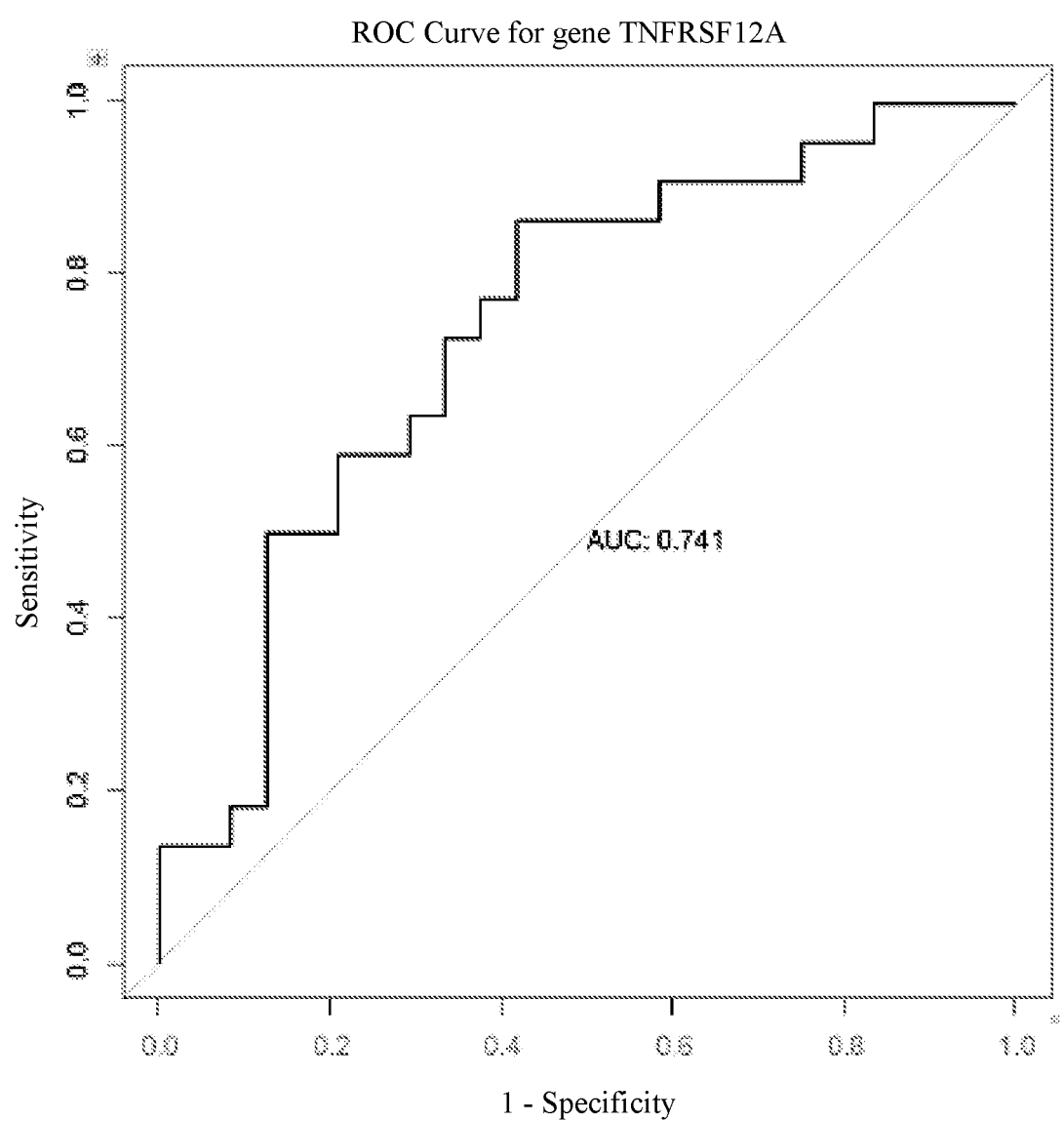
Figure 6D:
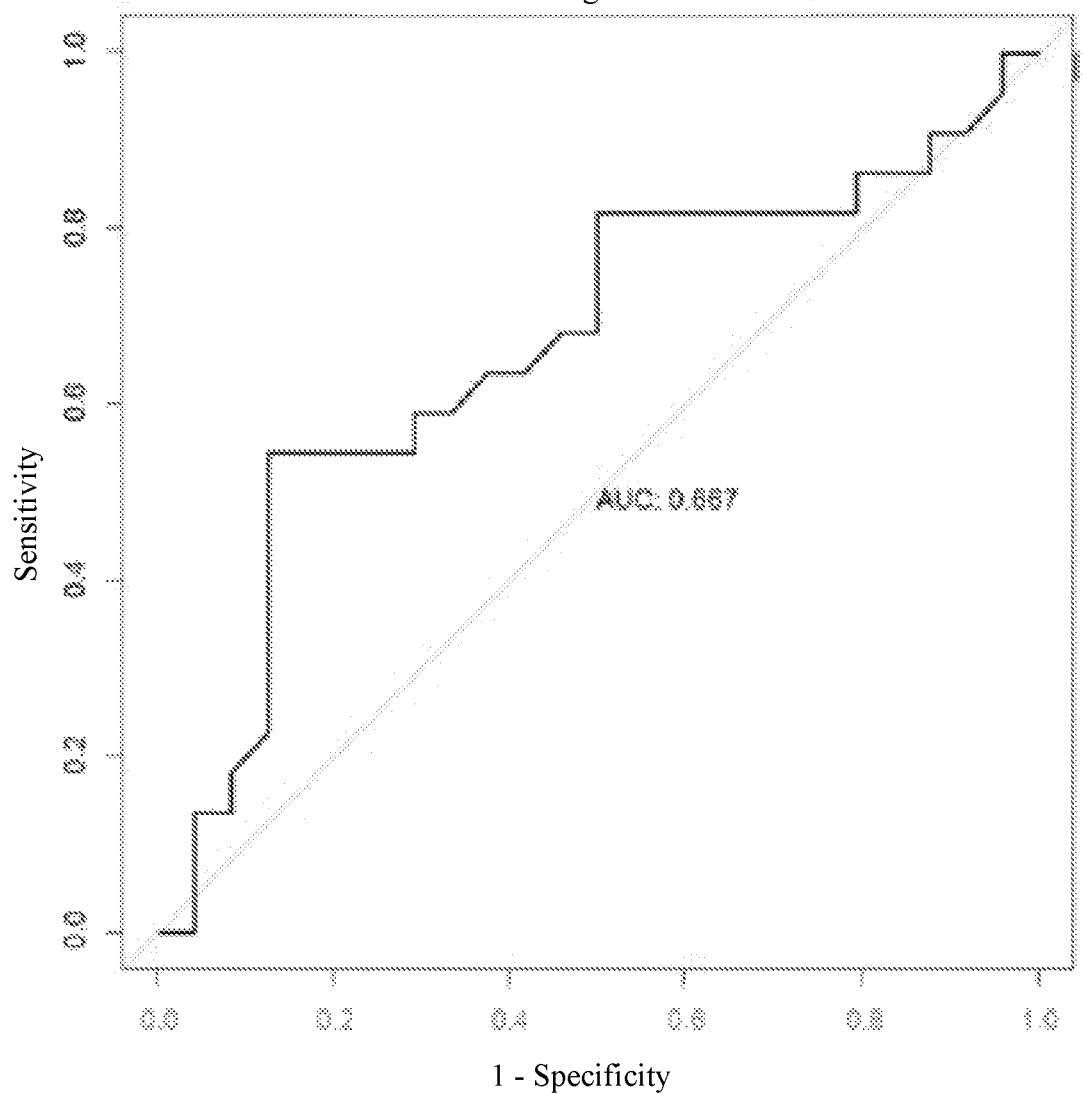
Figure 6E:
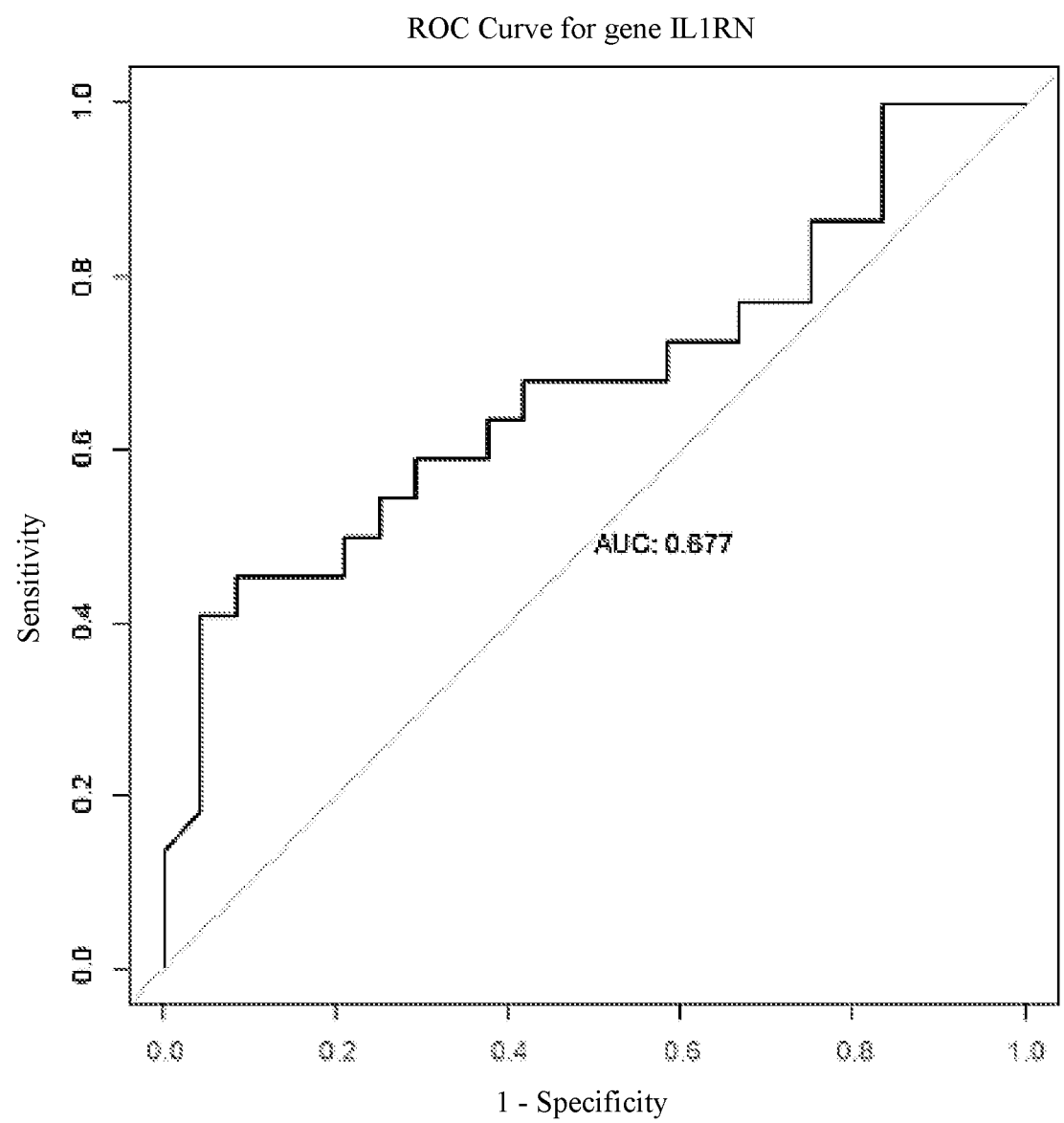
Figure 6F:
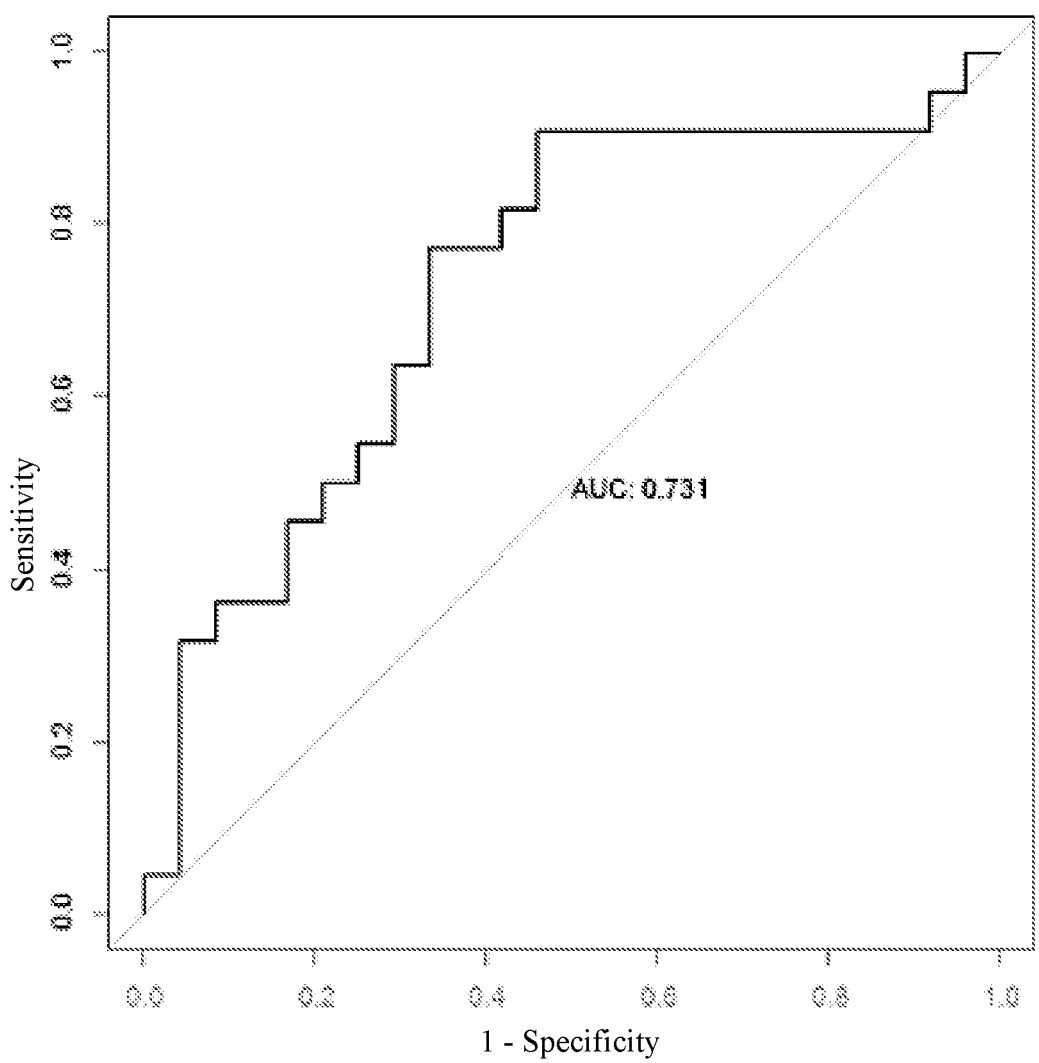
Figure 6G:
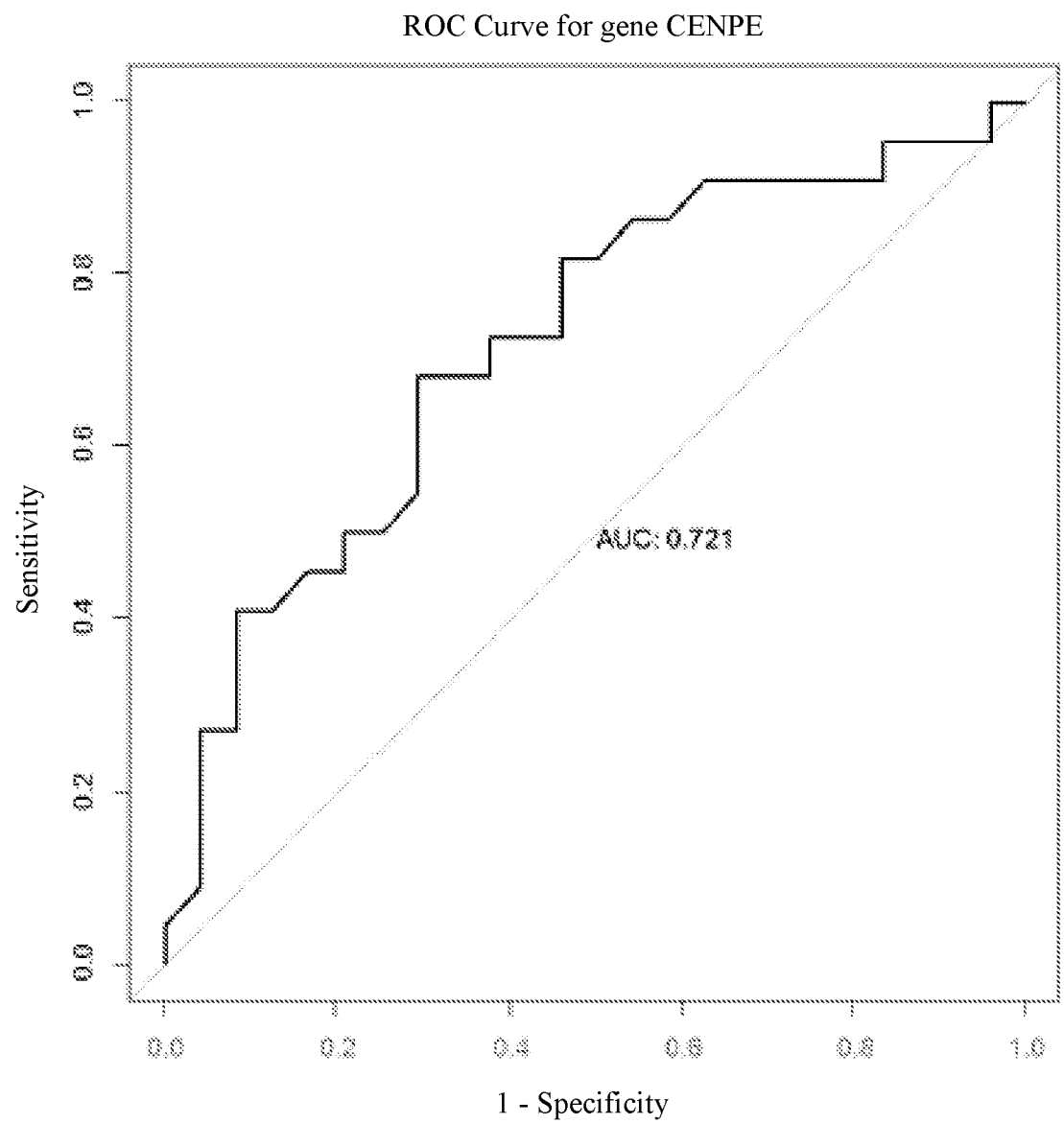
Figure 6H:
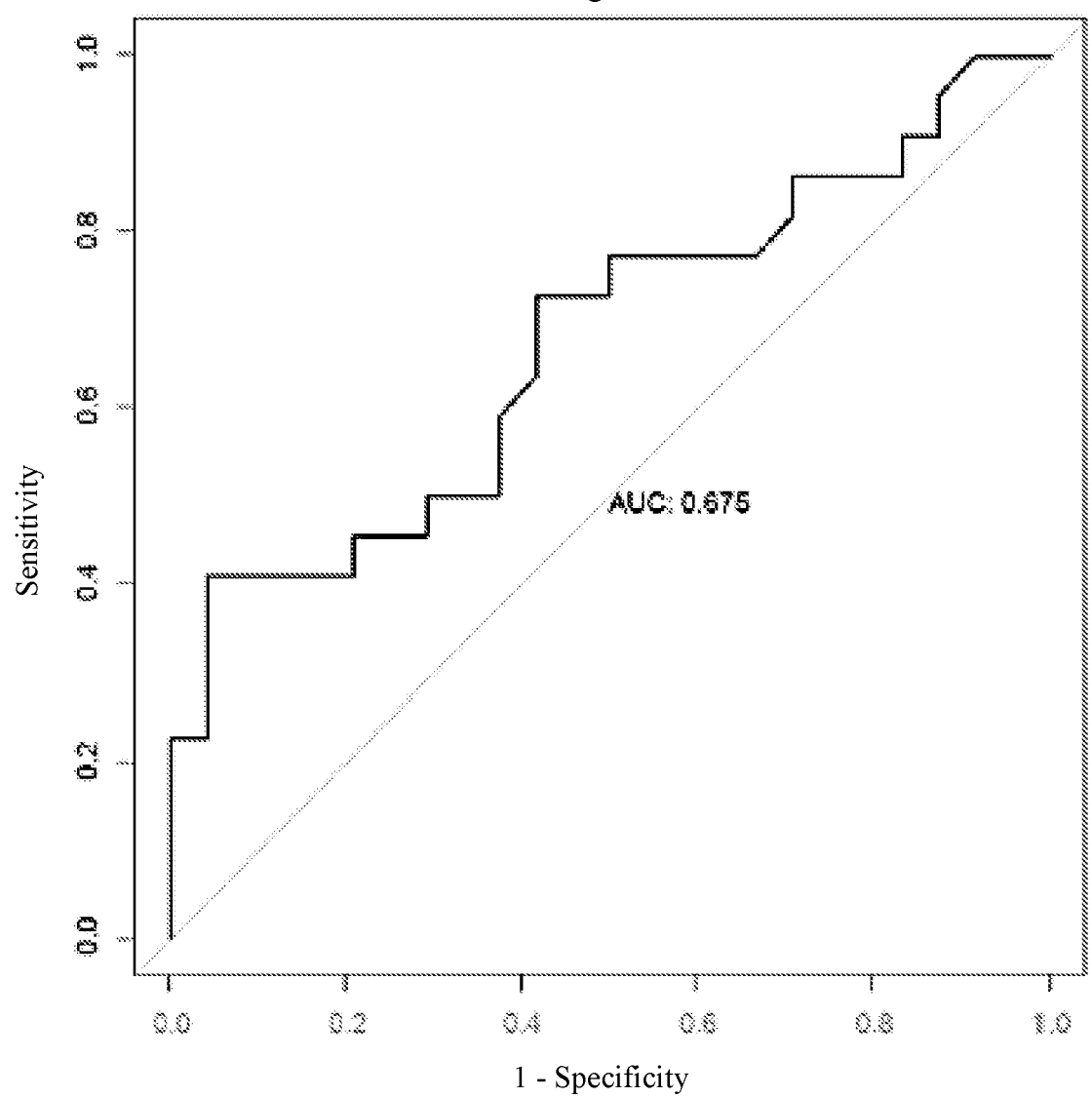
Figure 6I:
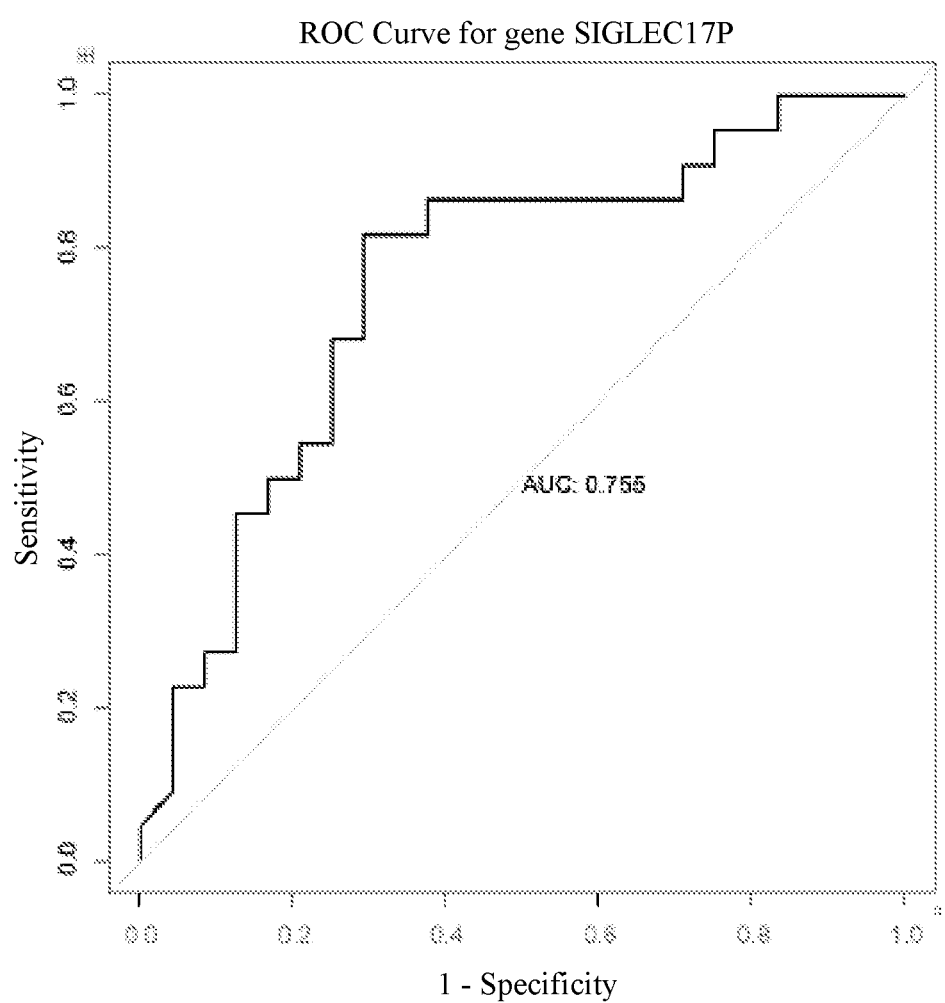

An exploratory ROC analysis of the differentially expressed blood and GI tissue transcripts both univariately and in multivariable linear combinations was performed to evaluate the predictive capability of the blood-based biomarkers. Univariate ROC curve AUC values ranged from 0.627 to 0.755 among the 9 differentially expressed blood-based transcripts (FIGS. 6A-6I). A candidate composite biomarker was created using stepwise variable selection to identify a linear combination of transcripts that maximizes the AUC of a ROC curve, including biomarkers that are significant at a 0.05 level. The variable selection procedure identified a linear combination of three transcripts that together yielded an AUC of 0.883 (FIG. 5).

Blood-Based Biomarker for ASD-Associated Ileocolitis in GI Symptomatic ASD Children Described in the study herein is a blood-based biomarker set (derived from 2 cohorts: cohort #1 (Walker et al., 2013, PLoS One 8:e58058) and cohort #2 (this study)) containing nine mRNA transcripts that reflects the presence of ASD-associated ileocolitis in GI symptomatic ASD children. The findings from cohort #2 demonstrate significant overlap with, and provide validation of, the results from our initial cohort in which we described bowel tissue derived differentially expressed transcripts uniquely present in inflamed ileocolonic tissue from GI symptomatic ASD children (i.e. not found in non-ASD pediatric Crohn's disease, non-ASD pediatric ulcerative colitis, nor in typically-developing children without evidence of intestinal inflammation). Differential expression of fifty nine transcripts was consistently seen in the $ASD^{IC+}$ group in comparisons between GI mucosal tissue (ileum and colon) from the two distinct $ASD^{IC+}$ cohorts and two distinct $TD^{IC-}$ control groups. A subset consisting of nine DETs of these fifty nine mucosal-based transcripts was also found to be differentially expressed in blood (from the cohort #2 only—not measured in the initial study). Moreover, the majority of the nine transcripts identified in both ileocolonic biopsy tissue and blood from $ASD^{IC+}$ children encode proteins that are associated with biologic processes known to be impacted in children with autism, suggesting the peripheral blood marker may not only provide a proxy for GI inflammation, but may provide functional insights as well.

A study was designed herein that capitalizes on the strengths of each of these approaches and have evaluated both the affected organ tissue and blood, taken at the same time and from the same (living) individuals, to identify a clinically-relevant disease biomarker, in a readily-accessible peripheral tissue, for an especially vulnerable patient popu-

TABLE 3

Differential expression (fold change in cases versus controls) of nine transcripts in tissues from two independent studies.

| | | Study #1 | | Study #2 | | |
| --- | --- | --- | --- | --- | --- | --- |
| Accession No. | Gene Symbol | ASD-TI | ASD-colon | ASD-TI | ASD-colon | blood |
| NM_002001 | FCER1A | 2.69 ↓ | 3.52 ↓ | 3.11 ↓ | 1.94 ↓ | 1.55 ↓ |
| NM_030622 | CYP2S1 | 2.56 ↓ | 2.76 ↓ | 2.31 ↓ | 1.63 ↓ | 2.47 ↓ |
| NM_144686 | TMC4 | 2.36 ↓ | 1.59 ↓ | 2.11 ↓ | 1.55 ↓ | 3.16 ↑ |
| NM_016639 | TNFRSF12A | 1.96 ↓ | 3.16 ↑ | 1.75 ↓ | 2.98 ↑ | 2.95 ↓ |
| NM_173842 | IL1RN | 1.94 ↑ | 3.03 ↑ | 6.91 ↑ | 4.22 ↑ | 1.41 ↓ |
| NM_006290 | TNFAIP3 | 1.75 ↑ | 1.62 ↑ | 1.67 ↑ | 1.53 ↑ | 1.26 ↑ |
| NM_001813 | CENPE | 1.66 ↑ | 2.71 ↑ | 1.77 ↑ | 1.51 ↑ | 3.46 ↓ |
| NM_006636 | MTHFD2 | 1.66 ↑ | 2.25 ↑ | 1.85 ↑ | 1.83 ↑ | 1.78 ↓ |
| NR_002804 | SIGLEC17P | 1.63 ↓ | 1.81 ↓ | 3.69 ↓ | 4.83 ↓ | 3.64 ↓ | lation. In the studies herein, a subgroup of ASD children with histopathologically-confirmed gastrointestinal inflammation and, using gene expression profiles in tissue from the inflamed gastrointestinal mucosa compared to expression profiles in peripheral blood from the same cases and controls, identified a putative gene expression profile that can be used by a pediatric gastroenterologist to assess the probability of $ASD^{IC+}$ and as an aid in determining which patients are in need of a more comprehensive work up.

As a follow-up to an earlier identification of unique ASD ileocolitis-associated mucosal tissue based gene expression (Walker et al., 2013, PLoS One 8:e58058), the studies described herein sought to determine which of the (178) DETs from the original cohort were also differentially-expressed in mucosal tissue and peripheral blood within a second cohort. The strategy for identifying a clinically-relevant peripheral biomarker for $ASD^{IC+}$ was based upon the premise that, whenever possible, biomarker discovery should begin in tissue that demonstrates known (and unique) disease-associated pathology (in this case—inflamed GI mucosal tissue) to first identify a disease-specific signature (Walker et al., 2013, PLoS One 8:e58058). This is then followed by analysis of peripheral blood, a tissue which has not been shown to be a "diseased tissue" in autism or $ASD^{IC+}$, but rather functions as a more readily accessible proxy tissue. Overlap of differential expression of specific transcripts within the disease tissue and the proxy tissue provides additional confidence that the peripheral biomarker has validity and clinical relevance (Glatt et al., 2005, Proc Natl Acad Sci USA 102(43):15533-15538).

Although there are dozens of publications reporting the identification of blood-based biomarkers for diseases such as obstructive coronary artery disease (Voros et al., 2014, Atherosclerosis 233(1):284-290), Huntington's disease (Mastrokolias et al., 2015, Eur J Hum Genet 23(10): 1349-1356; Lovrecic et al., 2009, Mov Disord 24(15):2277-2281; Borovecki et al., 2005, Proc Natl Acad Sci USA 102(31): 11023-11028), multiple sclerosis (Gandhi et al., 2010, Hum Mol Genet 19(11):2134-2143), epilepsy and new-onset idiopathic pediatric epilepsy (Karsten et al., 2011, Neurosci Lett 497(3):213-217; Greiner et al., 2013, Epilepsia 54(2):272-279), and recent-onset juvenile idiopathic arthritis (Barnes et al., 2009, Arthritis Rheum 60(7):2102-2112), to name a few, there are only limited numbers of studies that have used gene expression in the target "disease" tissue, correlated with peripheral blood gene expression in the same individuals, obtained at the same time, as a strategy to identify a blood-based biomarker. It is believed this study represents the first effort to use such an approach in ASD children with gastrointestinal inflammation.

The examination of both terminal ileum and colonic specimens in obtaining the initial data set was of great importance as the ASD-associated ileocolitis has been observed to be present in both the small bowel and colon. Evaluation of gene expression in both anatomic locations allowed identification of DETs that are common to both the terminal ileum and large intestine and helped to create an initial data set that did not include transcripts whose differential expression may not reflect disease but rather the site of origin of the tissue (i.e. seen only in TI or seen only in colon).

The majority of the transcripts that comprise the putative blood-based biomarker have functions that are known to be relevant in either ASD, inflammation, or both. For example IL1RN (interleukin 1 receptor antagonist), a potent anti-inflammatory molecule that inhibits the activities of IL1α and IL1β and modulates a variety of interleukin-1 related immune and inflammatory responses, is upregulated in inflamed GI tissues and down-regulated in the peripheral blood. Elevated IL1RN in the inflamed gastrointestinal mucosa makes biological sense in the context of the body's attempt to modulate the damaging effects of the proinflammatory interleukin-1 in the gut and the well-established role of IL-1 in the pathogenesis of GI-related inflammatory disorders (Lopetuso et al., 2013, Front Immunol 9(4):1-20). Lower circulating levels of IL1RN may constitute a peripheral signal of the active inflammatory response occurring in the GI tract.

In addition to its role in GI inflammation, IL-1 is also known to play a major role in neuroinflammation (Moynagh et al., 2005, J Anat 207(3):265-269) and has been shown to contribute to neuroinflammatory-associated breakdown of the blood brain barrier (Hofman et al., 1986, J Immunol 136(9):3239-3245). The IL-1 family of cytokines is one of many proinflammatory cytokines present in excess in children with autism (Krakowiak et al., 2015, Biol Psychiatry 2015 Aug. 14. pii: S0006-3223(15)00655-1; Heuer et al., 2008, Autism Res 1(5):275-283; Ashwood et al., 2011, Brain Behav Immun 25(1):40-45) and both neuroinflammation and deficits in blood brain barrier function have been implicated in the pathogenesis of ASD related brain dysfunction (Theoharides et al., 2011, J Neuroinflammation 6(166):1-5).

An important cytokine receptor transcript in this putative biomarker, TNFRSF12A (tumor necrosis factor receptor superfamily 12A), is over-expressed in inflamed colonic tissue and down-regulated in both the terminal ileum and peripheral blood of $ASD^{IC+}$ cases. This receptor (aka Fn14) binds the tumor necrosis factor superfamily member TWEAK (TNF-like weak inducer of apoptosis), a pro-inflammatory cytokine implicated in tissue regeneration and wound repair (Brown et al., 2013, PLoS One 8(6):1-11). The binding of TWEAK to its receptor activates several signaling cascades including the NF-κB pathway, and sustained Fn14 signaling has been implicated in the pathogenesis of chronic IBD. Moreover, it has been postulated that TWEAK-independent Fn14 signaling may occur in instances where Fn14 levels are highly elevated (Brown et al., 2013, PLoS One 8(6):1-11). Interestingly, elevated Fn14 expression correlates highly with elevated MET (hepatocyte growth factor receptor that encodes tyrosine kinase activity) in a form of metastatic cancer, and depletion of Fn14 is sufficient to inhibit MET driven tumor cell migration and invasion in vitro (Whitsett et al., 2014, Clin Exp Metastasis 31(6):613-623). The human MET gene is a well-established risk factor for ASD that functions in both brain development and gastrointestinal repair, and has been shown to confer a distinct risk in families with co-occurring autism and gastrointestinal conditions (Peng et al., 2016, Mol Psychiatry 182:1-11; Campbell et al., 2009, Pediatrics 123(3):1018-1024).

Another key signaling molecule, TNFAIP3 (tumor necrosis factor, alpha-induced protein 3), a transcript also up-regulated both in GI tissue and blood, is rapidly induced by TNF and has been shown to inhibit NF-κB activation as well as TNF-mediated apoptosis. TNFα has been shown to be present in both peripheral lymphocytes and inflamed ASD small and large intestinal mucosal tissue in excess of that found in $TD^{IC-}$ and TD Crohn's disease (Ashwood et al., 2004, J Clin Immunol 24: 664-673; Ashwood et al., 2006, J Neuroimmunol 173: 126-134; Jyonouchi et al., 2001, J Neuroimmunol 120(1-2):170-179). Moreover, variants of TNFAIP3 are also known risk factors for celiac disease and are implicated in altered NF-κB signaling (Trynka et al., 2009, Gut 58(8): 1078-1083).

The high affinity IgE receptor FcεR1 (consisting of one a subunit, one β subunit, and two γ subunits) is constitutively expressed in mast cells and basophils and initiates the allergic response upon interaction with allergens (Greer et al., 2014, J Clin Invest 124(3): 1187-1198). In humans, but not rodents, FcεR1 is also constitutively expressed in dendritic cells and monocytes, although this form of receptor is trimeric (lacking the β subunit) and it has been proposed that on dendritic cells, the receptor promotes immune homeostasis and regulation (Shin et al., 2015, Cell Mol Life Sci 72(12):2349-2360). The studies herein found that the gene encoding the alpha subunit for this receptor, FCER1A, was down-regulated in both the mucosal tissue and peripheral blood from $ASD^{IC+}$ cases. Without intending to be bound by theory, it is believed this finding further supports the concept of an imbalance in immune homeostasis in $ASD^{IC+}$.

A key mitochondrial folate pathway gene, MTHFD2 (methylenetetrahydrofolate dehydrogenase (NADP+ dependent) 2, methenyltetrahydrofolate cyclohydrolase) encodes a nuclear-encoded bifunctional mitochondrial enzyme and was found herein to be up-regulated in inflamed GI tissue and down-regulated in peripheral blood in $ASD^{IC+}$ cases. Importantly, while this gene is expressed in 13 developing embryos, it is typically absent in most healthy adult tissues. MTHFD2 RNA and protein have been shown, however, to be markedly elevated in many cancers and negatively correlated with survival in breast cancer (Nilsson et al., 2014, Nat Commun 5(3128): 1-10). Moreover, mitochondrial dysfunction has been shown to be associated with ASD, although the precise role has yet not been entirely explained (Rossignol et al., 2014, Front Physiol. 22(5): 1-15; Frye et al., 2015, Microb Ecol Health Dis 26(27458):1-17).

Finally, CYP2S1 (cytochrome P450, family 2), which encodes an extra-hepatic xenobiotic metabolizing enzyme expressed in high levels in epithelial tissues such as those found in the lung, skin and colon (Deb et al., 2009, Expert Opin Drug Metab Toxicol 5(4):367-380), is down-regulated in blood and in GI tissue of $ASD^{IC+}$ cases. CYP2S1 functions to catalyze reactions involved in drug metabolism and synthesis of cholesterol, steroids, and other lipids and some studies suggest the enzyme may play an important role in modulating inflammation. Whether it acts as in anti-inflammatory or pro-inflammatory mode depends upon the substrate it encounters (Deb et al., 2009, Expert Opin Drug Metab Toxicol 5(4):367-380). Of interest in the context of IBD, CYP2S1 has been shown to be negatively regulated by corticosteroids, specifically the synthetic glucocorticoid dexamethasone, in human cell lines (Bui et al., 2011, Drug Metab Dispos 39(2):180-190). Glucocorticoids are widely used to treat allergic, inflammatory, and autoimmune conditions so this may provide one explanation for the reduction in CYP2S1 observed in the studies herein.

The clinical utility of a blood-based biomarker that predicts, with high probability, the presence of $ASD^{IC+}$ can hardly be overstated. With the frequency of GI symptoms in ASD acknowledged as being more common than in TD children and, in some studies as high as 70%, and with the prevalence of ASD at 1 in 68 American children, the sheer number of GI symptomatic ASD children of any age will be substantial. An as yet unknown, but potentially high, fraction of these will have the $ASD^{IC+}$ phenotype. Because empiric therapy of IBDs will at best provide only short respite (and can even make symptoms worse), and because of the known association between severity of GI symptoms and extremes of ASD behaviors, identifying those children most likely to be $ASD^{IC+}$ is critically important for any pediatric gastroenterologist faced with an ASD child with chronic GI symptoms in making the decision as to whether diagnostic endoscopy is indicated.

Clinical symptom presentation alone does not allow the clinician to distinguish those ASD children with a chronic inflammatory bowel disease from those who do not have a chronic inflammatory process occurring in the bowel (Krigsman et al., 2010, Autism Insights 1: 1-11). The specter of subjecting all such GI symptomatic ASD children to diagnostic endoscopy presents a huge logistical problem in the setting of current clinical practice in terms of time needed to be spent with the parents describing the procedure and explaining the need for such diagnostic testing, the difficulty in performing bowel preps in these often uncooperative and poorly communicative children (and young adults), the ability to manage patients with significant behavioral, cognitive, and emotional deficits in the endoscopy suite, the ability to safely anesthetize them, and the ability to manage them in the postoperative area upon awakening from anesthesia in a manner that insures their safety and the safety of other patients. Contemplation of such large-scale diagnostic procedures can be reduced to manageable numbers by initial screening, using biomarkers, so that available resources of time, personnel, and money can be focused on the patients statistically most likely to be diagnosed (predicted by a simple blood test) with ileocolitis upon biopsy.

Although this current study includes a more age- and gender-matched sample than the original pilot study (Walker et al., 2013, PLoS One 8:e58058), the numbers of cases and controls are still relatively modest and constitute an important study limitation. So although the finding of overlap in the differentially-expressed transcripts from the inflamed GI tissues between the two studies was both encouraging and expected, as was the reduction in the overall number of DETs unique to the $ASD^{IC+}$ samples when combining the two data sets, these findings need to be validated in a much larger sample. The putative nine-transcript biomarker, reflecting the overlap in peripheral blood gene expression with GI mucosal based gene expression, while statistically compelling, will need to be replicated in additional blood samples as the data in this study, relating to blood gene expression, are derived from a single cohort of 21 cases and 24 controls. ROC analyses suggest that a subset of the nine transcripts comprising the putative marker, consisting of three genes (MTHFD2, IL1RN, and SIGLECP3), provides a reasonable level of sensitivity and specificity with a combined AUC of 0.88.

Differences in diet, medications, age, gender, and nutritional supplements used by many children in the study group may affect gene expression of the GI mucosa. Strict control of these factors in an attempt at uniformity is not practical in autism research, and our finding of consistent gene expression profiles across the wide variation of these variables in two distinct study cohorts effectively minimize their potential effect on the validity of the findings described herein.

There are some additional limitations regarding the controls used in these studies. Although peripheral blood from GI symptomatic ASD children can serve as a proxy tissue for $ASD^{IC+}$ (i.e. ileocolonic inflammation in ASD children), the influence of the ASD phenotype itself on the blood gene expression profile cannot be ruled out. That is, the findings herein do not distinguish whether the nine unique blood-based DETs reflect the autism phenotype alone or the autism-plus-ileocolitis phenotype. If the former, the findings would be of even greater clinical significance. To address this, follow-on studies will include whole blood samples from two additional control groups: (1) ASD children without GI symptoms and (2) TD children without GI symptoms.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. In particular, the disclosure of United States Patent Publication No. 2015-0361499 A1 is incorporated herein by reference in its entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating autism spectrum disorder (ASD) in a human subject, the method comprising:

measuring in a blood sample from said subject a level of expression of each of IL1RN mRNA, MTHFD2 mRNA, and SIGLEC17P mRNA;

comparing the expression levels measured in the blood sample from said subject to control expression levels of each corresponding mRNA in blood samples from a control cohort that does not have ASD;

detecting at least one of a decreased level of expression of IL1RN, a decreased level of expression of MTHFD2, or a decreased level of expression of SIGLEC17P in the blood sample from said subject as compared to the control expression level;

wherein said detecting at least one of a decrease in the level of expression of IL1RN, a decrease in the level of expression of MTHFD2, or a decrease in the level of expression of SIGLEC17P indicates that the subject has ASD; and administering a treatment to the subject, wherein the treatment comprises corticosteroids, immunomodulators, 5-aminosalicylic acid preparations, cytokine specific antagonists, antimicrobials, probiotics, and/or supplemental digestive enzymes.

2. The method of claim 1, further comprising measuring the level of TNFRSF12A polynucleotide.

3. The method of claim 1, wherein the method further comprises detecting an increase in the level of expression of TMC4 mRNA, an increase in the level of expression of TNFAIP3 mRNA, a decrease in the level of expression of FCER1A mRNA, a decrease in the level of expression of CYP2S1 mRNA, a decrease in the level of expression of TNFRSF12A mRNA, or a decrease in the level of expression of CENPE mRNA in the blood sample from the subject as compared to the expression in blood samples from the control cohort.

4. The method of claim 1, wherein the autism spectrum disorder is autism.

5. The method of claim 1, wherein said subject is a child.

6. The method of claim 1, wherein measuring comprises PCR assays or microarrays.

* * * * *